(12) United States Patent
Brookings et al.

(10) Patent No.: US 7,763,729 B2
(45) Date of Patent: *Jul. 27, 2010

(54) BICYCLIC HETEROAROMATIC DERIVATIVES

(75) Inventors: Daniel Christopher Brookings, Berkshire (GB); Jeremy Martin Davis, Berkshire (GB); Barry John Langham, Berkshire (GB)

(73) Assignee: UCB Pharma S.A., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/187,936

(22) Filed: Aug. 7, 2008

(65) Prior Publication Data

US 2009/0042877 A1 Feb. 12, 2009

Related U.S. Application Data

(62) Division of application No. 10/518,725, filed as application No. PCT/GB03/02667 on Jun. 20, 2003, now Pat. No. 7,423,047.

(30) Foreign Application Priority Data

Jun. 20, 2002 (GB) ................................. 0214268.5

(51) Int. Cl.
*C07D 513/04* (2006.01)
*A61K 31/4365* (2006.01)

(52) U.S. Cl. ...................... 546/114; 514/301
(58) Field of Classification Search ................ 546/114; 514/301
See application file for complete search history.

(56) References Cited

U.S. PATENT DOCUMENTS

| | | | |
|---|---|---|---|
| 7,521,460 B2 * | 4/2009 | Brookings et al. | 514/301 |
| 7,592,455 B2 * | 9/2009 | Brookings et al. | 546/114 |
| 2006/0004025 A1 | 1/2006 | Brookings et al. | |

FOREIGN PATENT DOCUMENTS

WO WO99/64400 12/1999
WO WO03/033502 4/2003

OTHER PUBLICATIONS

Henry, J.R. et al., "Potent Inhibitors of the Map Kinase p38", Bioorganice & Medicinal Chemistry Letters, vol. 8, No. 23, Dec. 1, 1998, pp. 3335-3340.
International Search Report PCT/GB03/02667, dated Sep. 24, 2003.

* cited by examiner

*Primary Examiner*—Rita J Desai
*Assistant Examiner*—David K O'Dell
(74) *Attorney, Agent, or Firm*—McDonnell Boehnen Hulbert & Berghoff LLP

(57) ABSTRACT

Bicyclic heteroaromatic derivatives of formula (1) are described: F(1) where: the dashed line joining A and C($R^a$) is present and represents a bond and A is a —N= atom or a —C($R^b$)= group, or the dashed line is absent and A is a —N($R^b$)—, or —C($R^b$)($R^c$)— group; X is an —O—, —S— or substituted nitrogen atom or a —S(O)—, —S($O_2$)— or —NH-group; Y is a nitrogen or substituted carbon atom or a —CH= group; n is zero or the integer 1; $Alk^1$ is an optionally substituted aliphatic or heteroaliphatic chain $L^1$ is a covalent bond or a linker atom or group; $Cy^1$ is a hydrogen atom or an optionally substituted cycloaliphatic, polycycloaliphatic, heterocycloaliphatic, polyheterocycloaliphatic, aromatic or heteroaromatic group; Ar is an optionally substituted aromatic or heteroaromatic group; and the remaining substituents are defined in the specification. The compounds are potent and selective inhibitors of p38 kinase and are of use in the prophylaxis and treatment of immune or inflammatory disorders.

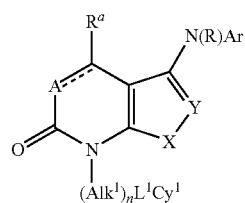

(1)

19 Claims, No Drawings

BICYCLIC HETEROAROMATIC DERIVATIVES

This invention relates to a series of 5-6 fused ring bicyclic heteroaromatic derivatives, to compositions containing them, to processes for their preparation and to their use in medicine.

Immune and inflammatory responses involve a variety of cell types with control and co-ordination of the various interactions occurring via both cell-cell contacts (e.g integrin interactions with their receptors) and by way of intercellular signalling molecules. A large number of different signalling molecules are involved, including cytokines, lymphocytes, chemokines and growth factors.

Cells respond to such intercellular signalling molecules by means of intracellular signalling mechanisms that include protein kinases, phosphatases and phospholipases. There are five classes of protein kinase of which the major ones are the tyrosine kinases and the serine/threonine kinases [Hunter, T., Methods in Enzymology (Protein Kinase Classification) p. 3, Hunter, T. and Sefton, B. M.; eds. Vol. 200, Academic Press; San Diego, 1991].

One sub-class of serine/threonine kinases is the mitogen activating protein (MAP) kinases of which there are at least three families which differ in the sequence and size of the activation loop [Adams, J. L. et al., Progress in Medicinal Chemistry p. 1-60, King, F. D. and Oxford, A. W.; eds. vol 38, Elsevier Science, 2001]: (i) the extracellular regulated kinases (ERKs), (ii) the c-Jun $NH_2$ terminal kinases or stress activated kinases (JNKs or SAP kinases) and (iii) the p38 kinases which have a threonine-glycine-tyrosine (TGY) activation motif. Both the JNKs and p38 MAP kinases are primarily activated by stress stimuli including, but not limited to, proinflammatory cytokines e.g. tumour necrosis factor (TNF) and interleukin-1 (IL-1), ultraviolet light, endotoxin and chemical or osmotic shock.

Four isoforms of p38 have been described (p38α/β/γ/δ). The human p38α enzyme was initially identified as a target of cytokine-suppressive anti-inflammatory drugs (CSAIDs) and the two isoenzymes found were initially termed CSAID binding protein-1 (CSBP-1) and CSBP-2 [Lee, J. C. et al, Nature (London) 1994, 372, 739-46]. CSBP-2 is now widely referred to as p38α and differs from CSBP-1 in an internal sequence of 25 amino acids as a result of differential splicing of two exons that are conserved in both mouse and human [McDonnell, P. C. et al, Genomics 1995, 29, 301-2]. CSBP-1 and p38α are expressed ubiquitously and there is no difference between the two isoforms with respect to tissue distribution, activation profile, substrate preference or CSAID binding. A second isoform is p38β which has 70% identity with p38α. A second form of p38β termed p38β2 is also known and of the two this is believed to be the major form. p38α and p38β2 are expressed in many different tissues. However in monocytes and macrophages p38α is the predominant kinase activity [Lee, J. C., ibid; Jing, Y. et al., J. Biol. Chem. 1996, 271, 10531-34; Hale, K. K. et al, J. Immun. 1999, 162, 4246-52]. p38γ and p38δ (also termed SAP kinase-3 and SAP kinase-4 respectively) have ~63% and ~61% homology to p38α respectively. p38γ is predominantly expressed in skeletal muscle whilst p38δ is found in testes, pancreas, prostate, small intestine and in certain endocrine tissues.

All p38 homologues and splice variants contain a 12 amino acid activation loop that includes a Thr-Gly-Tyr motif. Dual phosphorylation of both Thr-180 and Tyr-182 in the TGY motif by a dual specificity upstream kinase is essential for the activation of p38 and results in a >1000-fold increase in specific activity of these enzymes [Doza, Y. N. et al FEBS Lett., 1995, 364, 7095-8012]. This dual phosphorylation is effected by MKK6 and under certain conditions the related enzyme MKK3 [Enslen, H. et al J. Biol. Chem., 1998, 273, 1741-48]. MKK3 and MKK6 belong to a family of enzymes termed MAPKK (mitogen activating protein kinase kinase) which are in turn activated by MAPKKK (mitogen activating kinase kinase kinase) otherwise known as MAP3K.

Several MAP3Ks have been identified that are activated by a wide variety of stimuli including environmental stress, inflammatory cytokines and other factors. MEKK4/MTK1 (MAP or ERK kinase kinase/MAP three kinase-1), ASK1 (apoptosis stimulated kinase) and TAK1 (TGF-β-activated kinase) are some of the enzymes identified as upstream activators of for MAPKKs. MEKK4/MTK1 is thought to be activated by several GADD-45-like genes that are induced in response to environmental stimuli and which eventually lead to p38 activation [Takekawa, M. and Saito, H. Cell, 1998, 95, 521-30]. TAK1 has been shown to activate MKK6 in response to transforming growth factor-β (TGF-β). TNF-stimulated activation of p38 is believed to be mediated by the recruitment of TRAF2 [TNF receptor associated factor] and the Fas adaptor protein, Daxx, which results in the activation of ASK1 and subsequently p38.

Several substrates of p38 have been identified including other kinases [e.g. MAPK activated protein kinase 2/3/5 (MAPKAP 2/3/5), p38 regulated/activated protein kinase (PRAK), MAP kinase-interacting kinase 1/2 (MNK1/2), mitogen- and stress-activated protein kinase 1 (MSK1/RLPK) and ribosomal S6 kinase-B (RSK-B)]; transcription factors [e.g. activating transcription factor 2/6 (ATF2/6), monocyte-enhancer factor-2A/C (MEF2A/C), C/EBP homologous protein (CHOP), Elk1 and Sap-1a1]; and other substrates [e.g. cPLA2, p47phox].

MAPKAP K2 is activated by p38 in response to environmental stress. Mice engineered to lack MAPKAP K2 do not produce TNF in response to lipopolysaccharide (LPS). Production of several other cytokines such as IL-1, IL-6, IFN-g and IL-10 is also partially inhibited [Kotlyarov, A. et al Nature Cell Biol. 1999, 1, 94-7]. Further, MAPKAP K2 from embryonic stem cells from p38α null mice was not activated in response to stress and these cells did not produce IL-6 in response to IL-1 [Allen, M. et al, J. Exp. Med. 2000, 191, 859-69]. These results indicate that MAPKAP K2 is not only essential for TNF and IL-1 production but also for signalling induced by cytokines. In addition MAPKAP K2/3 phosphorylate and thus regulate heat shock proteins HSP 25 and HSP 27 which are involved in cytoskeletal reorganization.

Several small molecule inhibitors of p38 have been reported which inhibit IL-1 and TNF synthesis in human monocytes at concentrations in the low 1M range [Lee, J. C. et al, Int. J. Immunopharm. 1988, 10, 835] and exhibit activity in animal models which are refactory to cyclooxygenase inhibitors [Lee, J. C. et al, Annals N.Y. Acad. Sci. 1993, 696, 149]. In addition these small molecule inhibitors are known to decrease the synthesis of a wide variety of pro-inflammatory proteins including IL-6, IL-8, granulocyte/macrophage colony-stimulating factor (GM-CSF) and cyclooxygenase-2 (COX-2). TNF-induced phosphorylation and activation of cytosolic PLA2, TNF-induced expression of VCAM-1 on endothelial cells and IL-1 stimulated synthesis of collagenase and stromelysin are also inhibited by small molecule inhibitors of p38 [Cohen, P. Trends Cell Biol. 1997, 7, 353-61].

A variety of cells including monocytes and macrophages produce TNF and IL-1. Excessive or unregulated TNF production is implicated in a number of disease states including Crohn's disease, ulcerative colitis, pyresis, rheumatoid arthritis, rheumatoid spondylitis, osteoarthritis, gouty arthritis and other arthritic conditions, toxic shock syndrome, endotoxic shock, sepsis, septic shock, gram negative sepsis, bone resporption diseases, reperfusion injury, graft vs. host reaction, allograft rejection, adult respiratory distress syndrome, chronic pulmonary inflammatory disease, silicosis, pulmonary sarcoisosis, cerebral malaria, scar tissue formation, keloid formation, fever and myalgias due to infection, such as influenza, cachexia secondary to acquired immune deficiency syndrome (AIDS), cachexia secondary to infection or malignancy, AIDS or AIDS related complex.

Excessive or unregulated IL-1 production has been implicated in rheumatoid arthritis, osteoarthritis, traumatic arthritis, rubella arthritis, acute synovitis, psoriatic arthritis, cachexia, Reiter's syndrome, endotoxemia, toxic shock syndrome, tuberculosis, atherosclerosis, muscle degeneration, and other acute or chronic inflammatory diseases such as the inflammatory reaction induced by endotoxin or inflammatory bowel disease. In addition IL-1 has been linked to diabetes and pancreatic β cells [Dinarello, C. A. J. Clinical Immunology, 1985, 5, 287-97].

IL-8 is a chemotactic factor produced by various cell types including endothelial cells, mononuclear cells, fibroblasts and keratinocytes. IL-1, TNF and LPS all induce the production of IL-8 by endothelial cells. In vitro IL-8 has been shown to have a number of functions including being a chemoattractant for neutrophils, T-lymphocytes and basophils. IL-8 has also been shown to increase the surface expression of Mac-1 (CD11b/CD18) on neutrophils without de novo protein synthesis which may contribute to increased adhesion of neutrophils to vascular endothelial cells. Many diseases are characterised by massive neutrophil infiltration. Histamine release from basophils (in both atopic and normal individuals) is induced by IL-8 as is lysozomal enzyme release and respiratory burst from neutrophils.

The central role of IL-1 and TNF together with other leukocyte derived cytokines as important and critical inflammatory mediators is well documented. The inhibition of these cytokines has been shown or would be expected to be of benefit in controlling, alleviating or reducing many of these disease states.

The central position that p38 occupies within the cascade of signalling molecules mediating extracellular to intracellular signalling and its influence over not only IL-1, TNF and IL-8 production but also the synthesis and/or action of other pro-inflammatory proteins (e.g. IL-6, GM-CSF, COX-2, collagenase and stromelysin) make it an attractive target for inhibition by small molecule inhibitors with the expectation that such inhibition would be a highly effective mechanism for regulating the excessive and destructive activation of the immune system. Such an expectation is supported by the potent and diverse anti-inflammatory activities described for p38 kinase inhibitors [Adams, ibid; Badger, et al, J. Pharm. Exp. Ther. 1996, 279, 1453-61; Griswold, et al., Pharmacol. Comm., 1996, 7, 323-29].

We have now found a group of compounds which are potent and selective inhibitors of p38 kinase (p38α, β, δ and γ) and the isoforms and splice variants thereof, especially p38α, p38β and p38β2. The compounds are thus of use in medicine, for example in the prophylaxis and treatment of immune or inflammatory disorders as described herein.

Thus according to one aspect of the invention we provide a compound of formula (1):

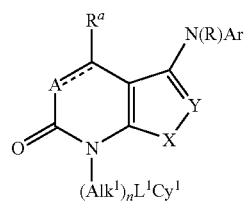

wherein:
the dashed line joining A and C($R^a$) is present and represents a bond and
A is a —N═ atom or a —C($R^b$)═ group, or the dashed line is absent and A is a —N($R^b$)—, or —C($R^b$)($R^c$)— group;
$R^a$, $R^b$ and $R^c$ is each independently a hydrogen atom or an optionally substituted $C_{1-6}$alkyl, —CN, —$CO_2$H, —$CO_2R^1$ (where $R^1$ is an optionally substituted alkyl group), —$CONH_2$, —$CONHR^1$ or —$CONR^1R^2$ group (where $R^2$ is an optionally substituted alkyl group);
R is a hydrogen atom or a straight or branched $C_{1-6}$ alkyl group;
X is an —O—, —S— or substituted nitrogen atom or a —S(O)—, —$S(O_2)$— or —NH-group;
Y is a nitrogen or substituted carbon atom or a —CH═ group;
n is zero or the integer 1;
$Alk^1$ is an optionally substituted aliphatic or heteroaliphatic chain
$L^1$ is a covalent bond or a linker atom or group;
$Cy^1$ is a hydrogen atom or an optionally substituted cycloaliphatic, polycycloaliphatic, heterocycloaliphatic, polyheterocycloaliphatic, aromatic or heteroaromatic group;
Ar is an optionally substituted aromatic or heteroaromatic group; and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise. In addition, compounds of formula (1) may exist as tautomers, for example keto ($CH_2C$═O)-enol (CH═CHOH) tautomers. Formula (1) and the formulae hereinafter are intended to represent all individual tautomers and mixtures thereof, unless stated otherwise.

As used in formula (1) the terms "substituted nitrogen atom" and "substituted carbon atom" are intended to include groups such as those in which X is —N($R^{10}$)— and Y is —C($R^{10}$)═ where $R^{10}$ is a substituent other than a hydrogen atom as generally or particularly defined hereinafter.

The following general terms as used herein in relation to compounds of the invention and intermediates thereto have the stated meaning below unless specifically defined otherwise.

Thus as used herein the term "alkyl" whether present as a group or part of a group includes straight or branched $C_{1-6}$alkyl groups, for example $C_{1-4}$alkyl groups such as methyl, ethyl, n-propyl, i-propyl, n-butyl, s-butyl, i-butyl or t-butyl groups. Similarly, the terms "alkenyl" or "alkynyl" are intended to mean straight or branched $C_{2-6}$alkenyl or $C_{2-6}$alkynyl groups such as $C_{2-4}$alkenyl or $C_{2-4}$alkynyl groups. Optional substituents which may be present on these groups include those optional substituents mentioned hereinafter in relation to $Alk^1$ when $Alk^1$ is an optionally substituted aliphatic chain.

The term halogen is intended to include fluorine, chlorine, bromine or iodine atoms.

The term "haloalkyl" is intended to include those alkyl groups just mentioned substituted by one, two or three of the halogen atoms just described. Particular examples of such groups include —$CF_3$, —$CCl_3$, —$CHF_2$, —$CHCl_2$, —$CH_2F$ and —$CH_2Cl$ groups.

The term "alkoxy" as used herein is intended to include straight or branched $C_{1-6}$alkoxy e.g. $C_{1-4}$alkoxy such as methoxy, ethoxy, n-propoxy, i-propoxy, n-butoxy, s-butoxy, i-butoxy and t-butoxy. "Haloalkoxy" as used herein includes any of these alkoxy groups substituted by one, two or three halogen atoms as described above. Particular examples include —$OCF_3$, —$OCCl_3$, —$OCHF_2$, —$OCHCl_2$, —$OCH_2F$ and —$OCH_2Cl$ groups.

As used herein the term "alkylthio" is intended to include straight or branched $C_{1-6}$alkylthio, e.g. $C_{1-4}$alkylthio such as methylthio or ethylthio.

As used herein the term "alkylamino or dialkylamino" is intended to include the groups —$NHR^{1a}$ and —$N(R^{1a})(R^{1b})$ where $R^{1a}$ and $R^{1b}$ is each independently an optionally substituted straight or branched alkyl group or both together with the N atom to which they are attached form an optionally substituted heterocycloalkyl group which may contain a further heteroatom or heteroatom containing group such as an —O— or —S— atom or —$N(R^{1a})$— group. Particular examples of such optionally substituted heterocycloalkyl groups include optionally substituted pyrrolidinyl, piperidinyl, morpholinyl, thiomorpholinyl and N'-$C_{1-6}$alkyl-piperazinyl groups. The optional substituents which may be present on such heterocycloalkyl groups include those optional substituents as described hereinafter in relation to aliphatic chains such as $Alk^1$.

When $Alk^1$ is present in compounds of formula (1) as an optionally substituted aliphatic chain it may be an optionally substituted $C_{1-10}$aliphatic chain. Particular examples include optionally substituted straight or branched chain $C_{1-6}$alkylene, $C_{2-6}$alkenylene, or $C_{2-6}$alkynylene chains.

Particular examples of aliphatic chains represented by $Alk^1$ include optionally substituted —$CH_2$—, —$CH_2CH_2$—, —$CH(CH_3)CH_2$—, —$(CH_2)_2CH_2$—, —$(CH_2)_3CH_2$—, —$CH(CH_3)(CH_2)_2CH_2$—, —$CH_2CH(CH_3)CH_2$—, —$C(CH_3)_2CH_2$—, —$CH_2C(CH_3)_2CH_2$—, —$(CH_2)_2CH(CH_3)CH_2$—, —$CH(CH_3)CH_2CH_2$—, —$CH(CH_3)CH_2CH(CH_3)CH_2$—, —$CH_2CH(CH_3)CH_2CH_2$—, —$(CH_2)_2C(CH_3)_2CH_2$—, —$(CH_2)_4CH_2$—, —$(CH_2)_5CH_2$—, —CHCH—, —CHCHCH$_2$—, —CH$_2$CHCH—, —CHCHCH$_2$CH$_2$—, —CH$_2$CHCHCH$_2$—, —$(CH_2)_2$CHCH—, —CC—, —CCCH$_2$—, —CH$_2$CC—, —CCCH$_2$CH$_2$—, —CH$_2$CCCH$_2$— or —$(CH_2)_2$CCH— chains.

Heteroaliphatic chains represented by $Alk^1$ in the compounds of formula (1) include the aliphatic chains just described but with each additionally containing one, two, three or four heteroatoms or heteroatom-containing groups. Particular heteroatoms or groups include atoms or groups $L^2$ where $L^2$ is a linker atom or group. Each $L^2$ atom or group may interrupt the aliphatic group, or may be positioned at its terminal carbon atom to connect the group to an adjoining atom or group. Particular examples include optionally substituted -$L^2$CH$_2$—, —CH$_2L^2$-, -$L^2$CH(CH$_3$)—, —CH(CH$_3$)$L^2$-, —CH$_2L^2$CH$_2$—, -$L^2$CH$_2$CH$_2$—, -$L^2$CH$_2$CH(CH$_3$)—, —CH(CH$_3$)CH$_2L^2$-, —CH$_2$CH$_2L^2$-, —CH$_2L^2$CH$_2$CH$_2$—, —CH$_2L^2$CH$_2$CH$_2L^2$-, —(CH$_2$)$_2L^2$CH$_2$—, —(CH$_2$)$_3L^2$CH$_2$—, -$L^2$(CH$_2$)$_2$CH$_2$—, -$L^2$CH$_2$CHCH—, —CHCHCH$_2L^2$- and —(CH$_2$)$_2L^2$CH$_2$CH$_2$— chains.

When $L^2$ is present in heteroaliphatic chains as a linker atom or group it may be any divalent linking atom or group. Particular examples include —O— or —S— atoms or —(O)—, —C(O)O—, —OC(O)—, —C(S)—, —S(O)—, —S(O)$_2$—, —$N(R^3)$— [where $R^3$ is a hydrogen atom or a straight or branched alkyl group], —$N(R^3)$O—, —$N(R^3)$N—, —$CON(R^3)$—, —$OC(O)N(R^3)$—, —$CSN(R^3)$—, —$N(R^3)CO$—, —$N(R^3)C(O)O$—, —$N(R^3)CS$—, —$S(O)_2N(R^3)$—, —$N(R^3)S(O)_2$—, —$N(R^3)CON(R^3)$—, —$N(R^3)CSN(R^3)$— or —$N(R^3)SO_2N(R^3)$— groups. Where $L^2$ contains two $R^3$ groups these may be the same or different.

The optional substituents which may be present on aliphatic or heteroaliphatic chains represented by $Alk^1$ [and, unless stated otherwise, on alkyl, cycloalkyl heterocycloalkyl and other aliphatic or heteroaliphatic groups where specifically mentioned herein] include one, two, three or more substituents where each substituent may be the same or different and is selected from halogen atoms, e.g. fluorine, chlorine, bromine or iodine atoms, or —OH, —$CO_2$H, —$CO_2R^4$ [where $R^4$ is an optionally substituted straight or branched $C_{1-6}$alkyl group, and is in particular a straight or branched $C_{1-4}$alkyl group], e.g. —$CO_2CH_3$ or —$CO_2C(CH_3)_3$, —$CONHR^4$, e.g. —$CONHCH_3$, —$CON(R^4)_2$, e.g. —$CON(CH_3)_2$, —$COR^4$, e.g. —$COCH_3$, $C_{1-6}$alkoxy, e.g. methoxy or ethoxy, halo$C_{1-6}$alkoxy, e.g. trifluoromethoxy or difluoromethoxy, thiol (—SH), —$S(O)R^4$, e.g. $S(O)CH_3$, —$S(O)_2R^4$, e.g. —$S(O)_2CH_3$, $C_{1-6}$alkylthio e.g. methylthio or ethylthio, amino, —$NHR^4$, e.g. —$NHCH_3$ or —$N(R^4)_2$, e.g. —$N(CH_3)_2$ groups. Where two $R^4$ groups are present in any of the above substituents these may be the same or different.

In addition when two $R^4$ alkyl groups are present in any of the optional substituents just described these groups may be joined, together with the N atom to which they are attached, to form a heterocyclic ring. Such heterocyclic rings may be optionally interrupted by a further heteroatom or heteroatom containing group selected from —O—, —S—, —$N(R^4)$—, —C(O)— or —C(S)— groups. Particular examples of such heterocyclic rings include piperidinyl, pyrazolidinyl, morpholinyl, thiomorpholinyl, pyrrolidinyl, imidazolidinyl and piperazinyl rings.

When $L^1$ is present in compounds of formula (1) as a linker atom or group it may be any such atom or group as hereinbefore described in relation to $L^2$ linker atoms and groups.

Optionally substituted cycloaliphatic groups represented by the group $Cy^1$ in compounds of the invention include optionally substituted $C_{3-10}$cycloaliphatic groups. Particular examples include optionally substituted $C_{3-10}$cycloalkyl, e.g. $C_{3-7}$cycloalkyl or $C_{3-10}$cycloalkenyl, e.g $C_{3-7}$cycloalkenyl groups.

Optionally substituted heterocycloaliphatic groups represented by the group $Cy^1$ include optionally substituted 3 to 10 membered saturated or partially saturated monocyclic hydrocarbon rings containing one or more heteroatoms or heteroatom containing groups, such as optionally substituted $C_{3-10}$heterocycloaliphatic groups. Particular examples include optionally substituted $C_{3-10}$heterocycloalkyl, e.g. $C_{3-7}$heterocycloalkyl or $C_{3-10}$heterocycloalkenyl, e.g. $C_{3-7}$heterocycloalkenyl groups, each of said groups containing one, two, three or four heteroatoms or heteroatom containing groups $L^4$ in place of or in addition to the ring carbon atoms where $L^4$ is an atom or group as previously defined for $L^2$.

Optionally substituted polycycloaliphatic groups represented by the group $Cy^1$ include optionally substituted $C_{7-10}$bi- or tricycloalkyl or $C_{7-10}$bi- or tricycloalkenyl groups. Optionally substituted heteropolycycloaliphatic groups represented by the group $Cy^1$ include optionally substituted $C_{7-10}$bi- or tricycloalkyl or $C_{7-10}$bi- or tri-cycloalkenyl groups containing one, two, three, four or more $L^4$ atoms or groups in place of or in addition to the ring carbon atoms.

Particular examples of cycloaliphatic, polycycloaliphatic, heterocycloaliphatic and heteropolycycloaliphatc groups represented by the group $Cy^1$ include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, dihydrofuranyl, tetrahydrofuranyl, tetrahydropyranyl, dihydrothiophenyl, tetrahydrothiophenyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, 5,6-dihydro-2(1H)-pyrazinone, tetrahydropyrimidinyl, thiazolinyl, thiazolidinyl, pyranyl, e.g. 2- or 4-pyranyl, piperidinyl, homopiperidinyl, heptamethyleneiminyl, piperidinone, 1,4-dioxanyl, morpholinyl, morpholinone, 1,4-dithianyl, thiomorpholinyl, piperazinyl, homopiperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, 1,3,5-oxadiazinyl, dihydroisothiazolyl, dihydroisothiazole 1,1-dioxide, e.g. 2,3-dihydroisothiazole 1,1-dioxide, dihydropyrazinyl and tetrahydropyrazinyl groups.

The optional substituents which may be present on the cycloaliphatic, polycycloaliphatic, heterocycloaliphatic or heteropolycycloaliphatic groups represented by the group $Cy^1$ include one, two, three or more substituents selected from halogen atoms, or $C_{1-6}$alkyl, e.g. methyl or ethyl, halo$C_{1-6}$alkyl, e.g. halomethyl or haloethyl such as difluoromethyl or trifluoromethyl, optionally substituted by hydroxyl, e.g. $C(OH)(CF_3)_2$, $C_{1-6}$alkoxy, e.g. methoxy or ethoxy, halo$C_{1-6}$alkoxy, eg. halomethoxy or haloethoxy such as difluoromethoxy or trifluoromethoxy, thiol, $C_{1-6}$alkylthiol, e.g. methylthiol or ethylthiol, carbonyl (═O), thiocarbonyl (═S), imino (═$NR^{4a}$) [where $R^{4a}$ is an —OH group or a $C_{1-6}$alkyl group], or -(Alk$^3$)$_v$R$^5$ groups in which Alk$^3$ is a straight or branched $C_{1-3}$alkylene chain, v is zero or the integer 1 and $R^5$ is a $C_{3-8}$cycloalkyl, —OH, —SH, —N(R$^6$)(R$^7$) [in which $R^6$ and $R^7$ is each independently selected from a hydrogen atom or an optionally substituted alkyl or $C_{3-8}$cycloalkyl group], —OR$^6$, —SR$^6$, —CN, —NO$_2$, —CO$_2$R$^6$, —SOR$^6$, —SO$_2$R$^6$, —SO$_3$R$^6$, —OCO$_2$R$^6$, —C(O)R$^6$, —OC(O)R$^6$, —C(S)R$^6$, —C(O)N(R$^6$)(R$^7$), —OC(O)N(R$^6$)(R$^7$), —N(R$^6$)C(O)R$^7$, —C(S)N(R$^6$)(R$^7$), —N(R$^6$)C(S)R$^7$, —SO$_2$N(R$^6$)(R$^7$), —N(R$^6$)SO$_2$R$^7$, —N(R$^6$)C(O)N(R$^7$)(R$^8$) [where $R^8$ is as defined for $R^6$], —N(R$^6$)C(S)N(R$^7$)(R$^8$), —N(R$^6$)SO$_2$N(R$^7$)(R$^8$) or an optionally substituted aromatic or heteroaromatic group.

Particular examples of Alk$^3$ chains include —CH$_2$—, —CH$_2$CH$_2$—, —CH$_2$CH$_2$CH$_2$— and —CH(CH$_3$)CH$_2$— chains.

When $R^5$, $R^6$, $R^7$ and/or $R^8$ is present as a $C_{3-8}$cycloalkyl group it may be for example a cyclopropyl, cyclobutyl, cyclopentyl or cyclohexyl group. Optional substituents which may be present on such groups include for example one, two or three substituents which may be the same or different selected from halogen atoms, for example fluorine, chlorine, bromine or iodine atoms, or hydroxy or $C_{1-6}$alkoxy, e.g. methoxy, ethoxy or i-propoxy groups.

When the groups $R^6$ and $R^7$ or $R^7$ and $R^8$ are both alkyl groups these groups may be joined, together with the N atom to which they are attached, to form a heterocyclic ring. Such heterocyclic rings may be optionally interrupted by a further heteroatom or heteroatom containing group selected from —O—, —S—, —N(R$^7$)—, —C(O)— or —C(S)— groups. Particular examples of such heterocyclic rings include piperidinyl, pyrazolidinyl, morpholinyl, thiomorpholinyl, pyrrolidinyl, imidazolidinyl and piperazinyl rings.

When $R^5$ is an optionally substituted aromatic or heteroaromatic group it may be any such group as described hereinafter in relation to $Cy^1$.

Additionally, when the group $Cy^1$ is a heterocycloaliphatic or heteropolycycloaliphatic group containing one or more nitrogen atoms each nitrogen atom may be optionally substituted by a group -(L$^5$)$_p$(Alk$^4$)$_q$R$^9$ in which $L^5$ is a —C(O)—, —C(O)O—, —C(S)—, —S(O)$_2$—, —CON(R$^6$)— or —SO$_2$N(R$^6$)— group; p is zero or the integer 1; Alk$^4$ is an optionally substituted aliphatic or heteroaliphatic chain; q is zero or the integer 1; and $R^9$ is a hydrogen atom or an optionally substituted cycloaliphatic, heterocycloaliphatic, polycycloaliphatic, heteropolycycloaliphatic, aromatic or heteroaromatic group as herein described in relation to $Cy^1$. Optional substituents include those described previously in relation to heterocycloaliphatic groups.

When Alk$^4$ is present as an aliphatic or heteroaliphatic chain it may be for example any aliphatic or heteroaliphatic chain as hereinbefore described for Alk$^1$.

In general, optionally substituted aromatic groups represented by the groups $Cy^1$ include for example monocyclic or bicyclic fused ring $C_{6-12}$aromatic groups, such as phenyl, 1- or 2-napthyl, 1- or 2-tetrahydronapthyl, indanyl or indenyl groups.

Heteroaromatic groups represented by the groups $Cy^1$ include for example $C_{1-9}$heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—C$_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,5-oxadiazolyl, 1,3,4-oxadiazolyl, 1,3,4-thiadiazolyl, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, [2,3-dihydro]benzothienyl, benzotriazolyl, indolyl, indolinyl, indazolinyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, quinoxalinyl, naphthyridinyl, imidazo[1,5-a]pyridinyl, imidazo[1,5-a]pyrazinyl, imidazo[1,5-c]pyrimidinyl, pyrido[3,4-b]pyridyl, pyrido[3,2-b]pyridyl, pyrido[4,3-b]pyridyl, quinolinyl, isoquinolinyl, phthalazinyl, tetrazolyl, 5,6,7,8-tetrahydroquinolinyl, 5,6,7,8-tetrahydroisoquinolinyl, imidyl, e.g. succinimidyl, phthalimidyl or naphthalimidyl such as 1,8-naphthalimidyl, pyrazolo[4,3-d]pyrimidinyl, furo[3,2-d]pyrimidinyl, thieno[3,2-d]pyrimidinyl, pyrrolo[3,2-d]pyrimidinyl, pyrazolo[3,2-b]pyridinyl, furo[3,2-b]pyridinyl, thieno[3,2-b]pyridinyl, pyrrolo[3,2-b]pyridinyl, thiazolo[3,2-a]pyridinyl, pyrido[1,2-a]pyrimidinyl, tetrahydroimidazo[1,2-a]pyrimidinyl and dihydroimidazo[1,2-a]pyrimidinyl groups.

Optional substituents which may be present on aromatic or heteroaromatic groups represented by the group $Cy^1$ include one, two, three or more substituents, each selected from an atom or group $R^{10}$ in which $R^{10}$ is $R^{10a}$ or $-L^6Alk^5(R^{10a})_r$, where $R^{10a}$ is a halogen atom, or an amino ($-NH_2$), substituted amino, nitro, cyano, hydroxyl ($-OH$), substituted hydroxyl, formyl, carboxyl ($-CO_2H$), esterified carboxyl, thiol ($-SH$), substituted thiol, $-COR^{11}$ [where $R^{11}$ is an $-L^6Alk^3(R^{10a})_r$, aryl or heteroaryl group], $-CSR^{11}$, $-SO_3H$, $-SOR^{11}$, $-SO_2R^{11}$, $-SO_3R^{11}$, $-SO_2NH_2$, $-SO_2NHR^{11}$, $-SO_2N(R^{11})_2$, $-CONH_2$, $-CSNH_2$, $-CONHR^{11}$, $-CSNHR^{11}$, $-CON(R^{11})_2$, $-CSN(R^{11})_2$, $-N(R^{12})SO_2R^{11}$ [where $R^{12}$ is a hydrogen atom or a straight or branched alkyl group], $-N(SO_2R^{11})_2$, $-N(R^{12})SO_2NH_2$, $-N(R^{12})SO_2NHR^{11}$, $-N(R^{12})SO_2N(R^{11})_2$, $-N(R^{12})COR^{11}$, $-N(R^{12})CONH_2$, $-N(R^{12})CONHR^{11}$, $-N(R^{12})CON(R^{11})_2$, $-N(R^{12})CSNH_2$, $-N(R^{12})CSNHR^{11}$, $-N(R^{12})CSN(R^{11})_2$, $-N(R^{12})CSR^{11}$, $-N(R^{12})C(O)OR^{11}$, $-C=NR^{12}(NR^{12})$, $-SO_2NHet^1$ [where $-NHet^1$ is an optionally substituted $C_{3-7}$cyclicamino group optionally containing one or more other $-O-$ or $-S-$ atoms or $-N(R^{12})-$, $-C(O)-$ or $-C(S)-$ groups], $-CONHet^1$, $-CSNHet^1$, $-N(R^{12})SO_2NHet^1$, $-N(R^{12})CONHet^1$, $-N(R^{12})CSNHet^1$, $-SO_2N(R^{12})Het$ [where -Het is an optionally substituted monocyclic $C_{3-7}$carbocyclic group optionally containing one or more other $-O-$ or $-S-$ atoms or $-N(R^{12})-$, $-C(O)-$, $-S(O)-$ or $-S(O)_2-$ groups], -Het, $-CON(R^{12})Het$, $-CSN(R^{12})Het$, $-N(R^{12})CON(R^{12})Het$, $-N(R^{12})CSN(R^{12})Het$, $-N(R^{12})SO_2N(R^{12})Het$, aryl or heteroaryl groups; $L^6$ is a covalent bond or a linker atom or group as hereinbefore defined for $L^2$; $Alk^5$ is an optionally substituted straight or branched $C_{1-6}$alkylene, $C_{2-6}$alkenylene or $C_{2-6}$alkynylene chain, optionally interrupted by one, two or three $-O-$ or $-S$-atoms or $-S(O)_n-$ [where n is an integer 1 or 2] or $-N(R^{12})-$ e.g. $-N(CH_3)-$ groups; and r is zero or the integer 1, 2, or 3. It will be appreciated that when two $R^{11}$ or $R^{12}$ groups are present in one of the above substituents the $R^{11}$ and $R^{12}$ groups may be the same or different.

When in the group $-L^6Alk^5(R^{10a})_r$ r is an integer 1, 2 or 3, it is to be understood that the substituent or substituents $R^{10a}$ may be present on any suitable carbon atom in -$Alk^5$. Where more than one $R^{10a}$ substituent is present these may be the same or different and may be present on the same or different atom in -$Alk^5$. Clearly, when r is zero and no substituent $R^{10a}$ is present the alkylene, alkenylene or alkynylene chain represented by $Alk^5$ becomes an alkyl, alkenyl or alkynyl group.

When $R^{10a}$ is a substituted amino group it may be for example a group $-NHR^{11}$ [where $R^{11}$ is as defined above] or a group $-N(R^{11})_2$ wherein each $R^{11}$ group is the same or different.

When $R^{10}$ is a halogen atom it may be for example a fluorine, chlorine, bromine, or iodine atom.

When $R^{10a}$ is a substituted hydroxyl or substituted thiol group it may be for example a group $-OR^{11}$ or a $-SR^{12}$ group respectively.

Esterified carboxyl groups represented by the group $R^{10a}$ include groups of formula $-CO_2Alk^6$ wherein $Alk^6$ is a straight or branched, optionally substituted $C_{1-8}$alkyl group such as a methyl, ethyl, n-propyl, i-propyl, n-butyl, i-butyl, s-butyl or t-butyl group; a $C_{5-12}$aryl$C_{1-8}$alkyl group such as an optionally substituted benzyl, phenylethyl, phenylpropyl, 1-naphthylmethyl or 2-naphthylmethyl group; a $C_{1-12}$aryl group such as an optionally substituted phenyl, 1-naphthyl or 2-naphthyl group; a $C_{6-2}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^6$ group include $R^{10a}$ atoms and groups as described above.

When $Alk^5$ is present in or as a substituent it may be for example a $-CH_2$, $-CH(CH_3)$, $-C(CH_3)_2$, $-CH_2CH_2-$, $-CH_2CH_2CH-$, $-CH(CH_3)CH_2-$, $-CH_2CH_2CH_2CH_2$, $-CH_2CH(CH_3)CH_2$, $-CH(CH_3)CH_2CH_2-$, $-C(CH_3)_2CH_2-$, $-CH=CH-$, $-CH=CCH_2$, $-CH_2C=CH-$, $-CH=CHCH_2CH_2-$, $-CH_2CH=CHCH_2-$, $-CH_2CH_2CH=CH_2-$, $-CC-$, $-CCCH_2$, $-CH_2CC-$, $-CCCH_2CH_2-$, $-CH_2CCCH_2-$ or $-CH_2CH_2CC-$ chain, optionally interrupted by one, two, or three $-O-$ or $-S-$, atoms or $-S(O)-$, $-S(O)_2-$ or $-N(R^{12})-$, e.g. $-N(CH_3)-$ groups. The aliphatic chains represented by $Alk^5$ may be optionally substituted by one, two or three halogen atoms in addition to any $R^{10a}$ groups that may be present.

Aryl or heteroaryl groups represented by the groups $R^{10a}$ or $R^{11}$ include mono- or bicyclic optionally substituted $C_{6-12}$ aromatic or $C_{1-9}$ heteroaromatic groups as described above for the group $Cy^1$. The aromatic and heteroaromatic groups may be attached to the group $Cy^1$ in compounds of formula (1) by any carbon or hetero e.g. nitrogen atom as appropriate.

It will be appreciated that when $-NHet^1$ or -Het forms part of a substituent $R^{10}$ the heteroatoms or heteroatom containing groups that may be present within the ring $-NHet^1$ or -Het take the place of carbon atoms within the parent carbocyclic ring.

Thus when $-NHet^1$ or -Het forms part of a substituent $R^{10}$ each may be for example an optionally substituted pyrrolidinyl, imidazolidinyl, pyrazolidinyl, piperazinyl, morpholinyl, thiomorpholinyl, piperidinyl or thiazolidinyl group. Additionally Het may represent for example, an optionally substituted cyclopentyl or cyclohexyl group. Optional substituents which may be present on $-NHet^1$ include those substituents described above when $Cy^1$ is a heterocycloaliphatic group.

Particularly useful atoms or groups represented by $R^{10}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimindinyl, pyrrolyl, furyl, thiazolyl, or thienyl, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxy-propylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{3-7}$cycloalkyl, e.g. cyclobutyl, cyclopentyl, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino, ethylamino, $-CH(CH_3)NH_2$ or $-C(CH_3)_2NH_2$, halo$C_{1-6}$alkylamino, e.g. fluoro$C_{1-6}$alkylamino, e.g. $-CH(CF_3)NH_2$ or $-C(CF_3)_2NH_2$, amino ($-NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, imido, such as phthalimido or naphthalimido, e.g. 1,8-naphthalimido, nitro, cyano, hydroxyl ($-OH$), formyl [$HC(O)-$], carboxyl ($-CO_2H$), $-CO_2Alk^6$ [where $Alk^6$ is as defined above], $C_{1-6}$ alkanoyl e.g. acetyl, optionally substituted benzoyl, thiol ($-SH$), thioC$_{1-6}$alkyl, e.g. thiomethyl or thioethyl, sulphonyl (—SO$_3$H), C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylamino-carbonyl, C$_{1-6}$dialkylaminoC$_{1-6}$alkylaminocarbonyl, e.g. diethylaminoethyl-aminocarbonyl, aminocarbonylamino, C$_{1-6}$alkylaminocarbonylamino, e.g. methylaminocarbonylamino or ethylaminocarbonylamino, C$_{1-6}$dialkylamino-carbonylamino, e.g. dimethylaminocarbonylamino or diethylaminocarbonylamino, C$_{1-6}$alkylaminocabonylC$_{1-6}$alkylamino, e.g. methylamino-carbonylmethylamino, aminothiocarbonylamino, C$_{1-6}$alkylaminothiocarbonyl-amino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, —CONHC(=NH)NH$_2$, C$_{1-6}$alkylsulphonyl-amino, e.g. methylsulphonylamino or ethylsulphonylamino, C$_{1-6}$dialkyl-sulphonylamino, e.g. dimethylsulphonylamino or diethylsulphonylamino, optionally substituted phenylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, optionally substituted morpholinesulphonylamino or morpholinesulphonylC$_{1-6}$alkylamino, optionally substituted phenylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoyl-amino, e.g. dimethylaminoacetylamino, C$_{1-6}$alkanoylaminoC$_{1-6}$alkyl, e.g. acetylaminomethyl, C$_{1-6}$alkanoylaminoC$_{1-6}$alkylamino, e.g. acetamidoethyl-amino, C$_{1-6}$alkoxycarbonylamino, e.g. methoxycarbonylamino, ethoxycarbonyl-amino or t-butoxycarbonylamino or optionally substituted benzyloxy, pyridylmethoxy, thiazolylmethoxy, benzyloxycarbonylamino, benzyloxy-carbonylaminoC$_{1-6}$alkyl e.g. benzyloxycarbonylaminoethyl, benzothio, pyridyl-methylthio or thiazolylmethylthio groups.

A further particularly useful group of substituents represented by R$^{10}$ when present on aromatic or heteroaromatic groups includes substituents of formula -L$^6$Alk$^6$R$^{10a}$ where L$^6$ is preferably a covalent bond or an —O— or —S— atom or —N(R$^3$)—, —C(O)—, —C(O)O—, —O—C(O)—, —N(R$^3$)CO—, —CON(R$^3$)— or —N(R$^3$)S(O)$_2$-group, Alk$^5$ is an optionally substituted C$_{1-8}$alkyl group optionally interrupted by one or two —O— or —S— atoms or —N(R$^{12}$)—, —C(O)—, —C(S)—, —CON(R$^{12}$)— or —N(R$^{12}$)CO— groups and Rica is an optionally substituted Het group as herein defined or an optionally substituted aromatic or heteroaromatic group as hereinbefore described in relation to Cy$^1$.

Where desired, two R$^{10}$ substituents may be linked together to form a cyclic group such as a cyclic ether, e.g. a C$_{1-6}$alkylenedioxy group such as methylenedioxy or ethylenedioxy.

It will be appreciated that where two or more R$^{10}$ substituents are present, these need not necessarily be the same atoms and/or groups. In general, the substituent(s) may be present at any available ring position on the aromatic or heteroaromatic group represented by the group Cy$^1$.

The substituted aromatic or heteroaromatic group represented by Ar in compounds of the invention may be any aromatic or heteroaromatic group as hereinbefore described for Cy$^1$. Optional substituents which may be present include those R$^{10}$ atoms and groups as generally or particularly described in relation to Cy$^1$ aromatic and heteroaromatic groups.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulfonates, e.g. methanesulfonates, ethanesulfonates, or isothionates, arylsulfonates, e.g. p-toluenesulfonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In compounds of formula (1) R is preferably a hydrogen atom.

In compounds of this type and in general in compounds of formula (1) X is preferably an —O— or —S— atom, and is especially a —S— atom.

In general in compounds of formula (1) R$^a$ is preferably a hydrogen atom or a C$_{1-4}$alkyl group, especially a methyl, ethyl, n-propyl or i-propyl group. In particular R$^a$ is a methyl group or more especially a hydrogen atom.

In another particular class of compounds of formula (1) the bond represented by the dashed line is present and A is a —C(R$^b$)= group. In these compounds R$^b$ is preferably a hydrogen atom or a C$_{1-4}$alkyl group, especially a methyl, ethyl, n-propyl or i-propyl group. More particularly R$^b$ is a methyl group or more especially a hydrogen atom.

When in compounds of formula (1) n is the integer 1, Alk$^1$ is preferably an optionally substituted C$_{1-6}$alkylene chain, especially an optionally substituted —CH$_2$—, —CH$_2$CH$_2$—, —CH$_2$CH$_2$CH$_2$—, —CH(CH$_3$)CH$_2$— or —CH$_2$CH(CH$_3$)— chain, most especially a —CH$_2$— or —CH$_2$CH$_2$— chain.

In one class of compounds of formula (1) n is zero.

The group L$^1$ in compounds of formula (1) is preferably a covalent bond or an —O— or —S— atom or an —N(R$^3$)—, especially —NH— or —N(CH$_3$)—, —C(O)—, —C(S)—, —S(O)— or —S(O)$_2$— group. More particularly L$^1$ is a covalent bond or an —O— or —S— atom or —NH— group. La is more especially preferably is a covalent bond.

Cy$^1$ in compounds of formula (1) is preferably an optionally substituted cycloaliphatic, aromatic or heteroaromatic group as hereinbefore generally and particularly defined.

Particularly preferred Cy$^1$ optionally substituted cycloaliphatic groups include optionally substituted C$_{3-7}$cycloalkyl groups, especially cyclopropyl, cyclobutyl, cyclopentyl or cyclohexyl groups. Cy$^1$ is in particular a cyclopropyl group.

Each of these preferred Cy$^1$ cycloalkyl groups may be unsubstituted. When substituents are present these may in particular include halogen atoms, especially fluorine, chlorine or bromine atoms, or C$_{1-6}$alkyl groups, especially $C_{1-3}$alkyl groups, most especially a methyl group, or a halo$C_{1-6}$alkyl group, especially a fluoro$C_{1-6}$alkyl group, most especially a —$CF_3$ group, or a $C_{1-6}$alkoxy, especially methoxy, ethoxy, propoxy or i-propoxy group, or a halo$C_{1-6}$alkoxy, especially a fluoro$C_{1-6}$alkoxy, most especially a —$OCF_3$ group, or a cyano (—CN), esterified carboxyl, especially —$O_2CH_3$ or —$CO_2C(CH_3)_3$, nitro (—$NO_2$), amino (—$NH_2$), substituted amino, especially —$NHCH_3$ or —$N(CH_3)_2$, —$C(O)R^6$, especially —$C(O)CH_3$, or —$N(R^6)C(O)R^7$, especially —$NHCOCH_3$ group.

Particularly preferred $Cy^1$ aromatic groups include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur or nitrogen atoms. Particularly preferred optionally substituted monocyclic heteroaromatic groups include optionally substituted furyl, thienyl, pyrrolyl, oxazolyl, thiazolyl, pyridyl, pyrimidinyl or triazinyl group. In a further preference, the heteroaromatic group may be an eight- to thirteen-membered bicyclic fused ring containing one or two oxygen, sulphur or nitrogen atoms. Particularly useful groups of this type include optionally substituted indolyl groups.

Particularly preferred optional substituents which may be present on $Cy^1$ aromatic or heteroaromatic groups include one, two or three atoms or groups —$R^{10a}$ or -$L^6Alk^5(R^{10a})_r$ as hereinbefore defined. Particularly useful optional substituents include halogen atoms, especially fluorine, chlorine or bromine atoms, or $C_{1-6}$alkyl groups, especially $C_{1-3}$alkyl groups, most especially a methyl group, or a halo$C_{1-6}$alkyl group, especially a fluoro$C_{1-6}$alkyl group, most especially a —$CF_3$ group, or a $C_{1-6}$alkoxy, especially methoxy, ethoxy, propoxy or i-propoxy group, or a halo$C_{1-6}$alkoxy, especially a fluoro$C_{1-6}$alkoxy, most especially a —$OCF_3$ group, or a cyano (—CN), carboxyl (—$CO_2H$), esterified carboxyl (—$CO_2Alk^6$), especially —$CO_2CH_3$, —$CO_2CH_2CH_3$, or —$CO_2C(CH_3)_3$, nitro (—$NO_2$), amino (—$NH_2$), substituted amino, especially —$NHCH_3$ or —$N(CH_3)_2$, —$COR^{11}$, especially —$COCH_3$, or —$N(R^{12})COR^{11}$, especially —$NHCOCH_3$ group.

Further preferred optional substituents which may be present on $Cy^1$ aromatic or heteroaromatic groups include groups of formula -$L^6Alk^5(R^{10a})_r$ in which r is the integer 1 or 2, $L^6$ is a covalent bond or an —O— or —S— atom or a —$N(R^3)$—, especially —NH— or —$N(CH_3)$—, —C(O)—, —C(S)—, —C(O)O—, —OC(O)—, —$N(R^3)CO$—, especially —NHCO—, or —$CON(R^3)$—, especially —CHNH- group, $Alk^5$ is a $C_{1-6}$alkyl chain, especially a —$CH_2$—, —$CH_2CH_2$—, —$CH_2CH_2CH_2$— or —$CH_2CH_2CH_2CH_2$— chain and $R^{10a}$ is a hydroxyl or substituted hydroxyl group, especially a —$OCH_3$, —$OCH_2CH_3$ or —$OCH(CH_3)_2$ group or a —$NH_2$ or substituted amino group, especially a —$N(CH_3)_2$ or —$N(CH_2CH_3)_2$ group or a -Het group, especially an optionally substituted monocyclic $C_{5-7}$-carbocyclic group containing one, two or three —O—, —S—, —$N(R^{12})$—, especially —NH— or —$N(CH_3)$— or —C(O)— groups within the ring structure as previously described, most especially an optionally substituted pyrrolidinyl, imidazolidinyl, piperidinyl, e.g. N-methylpiperidinyl, morpholinyl, thiomorpholinyl or piperazinyl group or $R^{10a}$ is an optionally substituted heteroaromatic group, especially a five- or six-membered monocyclic heteroaromatic group containing one, two, three or four heteroatoms selected from oxygen, sulphur or nitrogen atoms, such as optionally substituted pyrrolyl, furyl, thienyl, imidazolyl, triazolyl, pyridyl, pyrimidinyl, triazinyl, pyridazinyl, or pyrazinyl group. Particularly preferred optional substituents on the -Het groups just described include hydroxyl (—OH) and carboxyl (—$CO_2H$) groups or those preferred optional substituents just described in relation to the group $Cy^1$, especially when $Cy^1$ is a cycloalkyl group.

In one particularly preferred group of compounds of formula (1) $Cy^1$ is an optionally substituted phenyl group, especially a phenyl group optionally substituted by one, two or three substituents where at least one, and preferably two substituents are located ortho to the bond joining $Cy^1$ to the remainder of the compound of formula (1). Particularly preferred ortho substituents include halogen atoms, especially fluorine or chlorine atoms, or $C_{1-3}$alkyl groups, especially methyl groups, $C_{1-3}$alkoxy groups, especially methoxy, halo$C_{1-3}$alkyl groups, especially —$CF_3$, halo$C_{1-3}$alkoxy groups, especially —$OCF_3$, or cyano (—CN), groups. In this class of compounds a second or third optional substituent when present in a position other than the ortho positions of the ring $Cy^1$ may be preferably an atom or group —$R^{10a}$ or -$L^6Alk^5(R^{10a})_r$ as herein generally and particularly described. In another preference, the $Cy^1$ phenyl group may have a substituent para to the bond joining $Cy^1$ to the remainder of the compound of formula (1). Particular para substituents include those particularly preferred ortho substituents just described. Where desired, the para substituent may be present with other ortho or meta substituents as just mentioned.

The group Y in compounds of formula (1) is preferably a —CH= group or a substituted carbon atom. Particular substituted carbon atoms include those where Y is —$C(R^{10})$= wherein $R^{10}$ is as generally or particularly described above, especially those —$R^{10a}$ and -$L^6Alk^6(R^{10a})_r$ substituents just described with respect to those preferred optional substituents present on $Cy^1$ aromatic or heteroaromatic groups. Particularly useful $R^{10}$ groups include —ON, —$X^1NH_2$, (where $X^1$ is a —C(O)— or —$S(O)_2$— group), —$X^1NHR^{11}$, —$X^1N(R^{11})_2$, —$X^1NHet^1$, —$X^1N(R^{12})Het$, —$X^1N(R^{12})Alk^5Het$, —$COR^{11}$, —$C=NR^{12}(NR^{12})$ or esterified carboxyl groups as described previously in relation to $Cy^1$ aromatic or heteroaromatic groups. Particularly useful compounds of formula (1) are those compounds wherein Y is —CH= or —$C(R^{10})$= in which $R^{10}$ is a CN, —$CONH_2$, —$CONHR^{11}$, —$CON(R^{11})_2$, —$CONHet^1$, —$CON(R^{12})Het$, —$CON(R^{12})Alk^5Het$, or esterified carboxyl, particularly —$CO_2Alk^5$ group as generally or particularly described herein.

Particularly preferred Ar aromatic groups in compounds of formula (1) include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur or nitrogen atoms. Particularly preferred optionally substituted monocyclic heteroaromatic groups include optionally substituted furyl, thienyl, pyrrolyl, oxazolyl, thiazolyl, pyridyl, pyrimidinyl or triazinyl group.

Particularly preferred optional substituents which may be present on Ar aromatic or heteroaromatic groups include atoms or groups —$R^{10a}$ or -$L^6Alk^6(R^{10a})_r$ as hereinbefore defined. Particularly useful optional substituents include halogen atoms, especially fluorine, chlorine or bromine atoms, or $C_{1-6}$alkyl groups, especially $C_{1-3}$alkyl groups, most especially a methyl group, or a halo$C_{1-6}$alkyl group, especially a fluoro$C_{1-6}$alkyl group, most especially a —$CF_3$ group, or a $C_{1-6}$alkoxy, especially methoxy, ethoxy, propoxy or i-propoxy group, or a halo$C_{1-6}$alkoxy, especially a fluoro$C_{1-6}$alkoxy, most especially a —$OCF_3$ group, or a cyano (—CN), esterified carboxyl, especially —$CO_2CH_3$ or —$CO_2C(CH_3)_3$, nitro (—$NO_2$), amino (—$NH_2$), substituted amino, especially —$NHCH_3$ or —$N(CH_3)_2$, —$COR^{11}$, especially —$COCH_3$, or —$N(R^{12})COR^{11}$, especially —$NHCOCH_3$ group.

Particularly useful Ar groups in compounds of formula (1) include phenyl and mono- or disubstituted phenyl groups in which each substituent is in particular a —$R^{10a}$ or -$L^6Alk^5$ $(R^{10a})_r$ atom or group as just defined and is especially a halogen atom or a $C_{1-3}$alkyl, $C_{1-3}$alkoxy or —CN group Particularly useful compounds of the invention include each of the compounds described in the Examples hereinafter, and the salts, solvates, hydrates and N-oxides thereof.

Compounds according to the invention are potent and selective inhibitors of p38 kinases, including all isoforms and splice variants thereof. More specifically the compounds of the invention are inhibitors of p38α, p38β and p38β2. The ability of the compounds to act in this way may be simply determined by employing tests such as those described in the Examples hereinafter.

The compounds of formula (1) are of use in modulating the activity of p38 kinases and in particular are of use in the prophylaxis and treatment of any p38 kinase mediated diseases or disorders in a human, or other mammal. The invention extends to such a use and to the use of the compounds for the manufacture of a medicament for treating such diseases or disorders. Further the invention extends to the administration to a human an effective amount of a p38 inhibitor for treating any such disease or disorder.

The invention also extends to the prophylaxis or treatment of any disease or disorder in which p38 kinase plays a role including conditions caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further the invention extends to the administration to a human an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation and conditions associated with prostaglandin endoperoxidase synthetase-2 (COX-2).

Autoimmune diseases which may be prevented or treated include but are not limited to rheumatoid arthritis, inflammatory bowel disease, ulcerative colitis, Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs, host disease or psoriasis.

The invention further extends to the particular autoimmune disease rheumatoid arthritis.

Inflammatory diseases which may be prevented or treated include but are not limited to asthma, allergies, respiratory distress syndrome or acute or chronic pancreatitis.

Destructive bone disorders which may be prevented or treated include but are not limited to osteoporosis, osteoarthritis and multiple myeloma-related bone disorder.

Proliferative diseases which may be prevented or treated include but are not limited to acute or chronic myelogenous leukemia, Kaposi's sarcoma, metastic melanoma and multiple myeloma.

Neurodegenerative diseases which may be prevented or treated include but are not limited to Parkinson's disease, Alzheimer's disease, cerebral ischemias or neurodegenerative disease caused by traumatic injury.

Viral diseases which may be prevented or treated include but are not limited to acute hepatitis infection (including hepatitis A, hepatitis B and hepatitis C), HIV infection and CMV retinitis.

Infectious diseases which may be prevented or treated include but are not limited to septic shock, sepsis and Shigellosis.

In addition, p38 inhibitors of this invention also exhibit inhibition of expression of inducible pro-inflammatory proteins such as prostaglandin endoperoxidase synthetase-2, otherwise known as cyclooxygenase-2 (COX-2) and are therefore of use in therapy. Pro-inflammatory mediators of the cyclooxygenase pathway derived from arachidonic acid are produced by inducible COX-2 enzyme. Regulation of COX-2 would regulate these pro-inflammatory mediators such as prostaglandins, which affect a wide variety of cells and are important and critical inflammatory mediators of a wide variety of disease states and conditions. In particular these inflammatory mediators have been implicated in pain, such as in the sensitization of pain receptors, or edema. Accordingly additional p38 mediated conditions which may be prevented or treated include edema, analgesia, fever and pain such as neuromuscular pain, headache, dental pain, arthritis pain and pain caused by cancer.

As a result of their p38 inhibitory activity, compounds of the invention have utility in the prevention and treatment of diseases associated with cytokine production including but not limited to those diseases associated with TNF, IL-1, IL-6 and IL-8 production.

Thus TNF mediated diseases or conditions include for example rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoiosis, bone resportion disease, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis, pyresis, viral infections such as HIV, CMV, influenza and herpes; and vetinary viral infections, such as lentivirus infections, including but not limited to equine infectious anemia virus, caprine arthritis virus, visna virus or maedi virus; or retrovirus infections, including feline immunodeficiency virus, bovine immunodeficiency virus or canine immunodeficiency virus.

Compounds of the invention may also be used in the treatment of viral infections, where such viruses elicit TNF production in vivo or are sensitive to upregulation by TNF. Such viruses include those that produce TNF as a result of infection and those that are sensitive to inhibition, for instance as a result of decreased replication, directly or indirectly by the TNF inhibiting compounds of the invention. Such viruses include, but are not limited to, HIV-1, HIV-2 and HIV-3, Cytomegalovirus (CMV), Influenza, adenovirus and the Herpes group of viruses such as Herpes Zoster and Herpes Simplex.

IL-1 mediated diseases or conditions include for example rheumatoid arthritis, osteoarthritis, psoriatic arthritis, traumatic arthritis, rubella arthritis, inflammatory bowel disease, stroke, endotoxemia and/or toxic shock syndrome, inflammatory reaction induced by endotoxin, diabetes, pancreatic β-cell disease, Alzheimer's disease, tuberculosis, atherosclerosis, muscle degeneration and cachexia.

IL-8 mediated diseases and conditions include for example those characterized by massive neutrophil infiltration such as psoriasis, inflammatory bowel disease, asthma, cardiac, brain and renal reperfusion injury, adult respiratory distress syndrome, thrombosis and glomerulonephritis. The increased IL-8 production associated with each of these diseases is responsible for the chemotaxis of neutrophils into inflammatory sites. This is due to the unique property of IL-8 (in comparison to TNF, IL-1 and IL-6) of promoting neutrophil chemotaxis and activation. Therefore, inhibition of IL-8 production would lead to a direct reduction in neutrophil infiltration.

It is also known that both IL-6 and IL-8 are produced during rhinovirus (HRV) infections and contribute to the pathogenesis of the common cold and exacerbation of asthma associated with HRV infection [Turner et al., Clin. Infec. Dis., 1997, 26, 840; Grunberg et al, Am. J. Crit. Care Med. 1997, 155, 1362; Zhu et al, J. Clin. Invest. 1996, 97, 421]. It has also been demonstrated in vitro that infection of pulmonary epithelial cells (which represent the primary site of infection by HRV) with HRV results in production of IL-6 and IL-8 [Sabauste et al, J. Clin. Invest. 1995, 96, 549]. Therefore, p38 inhibitors of the invention may be used for the treatment or prophylaxis of the common cold or respiratory viral infection caused by human rhinovirus infection (HRV), other enteroviruses, coronavirus, influenza virus, parainfluenza virus, respiratory syncytial virus or adenovirus infection.

For the prophylaxis or treatment of a p38 or pro-inflammatory cytokine mediated disease the compounds according to the invention may be administered to a human or mammal as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds for use according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively the compounds for use according to the present invention may be formulated in a suitable lotion containing the active component suspended or dissolved in one or more pharmaceutically acceptable carriers. Particular carriers include, for example mineral oil, sorbitan monostearate, polysorbate 60, cetyl esters wax, cetearyl alcohol, benzyl alcohol, 2-octyldodecanol and water.

For ophthalmic administration the compounds for use according to the present invention may be conveniently formulated as microionized suspensions in isotonic, pH adjusted sterile saline, either with or without a preservative such as bactericidal or fungicidal agent, for example phenylmercuric nitrate, benzylalkonium chloride or chlorhexidine acetate. Alternatively for ophthalmic administration compounds may be formulated in an ointment such as petrolatum.

For rectal administration the compounds for use according to the present invention may be conveniently formulated as suppositories. These can be prepared by mixing the active component with a suitable non-irritating excipient which is solid at room temperature but liquid at rectal temperature and so will melt in the rectum to release the active component. Such materials include for example cocoa butter, beeswax and polyethylene glycols.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols Ar, $Cy^1$, $Alk^1$, n, $L^1$, R, $R^a$, $R^b$, $R^c$, A, X and Y when used in the formulae depicted are to be understood to represent those groups described above in relation to formulae (1a) and (1b) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups.

Thus according to a further aspect of the invention a compound of formula (1) in which A is a —$C(R^b)$= group, X is a —O— or —S— atom or —NH— group and Y is a substituted carbon atom in which the substituent is an esterified carboxyl group, for example a —$CO_2Alk^6$ group, may be prepared according to the reactions set out in Scheme 1 below. In the Scheme the preparation of an ethyl ester is specifically shown, but it will be appreciated that other esters may be obtained by simply varying the ester starting material and if appropriate any reaction conditions:

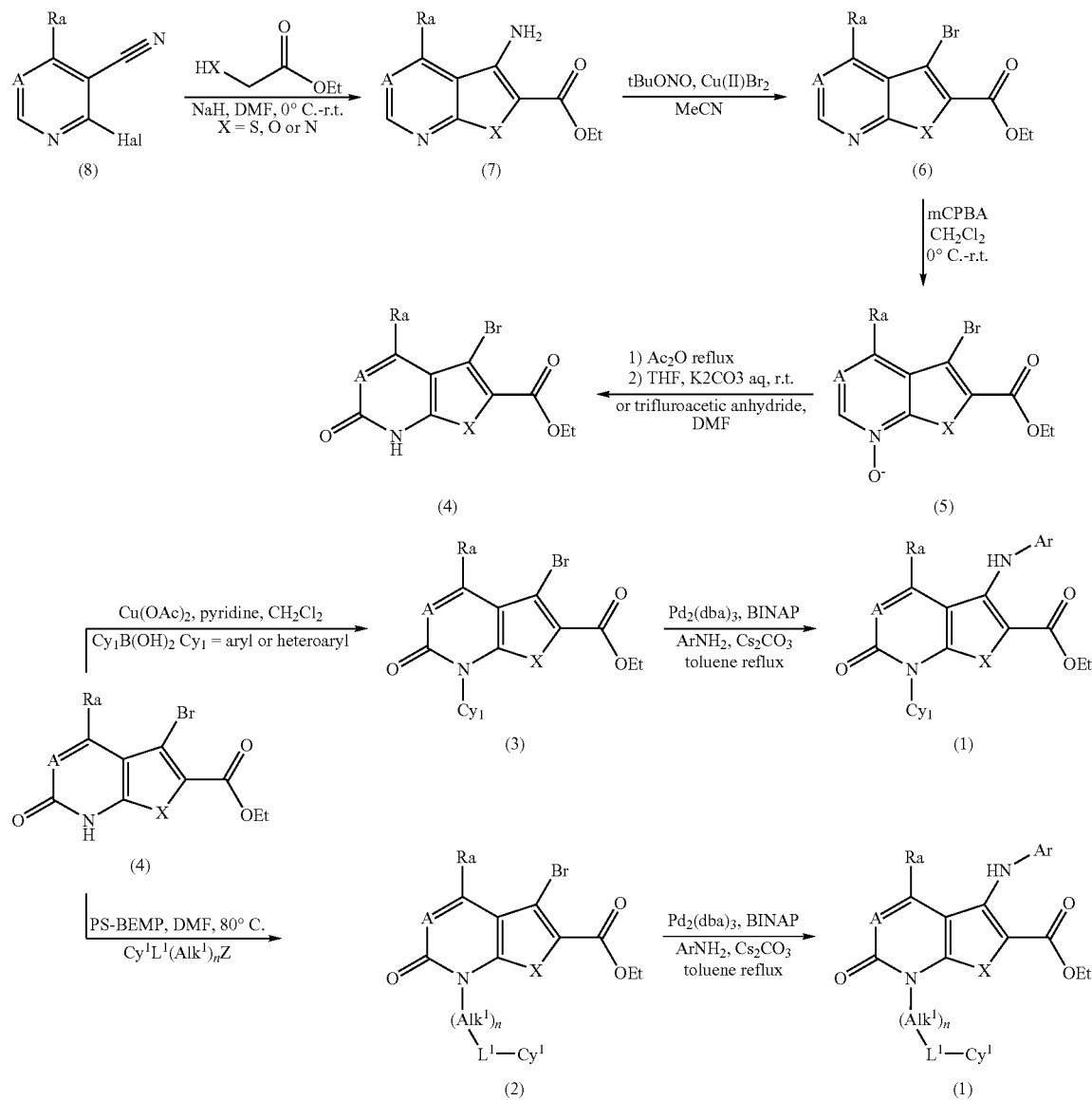

Scheme 1

Thus in Scheme 1 a compound of formula (1) may be prepared by reaction of a compound of formulae (2) or (3) with an amine ArNH$_2$ in the presence of a palladium catalyst. The reaction may be conveniently carried out in a solvent such as toluene at an elevated temperature, eg the reflux temperature, using a catalyst such as tris(dibenzylideneacetone)dipalladium(0), a phosphine ligand such as 2,2'-bis(diphenylphosphino)-1,1'-binaphthyl and a base such as caesium carbonate. Where desired, alternative reaction conditions may be used, for example as described in the literature [Luker et al. Tet. Lett. (2001) 41, 7731; Buchwald S. L. J. Org. Chem. (2000) δ 1144; Hartwig J. F. Angew. Chem. In. Ed. Engl. (1998) 37, 2046].

Intermediates of formula (2) may be prepared by reaction of a compound of formula (4) with an alkylating agent of formula Cy$^1$L$^1$(Alk$^1$)$_n$Z, where Z is a leaving group such as a halogen atom, e.g. a chlorine, bromine or iodine atom or a sulphonyloxy group such as an alkylsulphonyloxy e.g. trifluoromethylsulphonyloxy or arylsulphonyloxy e.g. phenylsulphonyloxy group.

The reaction may be performed in the presence of a solvent, for example a substituted amide such as dimethylformamide, optionally in the presence of a base, for example an inorganic base such as sodium hydride, or an organic base such as an organic amine, e.g. a cyclic amine such as 1,5-diazabicyclo[4.3.0]non-5-ene or a resin bound organic amine such as resin bound 2-tert-butylimino-2-diethylamino-1,3-dimethyl-perhydro-1,3,2-diazaphosphorine (PS-BEMP), at an elevated temperature, for example 80 to 100° C.

Intermediates of formula (3) may be prepared by the reaction of a compound of formula (4) with a boronic acid of formula Cy$^1$B(OH)$_2$ in which Cy$^1$ is an aryl or heteroaryl group. The reaction may be performed in an organic solvent, for example a halogenated hydrocarbon such as dichloromethane or dichloroethane in the presence of a copper reagent, for example a copper (I) salt such as CuI or for example a copper (II) reagent such as copper (II) acetate, optionally in the presence of an oxidant, for example 2,2,6,6-tetramethylpiperidine-1-oxide or pyridine-N-oxide, optionally in the presence of a base, for example an organic amine such as an alkylamine, e.g. triethylamine or an aromatic amine, e.g. pyridine at a temperature from around ambient to the reflux temperature [see for example Chan, D. T. et al Tetrahedron Letters, 1998, 2933; Lam, P. Y. S. et al, Tetrahedron Letters, 2001, 3415]

Intermediates of formula (3) where Cy$^1$ is an aryl or heteroaryl group may also be prepared by nucleophilic aromatic substitution of a suitably activated aryl or heteroaryl halide with a compound of formula (4). The reaction may be performed in a dialkylamide solvent such as dimethylformamide in the presence of a base such as a metal hydride e.g. sodium hydride at a temperature from around ambient to 100° C. Suitably activated aryl or heteroaryl halides are those with an electron withdrawing substituent such as a nitro, cyano or ester group e.g. a chloro- or fluoro-nitrobenzene or 2-chloro-5-nitropyridine. Alternatively a nitrogen containing heteroaryl halide can be activated to nucleophilic substitution by N-oxidation for example a halopyridine N-oxide such as a chloropyridine N-oxide e.g. 2-chloropyridine N-oxide.

It will be appreciated that if desired the reactions just described may be carried out in the reverse order so that the amination using ArNH$_2$ is performed first with the intermediate of formula (4) followed by alkylation/arylation to yield the compound of formula (1). It may be necessary to protect the nitrogen function of compounds of formula (4) during the course of these reactions. Such protection may be achieved by O-alkylation with an alkyl halide e.g. cyclopropylmethyl bromide or an arylalkyl bromide e.g. benzyl bromide as shown in Scheme 1a.

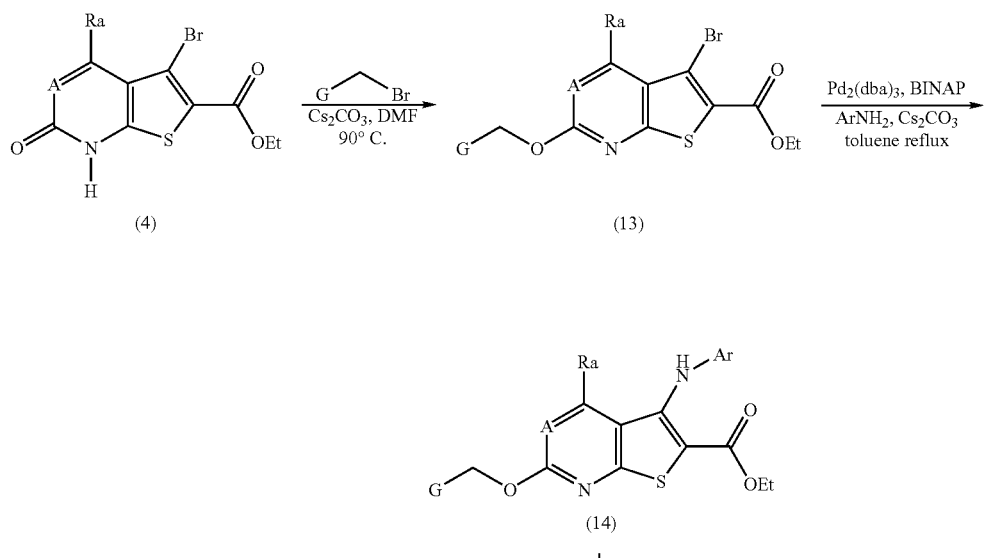

-continued

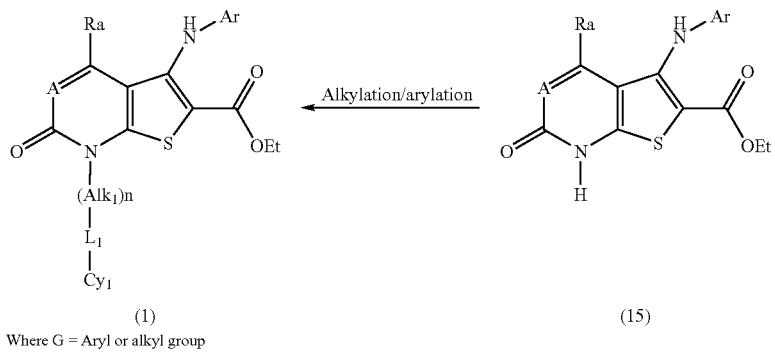

Where G = Aryl or alkyl group

The O-alkylation reaction may be performed in an organic solvent such as dimethylformamide in the presence of a base, for example an inorganic base such as $Cs_2CO_3$ or an organic base such as an amine e.g. a cyclic amine such as 1,5-diazabicyclo[4.3.0]non-5-ene at an elevated temperature e.g. 80° C. to 100° C. to give a compound of formula (13). Reaction of the protected compound (13) with $ArNH_2$ under palladium catalysis can then be performed as previously described to give a compound of formula (14). Deprotection can then be achieved by treating a solution of this compound in an alcohol e.g. methanol with a mineral acid such as concentrated HCl at an elevated temperature e.g. the reflux temperature to give a compound of formula (15). Alternatively when benzyl protection is employed then this group may be removed reductively by treating a solution of compound (14) in a solvent e.g. water or an organic solvent such as ethanol using a palladium or platinum catalyst e.g. palladium on carbon or $PtO_2$ under an elevated pressure of hydrogen at a temperature from around ambient to 60° C. Compounds of formula (15) can then undergo alkylation/arylation reactions as previously described to give compounds of formula (1).

Intermediate pyridinones of formula (4) may be prepared from pyridine N-oxides of formula (5) by sequential reaction with an anhydride, for example acetic anhydride at an elevated temperature, for example the reflux temperature followed by reaction with an inorganic base, for example a carbonate such as aqueous potassium carbonate in a solvent such as an ether for example a cyclic ether e.g. tetrahydrofuran at around ambient temperature. Alternatively the reaction may be performed using trifluoroacetic anhydride in dimethylformamide from 0° C. to ambient temperature conditions [see for example Konno et al., Heterocycles (1986) 24, 2169].

Pyridine N-oxides of formula (5) may be formed by oxidation of pyridines of formula (6) using an oxidising agent such as hydrogen peroxide in the presence of an acid such as acetic acid, at an elevated temperature, for example around 70° C. to 80° C., or alternatively by reaction with a peracid such as peracetic acid or m-chloroperoxybenzoic acid in a solvent, such as a halogenated hydrocarbon e.g. dichloromethane or an alcohol e.g. tert-butanol at a temperature from the ambient temperature to the reflux temperature.

Intermediate pyridines of formula (6) in Scheme 1 may be obtained by standard methods such as for example by the Sandmeyer reaction. Thus for example a bromide of formula (6) may be prepared by treatment of an aryl amine of formula (7) with an alkyl nitrite, for example t-butyl nitrite and a copper salt, for example copper (II) bromide in the presence of a solvent, for example a nitrile such as acetonitrile at a temperature from about 0° to around 65° C.

Amines of formula (7) may be formed from 2-halopyridine-3-carbonitriles of formula (8) by reaction with a reagent of formula $HXCH_2CO_2Et$ [where Et is an ethyl group and X is a —O— or —S— atom or —NH— group]. The reaction may be performed in the presence of a solvent such as a substituted amide for example dimethylformamide or an ether e.g. a cyclic ether such as tetrahydrofuran or alcohol such as ethanol in the presence of a base, for example an inorganic base such as sodium carbonate or a hydride e.g. sodium hydride or an organic base such as 1,5-diazabicyclo[4.3.0]non-5-ene or a trialkylamine such as triethylamine at a temperature between about 0° C. and 100° C. The carbonitrile starting materials are readily available or may be obtained from known compounds using standard procedures.

In another process according to the invention, a compound of formula (1) in which A is a —C($R^b$)═ group, X is a —O— or —S— atom or —NH— group and Y is a —C(CN)═ group may be prepared using the reactions set out in Scheme 2 below:

Scheme 2

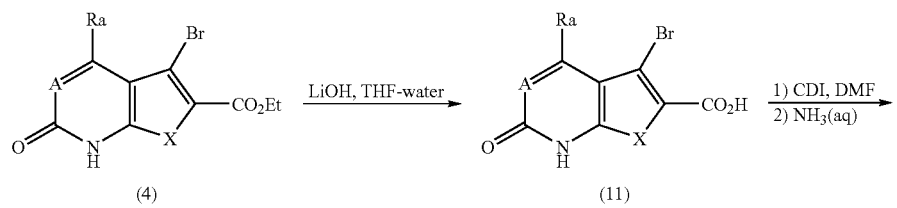

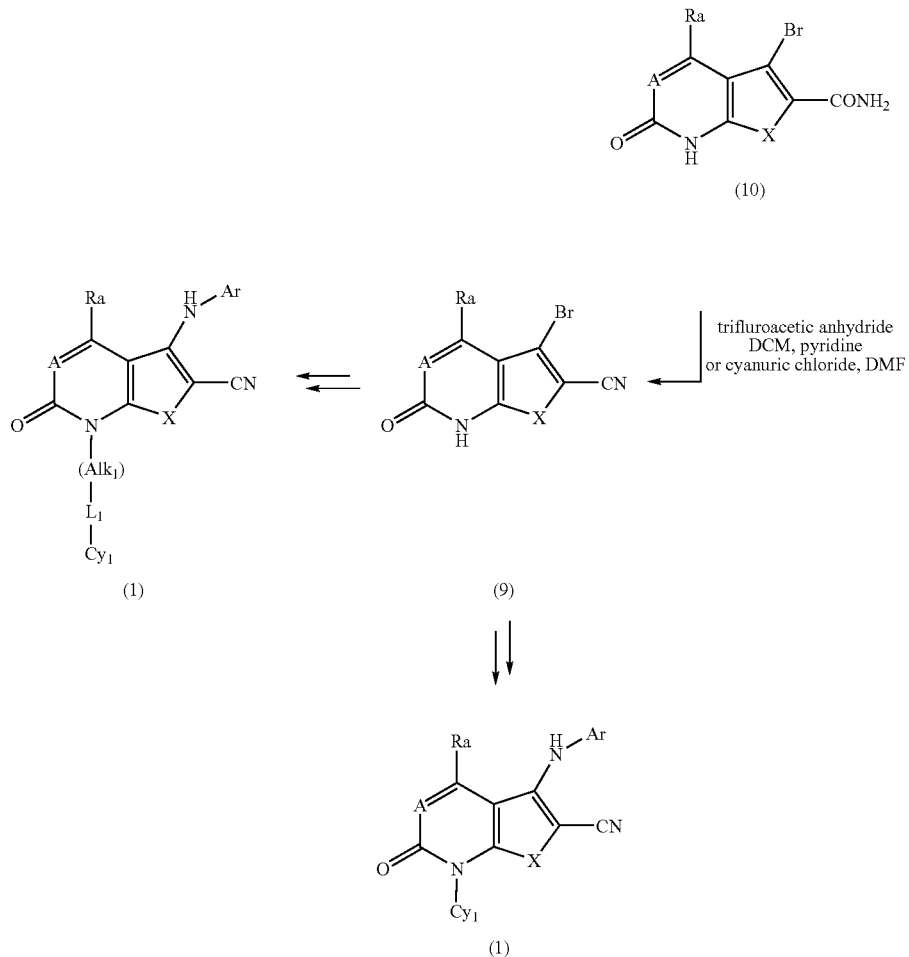

Thus in Scheme 2, a 2-cyano intermediate of formula (9) may be aminated and alkylated or arylated in a final step to yield a compound of the invention using the reactions and reagents described above in relation to the amination, alkylation and arylation of intermediates of formula (4). Nitriles of formula (9) may be obtained by dehydration of the corresponding amide of formula (10) using a dehydrating agent such as trifluoroacetic anhydride in the presence of a base such as pyridine in a solvent, for example a halogenated hydrocarbon such as dichloromethane at around ambient temperature. Alternatively, cyanuric chloride may be used in a solvent such as dimethylformamide at a temperature from around 0° C. to 110° C. Amides of formula (10) may be obtained from the corresponding acids of formula (11) using conventional procedures, for example by reaction with 1,1'-carbonyldiimidazole and aqueous ammonia in a solvent such as dimethyl formamide at ambient temperature. The intermediate acids of formula (11) may be prepared by hydrolysis of esters of formula (4) using a base such as lithium hydroxide in water and a solvent such as tetrahydrofuran.

In another process according to the invention, a compound of formula (1) in which A is a —C($R^b$)= group, X is a —O— or —S— atom, Y is a —C(CN)= group, Ar is a heteroaromatic group and $Alk^1$, L, n and $Cy^1$ are as previously defined, may be prepared by nucleophilic aromatic substitution of a suitably activated heteroaryl halide with a compound of formula (16). This reaction can be performed in an organic solvent such as an ether, e.g. tetrahydrofuran or dialkylamide e.g. dimethylformamide or a solvent such as dimethylsulphoxide in the presence of an inorganic base such as sodium hydride at an elevated temperature from 50-80° C. Suitably activated heteroaryl halides include halopyridines e.g. a chloropyridine such as 2,6-dichloropyridine or halopyridine N-oxides e.g. a chloropyridine N-oxide such as 2-chloro-6-methylpyridine N-oxide.

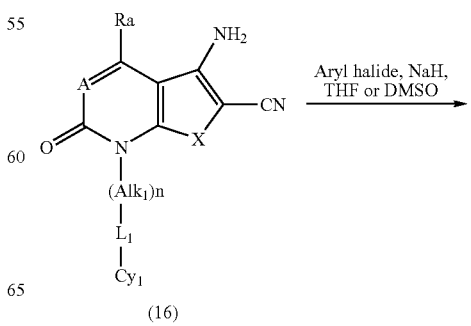

-continued

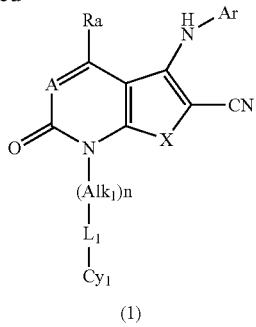

(1)

Amides of formula (1a) may be obtained from acids of formula (17) using conventional procedures such as those described in Scheme (4).

mide or an ether e.g. tetrahydrofuran or a halogenated hydrocarbon, e.g. dichloromethane at around ambient temperature to the reflux temperature. In another procedure reaction of an acid of formula (17) with 1-(3-dimethylaminopropyl)-3-ethylcarbodiimide and pentafluorophenol in a solvent such as an amide solvent e.g. DMF at around ambient temperature affords a pentafluorophenyl ester of formula (18). Amides of formula (1a) can then be prepared by reaction of this ester with amines of formula $HNR^{15}R^{15}$ or aqueous ammonia in a solvent such as a halogenated hydrocarbon e.g. dichloromethane at around ambient temperature. The intermediate acids of formula (17) may be prepared by hydrolysis of esters of formula (1) described in Scheme 1 using a base such as an alkali metal hydroxide e.g. sodium hydroxide or lithium hydroxide in water and a solvent such as tetrahydrofuran or alcohol such as ethanol from around ambient temperature to the reflux temperature.

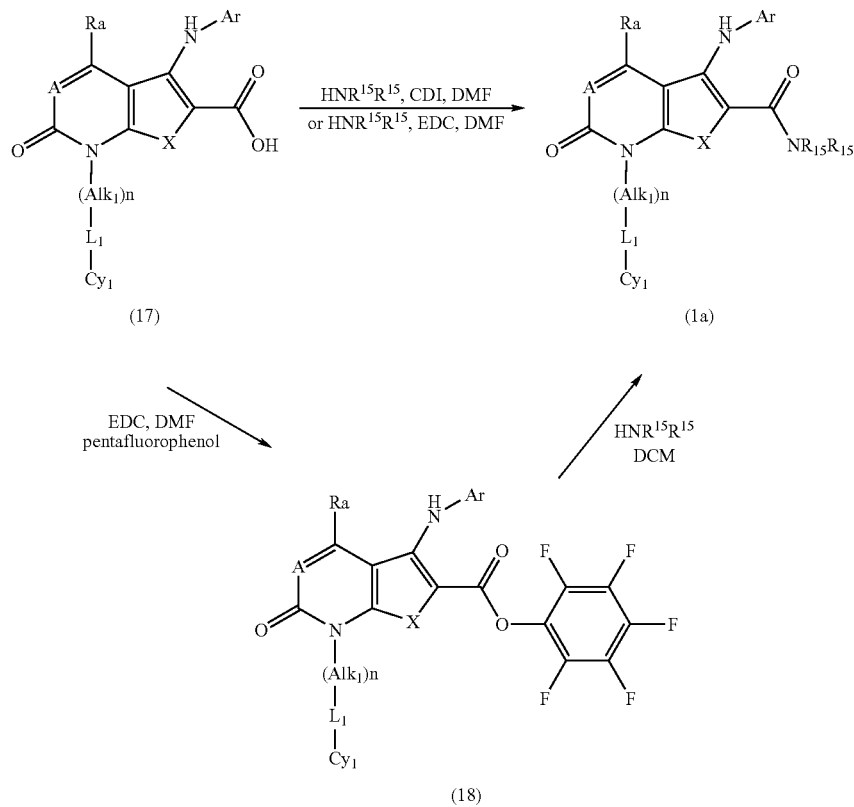

Scheme 4

Thus amides may be formed by reaction of the acid (17) with 1,1'-carbonyldiimidazole and an amine of formula $HNR^{15}R^{15}$ (where each $R^{15}$ is independently H or $R^{11}$ as previously described) or aqueous ammonia in a solvent e.g. an amide solvent such as dimethylformamide at around ambient temperature to 60° C. Alternatively the acid may be reacted with an activating agent such as a carbodiimide e.g. 1-(3-dimethylaminopropyl)-3-ethylcarbodiimide or N,N'-dicyclohexylcarbodiimide and the amine $HNR^{15}R^{15}$ optionally in the presence of a base such as an amine e.g. triethylamine or N-methylmorpholine in a solvent such as dimethylforma- Amides of formula (1a) can also be prepared directly from esters of formula (1) described in Scheme 1 by heating with an amine of formula $HNR^{15}R^{15}$ up to the reflux temperature of that amine either at atmospheric pressure or under pressure in a sealed tube. Carboxamides of formula (1b) in which X is a —O— or —S— atom and Y is a $C(CONH_2)=$ group, and where A, Ar, $Alk^1$, L, n and $Cy^1$ are as previously defined may also be prepared by reaction of an ester of formula (1) with liquid ammonia in a solvent such as 2-ethoxyethanol at elevated pressure (200-400 psi) in a Parr pressure vessel and temperature between 60-120° C. In another process carboxamides of formula (1b) as described above could also be prepared by hydrolysis of a nitrile of formula (1c) with a base such as an alkali metal hydroxide e.g. sodium hydroxide or potassium hydroxide in water with a solvent such as an alcohol e.g. ethanol at a temperature from around ambient up to the reflux temperature.

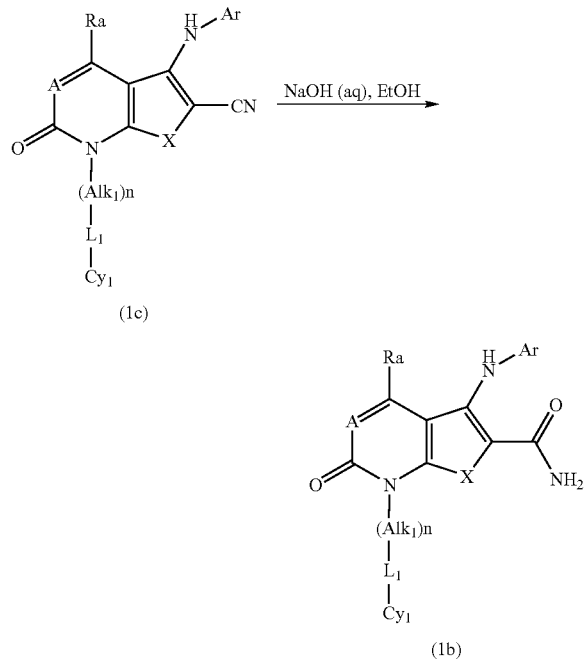

In another process compounds of formula (1) in which A is a —C(H)= group, $R^a$ is H, X is a —S— atom, Y is a —C($CR^{10a}$)= group where $R^{10a}$ is a —CN, —$NO_2$, —$CONH_2$, —$CONHR^{11}$, —CON($R^{11}$)$_2$, —$COR^{11}$ or —$CO_2Alk^6$ group, L is a covalent bond, n=0 and $Cy^1$, $R^{11}$, $Alk^6$ and Ar are as previously defined may be prepared by the reactions set out in Scheme 5.

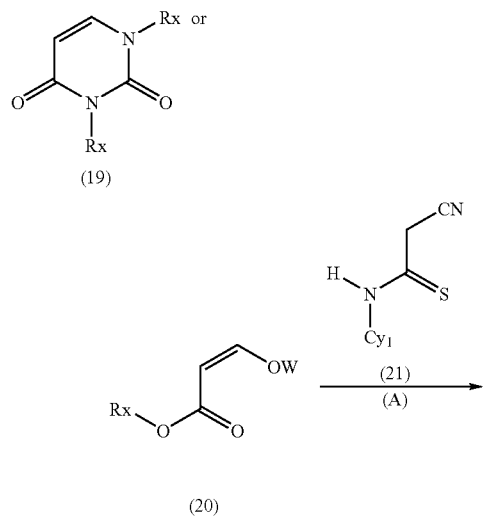

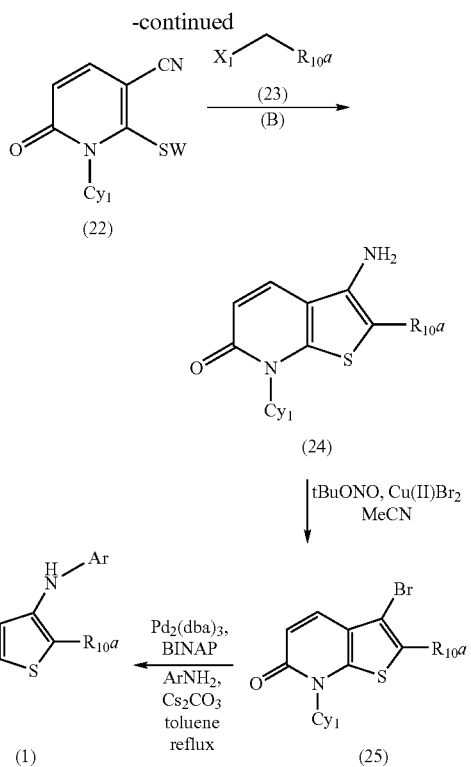

Thus in step (A) of the reaction scheme a compound of formulae (19) or (20), where Rx is an optionally substituted alkyl group e.g. methyl and W is a hydrogen atom metal ion or amine salt, may be reacted with a thioamide of formula (21). The reaction may be performed in the presence of a base. Appropriate bases may include, but are not limited to, lithium bases such as n-butyl or t-butyl lithium or lithium diisopropylamide (LDA), or silazanes e.g. lithium hexamethyldisilazane (LiHMDS) or sodium hexamethyldisilazane (NaHMDS), or a carbonate, e.g. potassium carbonate, an alkoxide, e.g. sodium ethoxide, sodium methoxide, potassium t-butoxide, a hydroxide e.g. NaOH or a hydride, e.g. sodium hydride, or an organic amine e.g. triethylamine or N,N-diisopropylethylamine or a cyclic amine, such as N-methylmorpholine or pyridine. The reaction may be performed in an organic solvent such as an amide e.g. a substituted amide such as dimethylformamide, an ether e.g. a cyclic ether such as tetrahydrofuran or dioxane or an alcohol e.g. methanol, ethanol or propanol or acetonitrile, at a temperature from ambient to the reflux temperature. In one particular aspect of the process the reaction is achieved using an alkoxide base, especially sodium ethoxide or sodium methoxide in an alcoholic solvent, especially ethanol at reflux temperature.

Intermediates of formula (19), where not commercially available, may be prepared using standard methodology. (See, for example, Mir Hedayatullah, J. Heterocyclic Chem., 18, 339, (1981)). Similarly, intermediates of formula (20) where not commercially available, may be prepared using standard methodology. For example they may be prepared in-situ by reaction of an acetate e.g. ethyl acetate with a base such as sodium methoxide followed by addition of a formate e.g. methyl formate.

In a similar manner, Intermediates of formula (21), if not commercially available, may be prepared using methods known to those skilled in the art (see, for example Adhikari et al, Aust. J. Chem., 52, 63-67, (1999)). For example, an isothiocyanante of formula $Cy^1NCS$ may be reacted with acetonitrile in the presence of a base e.g. NaHMDS in a suitable solvent e.g. tetrahydrofuran, optionally at a low temperature, e.g. around −78° C. According to the nature of the group $Cy^1$, the Intermediate of formula (21) may be prepared in situ, for example, using the methods as described herein, followed by subsequent addition of a compound of formulae (19) or (20).

During the course of this process an intermediate of formula (22) may be formed. If desired the intermediate may be isolated at the end of step (A) and subsequently reacted with intermediate (23) to form the desired amine (24). In some instances however it may advantageous not to isolate the intermediate of formula (22) and reaction (B) may be carried out directly with the reaction mixture of step (A).

If a different solvent is used during the second stage of the process, it may be necessary to evaporate the solvent, in vacuo, from the first stage of the process before proceeding with the second stage. Once evaporated, the crude solids from step (A) may be used in the next stage or they may be purified, for example, by crystallisation, to yield an isolated intermediate, such as a compound of formula (22).

During step (B) of the process an intermediate of formula (23) may then be added to the reaction mixture or to the crude solids or purified product from step (A) in a suitable solvent. Suitable solvents include, but are not limited to, amides e.g. a substituted amide such as dimethylformamide, alcohols e.g. ethanol, methanol or isopropyl alcohol, ethers e.g. a cyclic ether such as tetrahydrofuran or dioxane or acetonitrile. The reaction may be performed at a temperature from ambient up to the reflux temperature.

During the course of step (B) an intermediate of formula (26):

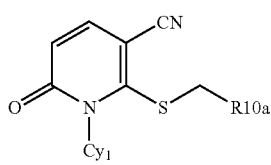

(26)

may be observed or even isolated, depending upon the nature of the group R. The intermediate of formula (26) may be converted to a compound of formula (24) using the methods described above. In this situation it may be necessary to add a base, in order for the reaction to proceed to completion. Appropriate bases include carbonates e.g. caesium or potassium carbonate, or alkoxides e.g. potassium t-butoxide, or hydrides e.g. sodium hydride or organic amines e.g. triethylamine or N,N-diisopropylethylamine or cyclic amines, such as N-methylmorpholine or pyridine.

Amines of formula (24) can be converted to bromides of formula (25) by standard methods such as for example by the Sandmeyer reaction as previously described for compounds of formula (7). Compounds of formula (1) can then be prepared from these bromides by the palladium catalysed amination reactions already described.

It will be appreciated that Intermediates of formula (23) where not commercially available may be prepared using standard methods known to those skilled in the art. For example, alcohol groups may be converted into leaving groups, such as halogen atoms or sulfonyloxy groups using conditions known to the skilled artisan. For example, an alcohol may be reacted with thionyl chloride in a halogenated hydrocarbon e.g., dichloromethane to yield the corresponding chloride. A base e.g., triethylamine may also be used in the reaction.

It will be appreciated that intermediates, such as intermediates (19), (20), (21) or (23), if not available commercially, may also be prepared by methods known to those skilled in the art following procedures set forth in references such as Rodd's Chemistry of Carbon Compounds, Volumes 1-15 and Supplementals (Elsevier Science Publishers, 1989), Fieser and Fieser's Reagents for Organic Synthesis, Volumes 1-19 (John Wiley and Sons, 1999), Comprehensive Heterocyclic Chemistry, Ed. Katritzky et al, Volumes 1-8, 1984 and Volumes 1-11, 1994 (Pergamon), Comprehensive Organic Functional Group Transformations, Ed. Katritzky et al, Volumes 1-7, 1995 Pergamon), Comprehensive Organic Synthesis, Ed. Trost and Flemming, Volumes 1-9, (Pergamon, 1991), Encyclopedia of Reagents for Organic Synthesis Ed. Paquette, Volumes 1-8 (John Wiley and Sons, 1995), Larock's Comprehensive Organic Transformations (VCH Publishers Inc., 1989) and March's Advanced Organic Chemistry (John Wiley and Sons, 1992).

According to a further aspect of the invention a compound of formula (1) in which X is an —S— atom and Y is a —C(S(O)$_2$NR$^{16}$R$^{16}$)= group (where each R$^{16}$ substituent is independently H or R$^{11}$ as previously defined) may be prepared by the route set out in Scheme 6.

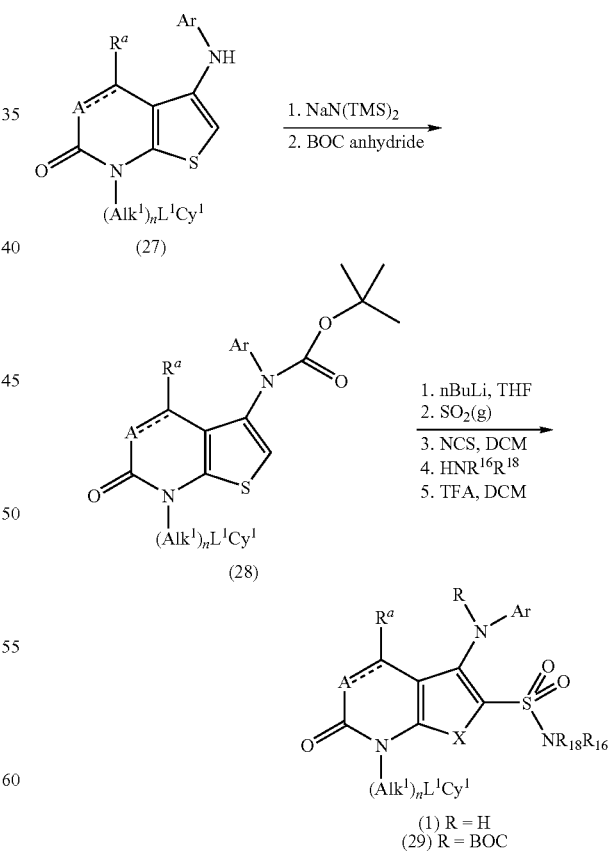

Thus a compound of formula (28) can be obtained by reaction of a compound of formula (27) with a metal amide base such as sodium bis(trimethylsilyl)amide in a solvent such as an ether, e.g. a cyclic ether such as tetrahydrofuran at a temperature of around 0° C. and then adding di-tert-butyl dicarbonate in a solvent such as tetrahydrofuran and stirring at ambient temperature. A compound of formula (1) can then be prepared by the following reaction sequence. A compound of formula (28) is treated with a base such as an alkyl lithium, e.g. n-butyl lithium in a solvent such as an ether e.g. a cyclic ether such as tetrahydrofuran at a temperature of around −78° C. Sulfur dioxide gas is bubbled through the reaction mixture before allowing the reaction to warm to room temperature. Solvents are removed in vacuo and the crude material dissolved in a solvent such as a halogenated hydrocarbon, e.g. dichloromethane and the mixture treated with a chlorinating reagent such as N-chlorosuccinimide at around ambient temperature. An amine of formula $HNR^{16}R^{16}$ or ammonia can then be added to the reaction mixture to produce a compound of formula (29), where R=t-butoxycarbonyl. A sulphonamide of formula (1) can then be prepared by treating a compound of formula (29) with an acid e.g. a mineral acid such as HCl or an organic acid such as trifluoroacetic acid in a solvent such as a halogenated hydrocarbon e.g. dichloromethane. Intermediates of formula (27) may be obtained by decarboxylation of compounds of formula (17) with an acid such as a mineral acid e.g. HCl in a solvent such as an ether e.g. a cyclic ether e.g. tetrahydrofuran or 1,4-dioxane at a temperature from 50° C. up to the reflux temperature.

Compounds of formula (1) in which A is a —N═ atom may be obtained using the synthetic routes in Schemes (1) and (2) with a pyrimidine starting material of formula (12):

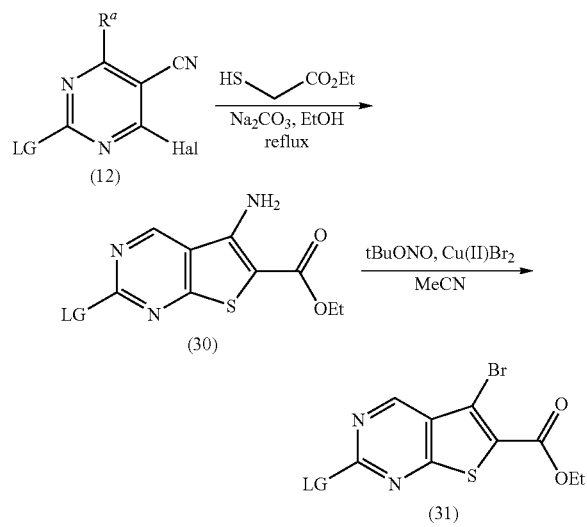

wherein Hal is a halogen atom such as a chlorine atom and LG is a halogen such as chlorine or group such as a methylsulfanyl or methylsulfonyl. Compound (30) and analogues, where LG is a methylsulfanyl group, are known [Santilli et al, J. Heterocycl. Chem. 8, 445-453 (1971)]. A compound of formula (30) can undergo a reaction such as the Sandmeyer reaction as described for compounds of formula (7) to afford a bromide of formula (31). In subsequent steps the methylsulfanyl group or other leaving group LG present in compounds such as (31) may be hydrolysed using a base such as sodium or potassium hydroxide in a solvent such as an alcohol e.g. methanol or ethanol at an elevated temperature, e.g. the reflux temperature. Alternatively, the LG group may first be converted to an ether by reaction with an alkoxide such as sodium methoxide or sodium phenyl methanolate in a solvent, e.g. an alcohol such as methanol or ethanol at a temperature between 0° C. and the reflux, and the ether then cleaved using standard procedures such as by reduction with hydrogen gas in the presence of a catalyst such as a palladium catalyst, e.g. palladium on charcoal, or where the ether is an alkyl ether, by reaction with a trialkylsilyl halide such as trimethylsilyl chloride, in the presence of an inorganic halide such as sodium iodide in a solvent such as a halogenated hydrocarbon, e.g. dichloromethane or in a nitrile e.g. acetonitrile. This will reveal the pyrimidinone functionality which can be either alkylated or arylated as described for compounds of formula (4) and can be converted to compounds of formula (1) as previously described.

Compounds of the invention and intermediates thereto where A represents a —N($R^b$)— or —C($R^b$)($R^c$)— group may be generated from corresponding compounds of the invention or intermediates thereto where A represents a —N═ or —C($R^b$)═ group by reduction, for instance by catalytic hydrogenation using a metal catalyst such as palladium on charcoal in the presence of hydrogen gas at an elevated pressure in a solvent such as an alcohol, e.g. ethanol optionally at an elevated temperature e.g. between 40° C. and 60° C.

Where in the general processes described above intermediates such as alkylating agents of formula $Cy^1L^1(Alk^1)_nZ$, reagents of formula $HXCH_2CO2Et$ and any other intermediates required in the synthesis of compounds of the invention are not available commercially or known in the literature, they may be readily obtained from simpler known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other intermediates and in particular compounds of formula (1) where appropriate functional groups exist in these compounds. Particular examples of such methods are given in the Examples hereinafter.

Thus for example aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile, a thiomethyl group may be introduced by using dimethyldisulphide as the electrophile, an alcohol group may be introduced by using an aldehyde as electrophile and an acid may be introduced by using carbon dioxide as electrophile. Aromatic acids of formula $ArCO_2H$ may also be generated by quenching Grignard reagents of formula ArMgHal with carbon dioxide.

Aromatic acids of formula $ArCO_2H$ generated by this method and acid containing compounds in general may be converted to activated derivatives, e.g. acid halides by reaction with a halogenating agent such as a thionyl halide e.g. thionyl chloride, a phosphorous trihalide such as phosphorous trichloride or a phosphorous pentahalide such as phosphorous pentachloride optionally in an inert solvent such as an aromatic hydrocarbon e.g. toluene or a chlorinated hydrocarbon e.g. dichloromethane at a temperature from about 0° C. to the reflux temperature, or may be converted into Weinreb amides of formula ArC(O)N(OMe)Me by conversion to the acid halide as just described and subsequent reaction with an amine of formula HN(OMe)Me or a salt thereof, optionally in the presence of a base such as an organic amine, e.g. triethylamine in an inert solvent such as an aromatic hydrocarbon e.g. toluene or a chlorinated hydrocarbon e.g. dichloromethane at a temperature from about 0° C. to ambient temperature.

Compounds of the invention and intermediates thereto may be prepared by alkylation, arylation or heteroarylation. For example, compounds containing a -$L^1$H group (where $L^1$ is a linker atom or group) may be treated with an alkylating agent $Cy^1Z^2$ in which $Z^2$ is a leaving atom or group such as a halogen atom, e.g. a fluorine, chlorine, bromine or iodine atom or a sulphonyloxy group such as an alkylsulphonyloxy, e.g. trifluoromethylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, compounds containing a -$L^2$H group as defined above may be functionalised by acylation or thioacylation, for example by reaction with the alkylating agents just described but in which $Z^2$ is replaced by a —C(O)$Z^3$, C(S)$Z^3$, —N($R^2$)CO$Z^3$ or —N($R^2$)C(S)$Z^3$ group in which $Z^3$ is a leaving atom or group as described for $Z^2$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which $Z^2$ is replaced by a —$CO_2$H group) in the presence of a condensing agent, for example a diimide such as 1-(3-dimethylaminopropyl)-3-ethylcarbodiimide or N,N'-dicyclohexylcarbodiimide, or a benzotriazole such as [O-(7-azabenzo-triazol-1-yl)-1,1,3,3-tetramethyluronium]hexafluorophosphate advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $Z^2$ is replaced by a —S(O)Hal or —$SO_2$Hal group [in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a -$L^2$H group as defined above may be coupled with one of the alkylation agents just described but in which $Z^2$ is replaced by an —OH group in a solvent such as tetrahydrofuran in the presence of a phosphine, e.g. triphenylphosphine and an activator such as diethyl, diisopropyl- or dimethylazodicarboxylate.

Ester groups such as —$CO_2$Alk$^6$ and —$CO_2R^4$ in the compound of formula (1) and intermediates thereto may be converted to the corresponding acid [—$CO_2$H] by acid- or base-catalysed hydrolysis depending on the nature of the group Alk$^6$ or $R^4$. Acid- or base-catalysed hydrolysis may be achieved for example by treatment with an organic or inorganic acid, e.g. trifluoroacetic acid in an organic solvent e.g. dichloromethane or a mineral acid such as hydrochloric acid in a solvent such as dioxan or an alkali metal hydroxide, e.g. lithium hydroxide in an aqueous alcohol, e.g. aqueous methanol.

In a further example, —O$R^6$ [where $R^6$ represents an alkyl group such as methyl group] in compounds of formula (1) and intermediates thereto may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^{31}$ group (where $R^{31}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [e.g. —$CO_2$Alk$^6$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding O$R^6$ group by coupling with a reagent $R^6$OH in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in the compounds may be obtained, in another example, by reaction of a corresponding amine [—$NH_2$] with sulphamide in the presence of an organic base such as pyridine at an elevated temperature, e.g. the reflux temperature.

In another example compounds containing a —NHCS$R^7$ or —CSNH$R^7$ group may be prepared by treating a corresponding compound containing a —NHCO$R^7$ or —CONH$R^7$ group with a thiation reagent, such as Lawesson's Reagent or $P_2S_5$, in an anhydrous solvent, for example a cyclic ether such as tetrahydrofuran, at an elevated temperature such as the reflux temperature.

In a further example amine (—$NH_2$) groups may be alkylated using a reductive alkylation process employing an aldehyde and a reducing agent. Suitable reducing agents include borohydrides for example sodium triacetoxyborohyride or sodium cyanoborohydride. The reduction may be carried out in a solvent such as a halogenated hydrocarbon, e.g. dichloromethane, a ketone such as acetone, or an alcohol, e.g. ethanol, where necessary in the presence of an acid such as acetic acid at around ambient temperature. Alternatively, the amine and aldehyde may be initially reacted in a solvent such as an aromatic hydrocarbon e.g. toluene and then subjected to hydrogenation in the presence of a metal catalyst, for example palladium on a support such as carbon, in a solvent such as an alcohol, e.g. ethanol.

In a further example, amine [—$NH_2$] groups in compounds of formula (1) and intermediates thereto may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

In a further example amine (—CH$_2$NH$_2$) groups in compounds of formula (1) and intermediates thereto may be obtained by reduction of nitrites (—CN), for example by catalytic hydrogenation using for example hydrogen in the presence of a metal catalyst, for example palladium on a support such as carbon, or Raney® nickel, in a solvent such as an ether e.g. a cyclic ether such as tetrahydrofuran or an alcohol e.g. methanol or ethanol, optionally in the presence of ammonia solution at a temperature from ambient to the reflux temperature, or by chemical reduction using for example a metal hydride e.g. lithium aluminium hydride, in a solvent such as an ether e.g. a cyclic ether such as tetrahydrofuran, at a temperature from 0° C. to the reflux temperature.

In another example, sulphur atoms in the compounds, for example when present in a group $L^1$ or $L^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In a further example N-oxides of compounds of formula (1) may in general be prepared for example by oxidation of the corresponding nitrogen base as described above in relation to the preparation of intermediates of formula (5).

Salts of compounds of formula (1) may be prepared by reaction of compounds of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above. Alternatively, a particular enantiomer may be obtained by performing an enantiomer specific enzymatic biotransformation e.g. an ester hydrolysis using an esterase and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the invention. All temperatures are in OC.

The following abbreviations are used:
NMM—N-methylmorpholine; EtOAc—ethyl acetate;
MeOH—methanol; BOC—butoxycarbonyl;
DCM—dichloromethane; AcOH—acetic acid;
DIPEA—diisopropylethylamine; EtOH—ethanol;
Pyr—pyridine; Ar—aryl;
DMSO—dimethylsulphoxide; iPr—isopropyl;
Et$_2$O—diethylether; Me—methyl;
THF—tetrahydrofuran; h—hour;
MCPBA—3-chloroperoxybenzoic acid; NBS—N-bromosuccinimide;
FMOC—9-fluorenylmethoxycarbonyl; r.t.—room temperature;
DBU—1,8-Diazabicyclo[5, 4-0]undec-7-ene;
EDC—1-[3-(dimethylamino)propyl]-3-ethylcarbodiimide hydrochloride;
HOBT—1-hydroxybenzotriazole hydrate;
BINAP—2,2'-bis(diphenylphosphino)-1-1'-binaphthyl;
DMF—N,N-dimethylformamide;
DME—Ethylene glycol dimethyl ether
p.s.i.—pounds per square inch All NMRs were obtained either at 300 MHz or 400 MHz.

Compounds were named with the aid of either Beilstein Autonom supplied by MDL Information Systems GmbH, Theodor-Heuss-Allee 108, D-60486 Frankfurt, Germany or ACD Labs Name (v.5.0 or v.6.0) supplied by Advanced Chemical Development, Toronto, Canada.

LCMS retention times (RT) quoted were generated on a Hewlett Packard 1100 LC/MS using the following method: Phenomenex Luna 3μ C$_{18}$(2) 50×4.6 mm column; mobile phase A=0.1% formic acid in water; mobile phase B=0.1% formic acid in MeCN; flow rate of 0.9 mLmin$^{-1}$, column temperature 40° C.

| Gradient:- | |
|---|---|
| Time | % B |
| Initial | 5 |
| 2.00 | 95 |
| 3.00 | 95 |
| 5 | end |

Where stated alternative LCMS conditions (Conditions B) were used:

LCMS retention times (RT) quoted were generated on a Hewlett Packard 1100/ThermoFinnigan LCQ Duo LC/MS system using Electrospray ionisation and the following LC method: Phenomenex Luna C$_{18}$(2) 5μ 100 mm×4.6 mm column; mobile phase A=0.08% formic acid in water; mobile phase B=0.08% formic acid in MeCN; flow rate of 3.0 mLmin$^{-1}$, column temperature 35° C.

| Gradient:- | | |
|---|---|---|
| Time (min) | % A | % B |
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Intermediate 1

Ethyl 3-aminothieno[2,3-b]pyridine-2-carboxylate

A mixture of 2-chloro-3-cyanopyridine (330 g), ethyl 2-mercaptoacetate (361.2 g), sodium carbonate (265 g) and EtOH (1.2 L) was heated to reflux for 4.5 hours. It was then cooled to ambient temperature, added to water (10 L) and the addition was washed in with water (5 L). The resulting slurry was stirred for 30 minutes and then it was filtered. The filter cake was washed with two portions of water (2×2.5 L) and dried at the pump. The solids were then dried to constant weight under vacuum at 45° C. to yield the title compound as a brown solid (493.1 g, 93.2%). δH (CDCl$_3$) 8.68 (1H, dd, J 4.7, 1.2 Hz), 7.93 (1H, dd, J 8.5, 1.2 Hz), 7.29 (1H, dd, J 8.5, 4.7 Hz), 5.90 (2H, b), 4.38 (2H, q, J 7.0 Hz), 1.40 (3H, t, J 7.0 Hz). LCMS RT 2.9 minutes, 223 (M+H)$^+$ Intermediate 2

Ethyl 3-bromothieno[2,3-b]pyridine-2-carboxylate

Intermediate 1 (363.6 g) was added in portions over two hours to a mixture of copper(II) bromide (403.3 g), t-butyl nitrite (220.6 g) and acetonitrile (3.6 L) stirred at a temperature of 20 to 25° C. The mixture was stirred at 20° C. for 2 hours before it was slowly added to 2M HCl(aq) (4.2 L). The reaction mixture slurry was filtered and the solids were washed with water (500 mL). The combined filtrate was extracted with ethyl acetate (8 L), this ethyl acetate solution was washed with 2M HCl(aq) (2.2 L). The solids were dissolved in ethyl acetate (6 L), this solution was washed twice with 2M HCl(aq) (4.4 L and 2.2 L). The two ethyl acetate solutions were then combined and washed with 2M HCl(aq) (2.2 L) and twice with water (2×2 L). The ethyl acetate solution was then dried (MgSO$_4$), filtered and concentrated in vacuo at 40 mbar and 60° C. to give a solid residue. This was broken up and dried to constant weight under vacuum at 45° C. to yield the title compound as a brown solid (458.5 g, 97.9%). δH (DMSO-d6) 8.89 (1H, d, J 4.7 Hz), 8.47 (1H, d, J 8.6 Hz), 7.71 (1H, dd, J 8.6, 4.7 Hz), 4.46 (2H, q, J 7.2 Hz), 1.40 (3H, t, J 7.2 Hz). LCMS RT 3.8 minutes, 288 (M+H)$^+$ Intermediate 3

Ethyl 3-Bromothieno[2,3-b]pyridine-2-carboxylate N-oxide

To a slurry of Intermediate 2 (214 g, 0.747 Mol) in DCM (2140 mL) under nitrogen was added MCPBA (240 g@70%=168 g, 0.97 Mol) portion wise over 0.5 h. The reaction was then stirred at room temperature for 18 h. The reaction mixture was quenched with water (800 mL) and pH adjusted to 8.5 with 10% w/v sodium carbonate solution (1250 mL). The basic aqueous layer was removed and the organic layer washed with water until pH 7. The organic layer was concentrated in vacuo and the crude title product was recovered as a tan solid. The crude product was purified by slurrying in tert-butylmethylether (600 mL) for 1 h at 0-5° C. to give the title compound (174 g, 77%). δH (CDCl$_3$) 8.44 (1H, dd, J 6.2, 0.8 Hz), 7.87 (1H, dd, J 8.3, 0.8 Hz), 7.48 (1H, dd, J 8.3, 6.2 Hz), 4.49 (2H, q, J 7.1 Hz), 1.48 (3H, t, J 7.1 Hz). LCMS (ES$^+$) RT 2.61 minutes, 302 (M+H)$^+$ Intermediate 4

Ethyl 3-bromo-6-oxo-6,7-dihydrothieno[2,3-b]pyridine-2-carboxylate

A mixture of Intermediate 3 (500 mg, 1.66 mmol) and DMF (10 mL) was set to stir at 0° C. under nitrogen. To this reaction mixture was added trifluoroacetic anhydride (3.49 g, 2.36 mL, 16.6 mmol) in one portion via syringe. After stirring for 16 hours the volatiles were removed in vacuo and the residue co-evaporated with toluene (2×20 mL). The crude material was then extracted with EtOAc (2×100 mL). The EtOAc extracts were dried (MgSO$_4$) and concentrated in vacuo. The crude product was purified by a re-slurry in toluene (10 mL) to give the title compound as a beige solid (260 mg, 52%). δH (DMSO-d6) 12.20 (1H, brs), 7.75 (1H, d, J 9.0 Hz), 6.50 (1H, d, J 9.0 Hz), 4.15 (2H, q, J 7.1 Hz), 1.12 (3H, t, J 7.1 Hz). LCMS (ES$^+$) RT 2.86 minutes, 302 ((M+H)$^+$, 100%). MP=261.7-268.1° C.

Intermediate 5

Ethyl 3-bromo-6-oxo-7-phenyl-6,7-dihydrothieno[2,3-b]pyridine-2-carboxylate

To a 2 necked round bottomed flask was added in sequence Intermediate 4 (302 mg, 1.00 mmol), copper(II) acetate (278 mg, 1.50 mmol), phenylboronic acid (488 mg, 4.00 mmol), DCM (5 mL) and pyridine (158 mg, 2.00 mmol). The reaction was stirred at room temperature for 18 h with the exclusion of moisture. The reaction was then diluted with DCM (50 mL), washed with 2M HCl(aq) (50 mL), the aqueous was re-extracted with DCM (50 mL). The combined organics were then washed with water (50 mL), dried (MgSO$_4$) and concentrated in vacuo. The crude product was purified by a slurry in methanol (12 mL), to give the title compound as a beige solid (270 mg, 72%). δH (CDCl$_3$) 7.82 (1H, d, J 8.5 Hz), 7.70-7.62 (3H, m), 7.54-7.42 (2H, m), 6.70 (1H, d, J 8.5 Hz), 4.15 (2H, q, J 7.1 Hz), 1.14 (3H, t, J 7.1 Hz). LCMS (ES$^+$) RT 3.75 minutes, 378 (M+H)$^+$. MP=201.6-206.0° C.

Intermediate 6

3-Bromo-6-oxo-6,7-dihydrothieno[2,3-b]pyridine-2-carboxylic acid

Lithium hydroxide monohydrate (1.39 g, 33.1 mmol) was added to a suspension of Intermediate 4 (5.0 g, 16.55 mmol) in water (100 mL) and the reaction stirred for 5 minutes. THF (10 mL) was added and the reaction was stirred at r.t. for 18 h. 2M HCl(aq) (40 mL) was added to pH 1-2 and the resultant precipitate was collected by filtration, washed sparingly with EtOH and dried in vacuo to give the title compound as an off-white solid (4.5 g). δH (DMSO-d6) 7.90 (1H, d, J 9.2 Hz), 6.67 (1H, d, J 9.2 Hz), pyridone and carboxylic acid protons not observed.

Intermediate 7

3-Bromo-6-oxo-6,7-dihydrothieno[2,3-b]pyridine-2-carboxamide 1,1'Carbonyldiimidazole (3.18 g, 19.6 mmol) was added to a suspension of Intermediate 6 (4.30 g, 15.7 mmol) in anhydrous DMF (50 mL) and the reaction stirred at r.t. under nitrogen until solution was achieved (30 minutes). Ammonium hydroxide (50 mL of 28% NH$_3$ in water) was added and the reaction stirred for 15 minutes before removing solvents in vacuo. The residue was suspended in water (75 mL) and treated with 2M HCl(aq) (20 mL). The resultant solid was collected by filtration, washed with water and dried in a vacuum oven to give the title compound as a pale brown solid (3.70 g). δH (DMSO-d6) 7.69 (1H, d, J 9.1 Hz), 6.49 (1H, d, J 9.1 Hz), 7.30 (1H, bs). LCMS (ES$^+$) 273 (M+H)$^+$.

Intermediate 8

3-Bromo-6-oxo-6,7-dihydrothieno[2,3-b]pyridine-2-carbonitrile

To a suspension of Intermediate 7 (3.70 g, 13.55 mmol) in DCM (200 mL) was added pyridine (2.70 mL, 34 mmol) followed by trifluoroacetic anhydride (2.40 mL, 17 mmol). The reaction was stirred at r.t. for 8 h before adding more trifluoroacetic anhydride (1.20 mL, 8.5 mmol). The reaction was stirred for a further 8 h and was then concentrated in vacuo. The residue was suspended in water, acidified to pH 2 with 2M HCl(aq) and the resultant solid collected by filtration, washed with water and dried in vacuo to give the title compound as a pale yellow solid (3.20 g). δH (DMSO-d6) 7.92 (1H, d, J 8.8 Hz), 6.73 (1H, d, J 8.8 Hz). LCMS (ES+) 255 (M+H)+.

Intermediate 9

3-bromo-6-oxo-7-phenyl-6,7-dihydrothieno[2,3-b]pyridine-2-carbonitrile

To an oven dried flask was added Intermediate 8 (2.0 g, 7.84 mmol), phenylboronic acid (1.19 g, 15.7 mmol), copper (II) acetate (1.42 g, 7.84 mmol), anhydrous pyridine (1.3 mL, 16 mmol) and anhydrous DCM (50 mL). The reaction mixture was stirred at r.t. with the exclusion of moisture for 48 h. The reaction was diluted with DCM (50 mL), washed with 2M HCl(aq) (100 mL), saturated NaHCO$_3$(aq) (50 mL), dried (Na$_2$SO$_4$) and concentrated in vacuo. The residue was purified by chromatography on silica (5-10% EtOAc in DCM) to give the title compound as a white solid (1.24 g). δH (DMSO-d6) 7.67 (1H, d, J 9.6 Hz), 7.58-7.50 (3H, m), 7.32-7.29 (2H, m), 6.70 (1H, d, J 9.6 Hz).

Intermediate 10

Sodium 3-cyano-6-oxo-1-phenyl-1,6-dihydro-pyridine-2-thiolate

A solution of sodium methoxide in MeOH (30 wt %, 202.2 g) was added to absolute EtOH (360 mL) followed by 1,3-dimethyluracil (75 g) and 2-cyano-N-phenyl-thioacetamide (Adhikari et al, Australian J. Chem., 1999, 52, 63-67) (90 g). The resulting mixture was heated at reflux for 8 h and then allowed to cool to ambient temperature overnight. The reaction mixture was then cooled to +5° and maintained at this temperature for at least an hour when the product was recovered by filtration. The filter cake was washed with cold (+5°) absolute ethanol (450 mL) and then dried to constant weight under vacuum at 45° to give the title compound as a pale pink solid (130.0 g). The product thus obtained contains residual EtOH and MeOH, estimated at 12.2 wt % by 1H nmr, corresponding to a corrected yield of 114.1 g. δH (DMSO-d6) 7.32 (2H, m), 7.27-7.18 (1H, m), 7.16 (1H, d, J 9.1 Hz), 6.92 (2H, m), 5.63 (1H, d, J 9.1 Hz). LCMS (Conditions B) (ES+) RT 2.43 minutes, 229 (M+H)+.

Intermediate 11

3-Amino-6-oxo-7-phenyl-6,7-dihydro-thieno[2,3-b]pyridine-2-carbonitrile

A mixture of Intermediate 10 (100 g at 100%) and chloracetonitrile (30.4 mL) in acetonitrile (500 mL) was heated at reflux for 2 h. The mixture was cooled, Initially to 40° when water (300 mL) was added, and then to +10°. The reaction was maintained at +10° for at least 1 h when the product was recovered by filtration. The filter cake was washed with cold (+10°) water (500 mL) followed by a cold (+10°) mixture of acetonitrile and water (1:1, 300 mL). The product was dried under vacuum at 50° to constant weight to give the title compound as an off-white solid (100.9 g). δH (DMSO-d6) 7.90 (1H, d, J 9.6 Hz), 7.46-7.33 (3H, m), 7.25 (2H, m), 6.95 (2H, br s), 6.35 (1H, d, J 9.6 Hz). LCMS (Conditions B) (ES+) RT 2.69 minutes, 268 (M+H)+.

Intermediate 12

3-Amino-6-oxo-7-phenyl-6,7-dihydro-thieno[2,3-b]pyridine-2-carboxylic acid ethyl ester A mixture of Intermediate 10 (0.34 g at 100%) and ethyl bromoacetate (0.197 mL) in ethanol (6 mL) were stirred at room temperature for 1 h. Water (10 mL) was then added. The solid was filtered and washed with more water (2 mL). The product was dried under vacuum at 40° to constant weight to give the title compound as a pale pink solid (0.35 g). δH (DMSO-d6) 8.2 (1H, d, J 9.6 Hz), 7.6 (3H, m), 7.45 (2H, m), 7.15 (2H, br s), 6.55 (1H, d, J 9.6 Hz), 4.15 (2H, q, J 7.1 Hz), 1.2 (3H, t, J 7.1 Hz). LCMS (Conditions B) (ES+) RT 3.29 minutes, 315 (M+H)+.

Intermediate 9 (Alternative Route)

3-Bromo-6-oxo-7-phenyl-6,7-dihydro-thieno[2,3-b]pyridine-2-carbonitrile

To a mixture of anhydrous copper (II) bromide (23.4 g) and t-butylnitrite (14.8 mL) in acetonitrile (600 mL) at room temperature, was added Intermediate 12 (20 g) portion wise, at such a rate to keep the internal temperature below 25° C. The addition took approximately 1 hour. Analysis by HPLC indicated almost complete conversion of starting material after a further 30 minutes of stirring. The reaction mixture was then poured onto 500 mL of 1M HCl (nb caution, brown fumes given off). This was then extracted with dichloromethane (2×400 mL). The combined organic extracts were then washed with 1M HCl (3×300 mL), dried over MgSO$_4$ and evaporated to dryness. The resulting crude product was then recrystallised from methyl isobutyl ketone (700 mL). The product was dried under vacuum at 500 to constant weight to give the title compound as a light brown solid (15.14 g). δH (CDCl$_3$) 7.75 (1H, d, J 8.5 Hz), 7.55-7.70 (3H, m), 7.35 (2H, m), 6.80 (1H, d, J 8.5 Hz). LCMS (Conditions B) (ES+) RT 3.54 minutes, no parent ion observed.

Intermediate 13

3-Amino-7-(2-chlorophenyl)-6-oxo-6,7-dihydrothieno[2,3-b]pyridine-2-carbonitrile Acetonitrile (10 mL) was added to a solution of sodium bis(trimethylsilyl)amide (100 mL, 1.0M in THF, 100 mmol) in THF (50 mL) at −78° C. to give a thick white precipitate. 2-Chlorophenyl isothiocyanate (7.72 g, 45.45 mmol) was added to give a brown solution. The mixture was allowed to warm to r.t. over 1 h then diluted with EtOH (50 mL). N,N-Dimethyluracil (6.4 g, 45 mmol) was added and the mixture heated at reflux for 24 h. Volatiles were removed in vacuo and the residue dissolved in acetonitrile (100 mL). Chloroacetonitrile (2.85 mL, 45 mmol) was added and the mixture heated at 50° C. for 1 h, a second charge of chloroacetonitrile (2.85 mL, 45 mmol) was added and heating continued for 1.5 h. Some of the acetonitrile (~50 mL) was removed in vacuo and water was added to precipitate the product. The brown solid was filtered off, washed with water (50 mL) and Et$_2$O (50 mL) and dried to give the title compound as a brown solid (14.3 g, quant.). δH (DMSO-d6) 8.10 (1H, d, J 9.7 Hz), 7.75-7.73 (1H, m), 7.65-7.54 (3H, m), 7.14 (2H, brs, NH$_2$), 6.54 (1H, d, J 9.7 Hz). LCMS (ES+) RT 2.97 minutes, 302 (M+H)+.

Intermediate 14

3-Bromo-7-(2-chlorophenyl)-6-oxo-6,7-dihydrothieno[2,3-b]pyridine-2-carbonitrile Intermediate 13 (1.17 g, 3.88 mmol) was suspended in acetonitrile (20 mL). Copper (II) bromide (953 mg, 4.27 mmol) was added followed by t-butyl nitrite (0.64 mL, 5.43 mmol). The mixture was stirred at r.t. for 3 h then partitioned between 2M HCl aq (100 mL) and EtOAc (100 mL). The organic layer was washed with 2M HCl aq (50 mL), 2M NaOH aq (50 mL) and water (25 mL), dried ($Na_2SO_4$) and concentrated in vacuo. Purification by column chromatography (silica, 0 to 5% EtOAc in DCM) gave the title compound as a pale brown solid (980 mg, 67%). $\delta$H (CDCl$_3$) 7.70 (1H, d, J 9.7 Hz), 7.61 (1H, dd, J 1.7, 7.7 Hz), 7.52-7.44 (2H, m), 7.34 (1H, dd, J 1.7, 7.7 Hz), 6.70 (1H, d, J 9.7 Hz). LCMS (ES$^+$) RT 3.56 minutes, 365 (M+H)$^+$.

Intermediate 15

Sodium 3-cyano-1-(4-methylphenyl)-6-oxo-1,6-dihydropyridine-2-thiolate

Sodium bis(trimethylsilyl)amide (36.8 mL, 1.0M in THF, 36.8 mmol) was added slowly to a solution of 4-tolyl isothiocyanate (2.5 g, 16.75 mmol) in THF (30 mL) and acetonitrile (5 mL) at −78° C. The mixture was warmed to r.t. over 1 h. N,N-Dimethyluracil (2.35 g, 16.75 mmol) and EtOH (20 mL) were added and the mixture heated at reflux for 4 h. Volatiles were removed in vacuo and the residue was dissolved in EtOH (6 mL). Et$_2$O (~60 mL) was added slowly to produce a fine, off-white solid. The suspension was cooled to 0° C. and the solid filtered off, washed with Et$_2$O and dried to give the title compound as an off-white solid (1.7 g, 39%). $\delta$H (DMSO-d6) 7.15-7.12 (3H, m), 6.80-6.77 (2H, m), 5.60 (1H, d, J 9.1 Hz), 2.30 (3H, s).

Intermediate 16

3-Amino-7-(4-methylphenyl)-6-oxo-6,7-dihydrothieno[2,3-b]pyridine-2-carbonitrile Chloroacetonitrile (0.41 mL, 6.4 mmol) was added to a suspension of Intermediate 15 (1.7 g, 6.44 mmol) in acetonitrile (40 mL). The mixture was heated at 45° C. for 2 h. Solvent was removed in vacuo and the residual solid was suspended in water (30 mL). The solid was filtered off, washed with water (3×10 mL) and ether (5 mL) and dried to give the title compound as an off-white solid (1.22 g, 67%). $\delta$H (DMSO-d6) 8.01 (1H, d, J 9.7 Hz), 7.34-7.32 (2H, m), 7.27-7.25 (2H, m), 7.00 (2H, br s), 6.45 (1H, d, J 9.7 Hz), 2.34 (3H, s). LCMS (ES$^+$) RT 3.03 minutes, 282.0 (M+H)$^+$ Intermediate 17

3-Bromo-7-(4-methylphenyl)-6-oxo-6,7-dihydrothieno[2,3-b]pyridine-2-carbonitrile Intermediate 16 (562 mg, 2.0 mmol) was suspended in acetonitrile (15 mL). Copper (II) bromide (419 mg, 2.2 mmol) was added followed by t-butyl nitrite (0.33 mL, 2.8 mmol). The mixture was stirred at r.t. for 3 h, then diluted with DCM (100 mL), washed with 2M HCl aq (50 mL) and 1M NaOH aq (50 mL), dried ($Na_2SO_4$) and concentrated in vacuo. Purification by column chromatography (silica, 0% to 20% EtOAc in DCM) gave the title compound as a yellow solid (450 mg, 65%). $\delta$H (CDCl$_3$) 7.59 (1H, d, J 9.7 Hz), 7.29-7.27 (2H, m), 7.13-7.10 (2H, m), 6.62 (1H, d, J 8.7 Hz), 2.33 (3H, s). LCMS (ES$^+$) RT 3.64 minutes, 345.0/347.0 ($^{79}$Br/$^{81}$Br)(M+H)$^+$ Intermediate 18

3-[(4-Fluoro-3-methylphenyl)amino]-7-(4-methylphenyl)-6-oxo-6,7-dihydrothieno[2,3-b]pyridine-2-carbonitrile A mixture of Intermediate 17 (225 mg, 0.65 mmol), 4-fluoro-3-methyl aniline (98 mg, 0.78 mmol), caesium carbonate (297 mg, 0.91 mmol), BINAP (41 mg, 0.065 mmol, 10 mol %) and tris(dibenzylideneacetone)dipalladium(0) (30 mg, 0.0325 mmol, 5 mol %) in toluene (5 mL) was heated at 100° C. under N$_2$ for 18 h. The volatiles were removed in vacuo and the resulting solids suspended in water. The solid was filtered off, washed with water (2×15 mL) and ether (3×10 mL) to give the title compound as a brown solid. This was used in the next step without further purification. LCMS (ES$^+$) RT 3.66 minutes, 390.0 (M+H)$^+$ Intermediate 19

Sodium 3-cyano-1-cyclopropyl-6-oxo-1,6-dihydropyridine-2-thiolate

A solution of sodium bis(trimethylsilyl)amide (122 mL of a 1.0M solution in THF, 122 mmol) was added to a solution of cyclopropyl isothiocyanate (4.85 g, 48.9 mmol) and acetonitrile (25.5 mL, 10 eq) in THF (50 mL) at −78° C. The mixture was allowed to warm to r.t. over 2 h. N,N-Dimethyluracil (5.9 g, 49 mmol) and EtOH (60 mL) were added and the mixture heated at reflux for 3 h then stirred at r.t. overnight. Volatiles were removed In vacuo. The residue was taken up in a mixture of EtOH and EtOAc then Et$_2$O was added. The sticky solid was filtered off and dried to give the title compound (11 g, crude) which was used in the next step without further purification.

Intermediate 20

3-Amino-7-cyclopropyl-6-oxo-6,7-dihydrothieno[2,3-b]pyridine-2-carbonitrile

A mixture of crude Intermediate 19 (9 g, assume 42 mmol) and chloroacetonitrile (2.7 mL, 42 mmol) in acetonitrile (100 mL) was heated at reflux for 3 h. Volatiles were removed in vacuo. Water (100 mL) was added to the residue and the solid obtained filtered off and dried. The crude material was partitioned between water and EtOAc and the aqueous phase extracted with EtOAc. The combined organic phases were concentrated in vacuo. The residue was dissolved in EtOH and the solution treated with Et$_2$O to give a solid which was filtered off and dried to give the title compound as a light brown solid (2.5 g). $\delta$H (CDCl$_3$) 7.42 (1H, d, J 9.6 Hz), 6.52 (1H, d, J 9.6 Hz), 4.6 (2H, br s), 3.08-3.00 (1H, m), 1.2-1.1 (2H, m), 1.08-1.0 (2H, m). LCMS (ES$^+$) RT 2.532 minutes, 232 (M+H)$^+$ Intermediate 21

3-Bromo-7-cyclopropyl-6-oxo-6,7-dihydrothieno[2,3-b]pyridine-2-carbonitrile

Copper (II) bromide (0.53 g, 2.37 mmol) and t-butyl nitrite (0.40 mL, 3.02 mmol) were added to a solution of Intermediate 20 (0.5 g, 2.16 mmol) in acetonitrile (15 mL). The reaction mixture was stirred at r.t. for 4 h. DCM (100 mL) was added and the mixture washed with 2M HCl aq and 2M NaOH aq, dried (MgSO$_4$) and concentrated in vacuo to give the title compound (400 mg, 63%). δH (CDCl$_3$) 7.62 (1H, d, J 10.2 Hz), 6.63 (1H, d, J 10.3 Hz), 3.1-3.0 (1H, m), 1.3-1.2 (2H, m), 1.1-1.0 (2H, m). LCMS (ES$^+$) RT 3.184 minutes, 296.8 (M+H)$_4$ Intermediate 22

Sodium 3-cyano-1-(2-methylphenyl)-6-oxo-1,6-dihydropyridine-2-thiolate

A solution of sodium bis(trimethylsilyl)amide (84 mL of a 1.0M solution in THF, 84 mmol) was added to a solution of o-tolyl isothiocyanate (5.0 g, 33.5 mmol) and acetonitrile (18 mL, 0.345 mol) in THF (100 mL) at −78° C. The mixture was allowed to warm to r.t. over 3 h. N,N-Dimethyluracil (4.62 g, 33 mmol) and EtOH (75 mL) were added and the mixture heated at reflux for 3 h then stirred at r.t. overnight. Volatiles were removed in vacuo. The residue was used crude in the next step without further purification.

Intermediate 23

3-Amino-7-(2-methylphenyl)-6-oxo-6,7-dihydrothieno[2,3-b]pyridine-2-carbonitrile A mixture of crude Intermediate 22 (half of material obtained above) and chloroacetonitrile (1.94 mL) in acetonitrile (25 mL) was heated at reflux for 5 h. Volatiles were removed in vacuo. The residue was treated with water to give a solid which was filtered off and dried to give the title compound (3.0 g). δH (DMSO-d6) 8.16 (1H, d, J 9.6 Hz), 7.7-7.5 (4H, m), 7.19 (2H, s), 6.6 (1H, d, J 9.6 Hz), 2.0 (3H, s). LCMS (ES$^+$) RT 2.932 minutes, 281.9 (M+H)$^+$ Intermediate 24

3-Bromo-7-(2-methylphenyl)-6-oxo-6,7-dihydrothieno[2,3-b]pyridine-2-carbonitrile Prepared from Intermediate 23 by the method of Intermediate 14. δH (CDCl$_3$) 7.8 (1H, d, J 9.6 Hz), 7.55-7.4 (4H, m), 6.8 (1H, d, J 9.6 Hz), 2.12 (3H, s). LCMS (ES$^+$) RT 4.10 minutes, no mass ion observed.

Intermediate 25

7-(2-Methylphenyl)-3-[(3-methylphenyl)amino]-6-oxo-6,7-dihydrothieno[2,3-b]pyridine-2-carbonitrile Prepared from Intermediate 24 and m-toluidine by the method of example 1. LCMS (ES$^+$) RT 3.64 minutes, 372.0 (M+H)$^+$ Intermediate 26

Ethyl 3-bromo-7-(1H-indol-5-yl)-6-oxo-6,7-dihydrothieno[2,3-b]pyridine-2-carboxylate A mixture of 5-indolyl boronic acid (644 mg, 4 mmol), Intermediate 4 (604 mg, 2 mmol) and copper (I) acetate (363 mg, 2 mmol) in pyridine (2 mL) was stirred at r.t. overnight. The mixture was partitioned between DCM and 2M HCl aq. The organic phase was dried (Na$_2$SO$_4$) and concentrated in vacuo. Purification by column chromatography (silica, 10% EtOAc in DCM) gave the title compound as a pale tan solid (650 mg, 78%). δH (DMSO-d6) 11.61 (1H, br s), 8.01 (1H, d, J 9.3 Hz), 7.80 (1H, d, J 2.0 Hz), 7.74 (1H, d, J 8.6 Hz), 7.65 (1H, m), 7.23 (1H, dd, J 8.6, 2.0 Hz), 6.81 (1H, d, J 9.6 Hz), 6.68 (1H, m), 4.33 (2H, q, J 7.1 Hz), 1.32 (3H, t, J 7.1 Hz). LCMS (ES$^+$) RT 3.53 minutes, 419/420 ($^{79}$Br/$^{81}$Br) (M+H)$^+$.

Intermediate 27

Ethyl 3-bromo-7-[1-(methylsulfonyl)-1H-indol-5-yl]-6-oxo-6,7-dihydrothieno[2,3-b]pyridine-2-carboxylate Sodium hydride (60% in mineral oil) (58 mg, 1.44 mmol) was added to a solution of Intermediate 26 (500 mg, 1.2 mmol) in THF (30 mL) at 0° C. The mixture was stirred for 5 min at 0° C. and 15 min at r.t. then methanesulfonyl chloride (0.124 mL, 1.6 mmol) was added and stirring continued at r.t. overnight. Solvent was removed in vacuo and the residue dissolved in EtOAc. The EtOAc solution was washed with brine (×2), dried (MgSO$_4$), and concentrated in vacuo. Purification by column chromatography (silica, 10% EtOAc in DCM) gave the title compound (240 mg, 40%). δH (CDCl$_3$) 8.20 (1H, d, J 8.8 Hz), 7.82 (1H, d, J 9.7 Hz), 7.70 (1H, d, J 2.0 Hz), 7.55 (1H, d, J 3.7 Hz), 7.37 (1H, dd, J 8.8, 2.0 Hz), 6.80 (1H, d, J 3.7 Hz), 6.75 (1H, d, J 9.7 Hz), 4.30 (2H, q, J 7.1 Hz), 3.21 (3H, s), 1.31 (3H, t, J 7.1 Hz).

Intermediate 28

Ethyl 3-bromo-7-(1-methyl-1H-indol-5-yl)-6-oxo-6,7-dihydrothieno[2,3-b]pyridine-2-carboxylate From Intermediate 26 and methyl iodide by the method of Intermediate 27. δH (CDCl$_3$) 7.77 (1H, d, J 9.7 Hz), 7.56 (1H, s), 7.45 (1H, d, J 8.6 HZ), 7.11-7.07 (2H, m), 6.68 (1H, d, J 9.7 Hz), 6.51 (1H, s), 4.21 (2H, q, J 7.1 Hz), 3.80 (3H, s), 1.22 (3H, t, J 7.1 Hz). LCMS (ES$^+$) RT 3.84 minutes, 4.32 (M+H)$^+$.

Intermediate 29

Ethyl 3-bromo-7-(cyclopropylmethyl)-6-oxo-6,7-dihydrothieno[2,3-b]pyridine-2-carboxylate Sodium hydride (60% in mineral oil) (3.27 g, 81.4 mmol) was added in portions to a solution of Intermediate 4 (22.3 g, 74 mmol) in DMF (300 mL) at 0° C. The mixture was stirred at r.t. for 30 min then cyclopropylmethyl bromide (10 g, 74 mmol) was added slowly and the mixture heated at 60° C. overnight. The DMF was removed in vacuo and the residue partitioned between EtOAc and brine. The organic phase was dried (MgSO$_4$) and concentrated in vacuo. Purification by column chromatography (silica, 0% to 10% EtOAc in DCM) gave the title compound as a yellow solid (12.5 g, 47%). δH (CDCl$_3$) 7.57 (1H, d, J 9.5 Hz), 6.47 (1H, d, J 9.5 Hz), 4.22 (2H, q, J 7.0 Hz), 3.87 (2H, d, J 7.1 Hz), 1.26-1.19 (4H, m), 0.43-0.37 (4H, m). LCMS (ES$^+$) RT 3.80 minutes, 357 (M+H)$^+$.

Intermediate 30

3-Bromo-7-(cyclopropylmethyl)-6-oxo-6,7-dihydrothieno[2,3-b]pyridine-2-carbonitrile From Intermediate 8 by the method of Intermediate 29. Off-white solid. δH (CDCl$_3$) 7.67 (1H, d, J 9.6 Hz), 6.68 (1H, d, J 9.6 Hz), 4.02 (2H, d, J 7.1 Hz), 1.36-1.23 (1H, m), 0.75-0.51 (4H, m). LCMS (ES$^+$) RT 3.45 minutes, 309.0 (M+H)$^+$.

Intermediate 31

Ammonium 3-anilino-7-(cyclopropylmethyl)-6-oxo-6,7-dihydrothieno[2,3-b]pyridine-2-carboxylate

A solution of Example 44 (1.38 g, 3.75 mmol) and NaOH (160 mg, 4.0 mmol) in EtOH (50 mL) and water (20 mL) was heated at reflux for 2 h. The bulk of the EtOH was removed in vacuo and water (30 mL) added. The solution was treated with 10% $NH_4Cl$ aq (100 mL) and cooled. The precipitate was filtered off and dried to give the title compound as an off-white solid (1.15 g, 90%). δH (DMSO-d6) 7.03-6.98 (2H, m), 6.91 (1H, d, J 9.5 Hz), 6.72-6.68 (3H, m), 6.02 (1H, d, J 9.5 Hz), 3.70 (2H, d, J 7.0 Hz), 1.16-1.03 (1H, m), 0.32-0.24 (4H, m).

Intermediate 32

Ethyl 3-bromo-6-(cyclopropylmethoxy)thieno[2,3-b]pyridine-2-carboxylate

A mixture of intermediate 4 (5.0 g, 16.5 mmol), caesium carbonate (5.39 g, 16.5 mmol) and cyclopropylmethyl bromide (1.58 mL, 16.5 mmol) in DMF (150 mL) was heated at 90° C. for 3 days. EtOAc was added and the solution washed with brine, dried ($MgSO_4$) and concentrated in vacuo. Purification by column chromatography (silica, 20% EtOAc in hexane) gave the title compound (2.64 g, 45%). δH ($CDCl_3$) 7.95 (1H, d, J 8.85 Hz), 6.81 (1H, d, J 8.88 Hz), 4.34 (2H, q, J 7.2 Hz), 4.18 (2H, d, J 8.8 Hz), 1.35 (3H, t, J 7.1 Hz), 1.26-1.22 (1H, m), 0.58 (2H, dd, J 4.8, 5.4 Hz), 0.31-0.27 (2H, m). LCMS ($ES^+$) RT 5.43 minutes, 357 $(M+H)^+$

Intermediate 33

Ethyl 3-anilino-6-(cyclopropylmethoxy)thieno[2,3-b]pyridine-2-carboxylate

A mixture of Intermediate 32 (2.0 g, 5.6 mmol), aniline (0.61 mL, 6.72 mmol), caesium carbonate (2.55 g, 7.8 mmol), BINAP (690 mg, 20 mol %) and tris(dibenzylideneacetone)dipalladium(0) (510 mg, 10 mol %) in toluene (50 mL) was heated at reflux for 3 days. Brine was added and the mixture extracted with EtOAc. The organic extract was dried ($MgSO_4$) and concentrated in vacuo. Purification by column chromatography (silica, 5% EtOAc in hexane) gave the title compound (1.8 g, 86%). δH ($CDCl_3$) 8.72 (1H br s), 7.29-7.26 (2H, m), 7.18-7.13 (2H, m), 6.93-7.06 (3H, m), 6.39 (1H, d, J 9.01 Hz), 4.22 (2H, q, J 7.1 Hz), 4.05 (2H, d, J 7.2 Hz), 1.26 (3H, t, J 7.1 Hz), 0.48-0.46 (2H, m), 0.25-0.23 (2H, m).

Intermediate 34

Ethyl 3-anilino-6-oxo-6,7-dihydrothieno[2,3-b]pyridine-2-carboxylate

Intermediate 33 (1.8 g, 4.9 mmol) was dissolved in MeOH (100 mL), conc. HCl aq (10 mL) was added and the mixture heated at reflux for 6 h. The reaction mixture was extracted with $CHCl_3$ and the organic phase washed with brine, dried ($MgSO_4$) and concentrated in vacuo to give the title compound as a yellow solid (1.3 g, 84%). δH ($CDCl_3$) 8.75 (1H, brs), 7.34-7.20 (4H, m), 7.18-7.02 (2H, m), 6.26 (1H, d, J 9.63 Hz), 4.25 (2H, q, J 7.1 Hz), 1.29 (3H, t, J 7.1 Hz). LCMS ($ES^+$) RT 3.296 minutes, 314.9 $(M+H)^+$

Intermediate 35

Ethyl 3-bromo-6-oxo-7-(3-thienyl)-6,7-dihydrothieno[2,3-b]pyridine-2-carboxylate

A mixture of intermediate 4 (2.36 g, 7.5 mmol), 2-thiophene boronic acid (2.0 g, 15 mmol) and copper (II) acetate (1.41 g, 7.5 mmol) in pyridine (3.7 mL) was stirred at r.t. for 3 days. The mixture was diluted with DCM, washed with 2M HCl aq, dried ($MgSO_4$) and concentrated in vacuo. Purification by column chromatography (silica, 50% EtOAc in hexane) gave the title compound (270 mg). δH ($CDCl_3$) 7.83 (1H, d, J 9.6 Hz), 7.60-7.58 (2H, m), 7.18-7.16 (1H, m), 6.68 (1H, d, J 9.6 Hz), 4.31 (2H, q, J 7.1 Hz), 1.32 (3H, t, J 7.1 Hz). LCMS ($ES^+$) 386 $(M+H)^+$

Intermediate 36

Ethyl 3-[(4-fluoro-3-methylphenyl)amino]-6-(cyclopropylmethoxy)thieno[2,3-b]pyridine-2-carboxylate

From Intermediate 32 and 4-fluoro-3-methylaniline by the method of Intermediate 33. White solid. δH ($CDCl_3$) 8.64 (1H, br s), 7.24-7.13 (1H, m), 6.82-6.75 (3H, m), 6.40 (1H, d, J 9.0 Hz), 4.23 (2H, q, J 7.2 Hz), 4.11 (2H, d, J 7.2 Hz), 2.11 (3H, s), 1.27 (3H, t, J 7.2 Hz), 1.20-1.11 (1H, m), 0.54-0.48 (2H, m), 0.26-0.20 (2H, m).

Intermediate 37

Ethyl 3-[(4-fluoro-3-methylphenyl)amino]-6-oxo-6,7-dihydrothieno[2,3-b]pyridine-2-carboxylate

From Intermediate 36 by the method of Intermediate 34. δH ($CDCl_3$) 7.18-7.13 (3H, m), 6.95-6.84 (3H, m), 6.39 (1H, d, J 9.6 Hz), 4.26 (2H, q, J 7.2 Hz), 2.19 (3H, s), 1.30 (3H, t, J 7.2 Hz). LCMS ($ES^+$) RT 3.585 minutes, 346 $(M+H)^+$

Intermediate 38

3-[(6-Methyl-1-oxidopyridin-2-yl)amino]-6-oxo-7-phenyl-6,7-dihydrothieno[2,3-b]pyridine-2-carbonitrile

Sodium hydride (330 mg, 60% in mineral oil, 8.25 mmol) was added to a suspension of Intermediate 11 (2 g, 7.5 mmol) in THF (150 mL) and the mixture then heated to 70° C. for 5 min. 6-Chloropicoline N-oxide (1.13 g, 8.25 mmol) was added at r.t. and the mixture heated at 70° C. for 24 h. The solvent was removed in vacuo. Purification of the residue by column chromatography (silica, 50% THF in DCM to 40% MeOH in DCM) gave the title compound (1.54 g, 55%). LCMS ($ES^+$) RT 2.79 minutes, 375 $(M+H)^+$.

Intermediate 39

Ethyl 3-bromo-7-[4-(methylthio)phenyl]-6-oxo-6,7-dihydrothieno[2,3-b]pyridine-2-carboxylate

From Intermediate 4 and 4-thiomethylboronic acid by the method of Intermediate 5. δH ($CDCl_3$) 7.76 (1H, d, J 9.7 Hz), 7.36 (2H, d, J 8.7 Hz), 7.23 (2H, d, J 8.7 Hz), 6.65 (1H, d, J 9.7 Hz), 4.26 (2H, q, J 7.1 Hz), 2.48 (3H, s), 1.27 (3H, t, J 7.1 Hz). LCMS ($ES^+$) RT 3.91 minutes, 426 $(M+H)^+$.

Intermediate 40

Ethyl 3-bromo-7-(4-formylphenyl)-6-oxo-6,7-dihydrothieno[2,3-b]pyridine-2-carboxylate From Intermediate 4 and 4-formylphenylboronic acid by the method of Intermediate 5. δH (CDCl$_3$) 10.03 (1H, s), 8.12-8.0 (2H, m), 7.85-7.78 (1H, m), 7.54 (2H, d, J 9.4 Hz), 6.66 (1H, d, J 9.7 Hz), 4.25 (2H, q, J 7.1 Hz), 1.262 (3H, t, J 7.1 Hz). LCMS (ES$^+$) RT 3.450 minutes, 408 (M+H)$^+$.

Intermediate 41

Ethyl 3-bromo-6-oxo-7-[4-(pyrrolidin-1-ylmethyl)phenyl]-6,7-dihydrothieno[2,3-b]pyridine-2-carboxylate A mixture of Intermediate 40 (150 mg, 0.36 mmol), pyrrolidine (0.03 mL, 0.36 mmol) and sodium triacetoxyborohydride (117 mg, 0.55 mmol) in 1,2-dichloroethane (5 mL) was heated at reflux overnight. The mixture was washed with sat NaHCO$_3$ aq. The organic phase was dried (MgSO$_4$) and concentrated in vacuo. Purification by column chromatography (silica, 5% MeOH in DCM) gave the title compound (51 mg, 31%). δH (CDCl$_3$) 7.84 (2H, d, J 9.6 Hz), 7.64 (2H, m), 7.30 (2H, m), 6.73 (2H, d, J 9.6 Hz), 4.13 (2H, q, J 7.1 Hz), 2.85 (1H, t, J 5.8 Hz), 3.19 (5H, br s), 1.35 (3H, t, J 7.1 Hz). LCMS (ES$^+$) RT 2.367 minutes, 463 (M+H)$^+$.

Intermediate 42

Ethyl 3-bromo-7-(4-{[tert-butyl(dimethyl)silyl]oxy}phenyl)-6-oxo-6,7-dihydrothieno[2,3-b]pyridine-2-carboxylate From Intermediate 4 and (4{[tert-butyl(dimethyl)silyl]oxy}phenyl)boronic acid by the method of Intermediate 5. δH (CDCl$_3$) 7.75 (1H, d, J 9.6 Hz), 7.17 (2H, d, J 8.8 Hz), 6.96 (2H, d, J 8.8 Hz), 6.64 (1H, d, J 9.6 Hz), 4.26 (2H, q, J 7.1 Hz), 1.27 (3H, t, J 7.1 Hz), 0.94 (9H, s), 0.20 (6H, s). LCMS (ES$^+$) RT 3.405 minutes, 508/510 ($^{79}$Br/$^{81}$Br) (M+H)$^+$.

Intermediate 43

Ethyl 7-(4-{[tert-butyl(dimethyl)silyl]oxy}phenyl)-3-[(2,4-difluorophenyl)amino]-6-oxo-6,7-dihydrothieno[2,3-b]pyridine-2-carboxylate From Intermediate 42 and 2,4-difluoroaniline by the method of Example 1. δH (CDCl$_3$) 8.45 (1H, br s), 7.20-7.10 (3H, m), 7.00-6.77 (5H, m), 6.29 (1H, d, J 9.8 Hz), 4.20 (2H, q, J 7.1 Hz), 1.23 (3H, t, J 7.1 Hz), 0.94 (9H, s), 0.20 (6H, s). LCMS (ES$^+$) RT 3.890 minutes, 557 (M+H)$^+$.

Intermediate 44

Ethyl 3-[(2,4-difluorophenyl)amino]-7-(4-hydroxyphenyl)-6-oxo-6,7-dihydrothieno[2,3-b]pyridine-2-carboxylate Tetra butyl ammonium fluoride (483 mg, 1.85 mmol) was added to a solution of Intermediate 43 (1.0 g, 1.80 mmol) in THF (20 mL). After 15 min the reaction mixture was partitioned between EtOAc (50 mL) and water (50 mL). The organic phase was washed with brine, dried (MgSO$_4$) and concentrated in vacuo to give the title compound (745 mg, 95%). δH (DMSO-d6) 8.65 (1H, br s), 7.50-7.27 (4H, m), 7.20-7.10 (2H, m), 6.99 (2H, d, J 8.8 Hz), 6.40 (1H, d, J 9.8 Hz), 4.19 (2H, q, J 7.1 Hz), 1.21 (3H, t, J 7.1 Hz). LCMS (ES$^+$) RT 3.590 minutes, 443 (M+H)$^+$.

Intermediate 45

Ethyl 7-[4-(2-bromoethoxy)phenyl]-3-[(2,4-difluorophenyl)amino]-6-oxo-6,7-dihydrothieno[2,3-b]pyridine-2-carboxylate Di-isopropyl azodicarboxylate (0.334 mL, 1.70 mmol) was added to a solution of Intermediate 44 (500 mg, 1.13 mmol) and triphenylphosphine (445 mg, 1.70 mmol) in a mixture of DCM (10 mL) and THF (5 mL). 2-Bromoethanol (0.125 mL, 1.70 mmol) was added and the mixture stirred for 3 days. Water (30 mL) was added and the organic phase dried (MgSO$_4$) and concentrated in vacuo. Purification by column chromatography (silica, 5% EtOAc in DCM) gave the title compound (375 mg, 60%). δH (CDCl$_3$) 8.40 (1H, br s), 7.18-7.11 (2H, m), 7.03-6.87 (4H, m), 6.81-6.68 (2H, m), 6.19 (1H, d, J 9.8 Hz), 4.19 (2H, t, J 6.2 Hz), 4.09 (2H, q, J 7.1 Hz), 3.50 (2H, t, J 6.2 Hz), 1.12 (3H, t, J=7.1 Hz). LCMS (ES$^+$) RT 4.206 minutes, 549/551 ($^{79}$Br/$^{81}$Br) (M+H)$^+$.

Intermediate 46

Ethyl 3-bromo-6-oxo-7-(4-vinylphenyl)-6,7-dihydrothieno[2,3-b]pyridine-2-carboxylate From Intermediate 4 and (4-vinylphenyl)boronic acid by the method of Intermediate 5. δH (CDCl$_3$) 7.95 (1H, d, J 9.7 Hz), 7.76-7.73 (2H, m), 7.47-7.44 (2H, m), 6.90 (1H, dd, J 17.6, 11.1 Hz), 6.83 (1H, d, J 9.7 Hz), 5.96 (1H, dd, J 17.6, 0.4 Hz), 5.51 (1H, d, J 11.1 Hz), 4.43 (2H, q, J 7.1 Hz), 1.44 (3H, t, J 7.1 Hz). LCMS (ES$^+$) RT 3.947 minutes, 404/406 ($^{79}$Br/$^{81}$Br) (M+H)$^+$.

Intermediate 47

3-Bromo-7-(4-{[tert-butyl(dimethyl)silyl]oxy}phenyl)-6-oxo-6,7-dihydrothieno[2,3-b]pyridine-2-carbonitrile From Intermediate 8 and (4-{[tert-butyl(dimethyl)silyl]oxy}phenyl)boronic acid by the method of Intermediate 5. δH (CDCl$_3$) 7.52 (1H, d, J 9.6 Hz), 7.05-6.99 (2H, m), 6.84-6.79 (2H, m), 6.54 (1H, d, J 9.6 Hz), 0.80 (9H, s), 0.05 (6H, s). LCMS (ES$^+$) RT 4.65 minutes, 461/463 ($^{79}$Br/$^{81}$Br) (M+H)$^+$.

Intermediate 48

7-(4-{[tert-Butyl(dimethyl)silyl]oxy}phenyl)-3-[(2,4-difluorophenyl)amino]-6-oxo-6,7-dihydrothieno[2,3-b]pyridine-2-carbonitrile From Intermediate 47 and 2,4-difluoroaniline by the method of Example 1. δH (CDCl$_3$) 7.14 (1H, d, J 9.7 Hz), 7.04-7.00 (2H, m), 6.95-6.87 (1H, m), 6.80-6.63 (4H, m), 6.32 (1H, d, J 9.7 Hz), 5.93 (1H, br s), 0.78 (9H, s), 0.04 (6H, s). LCMS (ES$^+$) RT 4.81 minutes, 510 (M+H)$^+$.

Intermediate 49

3-[(2,4-Difluorophenyl)amino]-7-(4-hydroxyphenyl)-6-oxo-6,7-dihydrothieno[2,3-b]pyridine-2-carbonitrile From Intermediate 48 by the method of Intermediate 44. δH (d$_3$-MeOD) 8.14 (1H, d, J 9.6 Hz), 7.54-7.32 (3H, m), 7.22-7.06 (4H, m), 6.74 (1H, d, J 9.6 Hz). LCMS (ES$^+$) RT 3.113 minutes, 396 (M+H)$^+$.

Intermediate 50

3-[(2,4-Difluorophenyl)amino]-7-{4-[(2,2-dimethyl-1,3-dioxolan-4-yl)methoxy]phenyl}-6-oxo-6,7-dihydrothieno[2,3-b]pyridine-2-carbonitrile

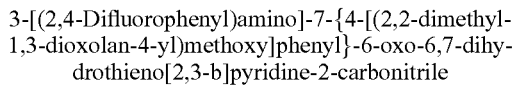

A mixture of Intermediate 49 (370 mg, 0.94 mmol), (R)-(2,2-dimethyl-1,3-dioxolan-4-yl)methyl 4-methylbenzenesulfonate (538 mg. 1.88 mmol) and caesium carbonate (365 mg, 1.1 mmol) in DMF (2 mL) was heated at 80° C. for 3 days. The mixture was partitioned between EtOAc and brine. The Organic phase was dried (MgSO$_4$) and concentrated in vacuo. Purification by column chromatography (silica, 20% EtOAc in DCM) gave the title compound (54 mg). δH (CDCl$_3$) 7.32-7.20 (3H, m), 7.12-7.02 (3H, m), 6.93-6.78 (2H, m), 6.49 (1H, d, J 9.7 Hz), 6.12 (1H, s), 4.49-4.41 (1H, m), 4.15-3.84 (4H, m), 1.41 (3H, s), 1.35 (3H, s). LCMS (ES$^+$) RT 3.516 minutes, 510 (M+H)$^+$.

Intermediate 51

Ethyl 3-bromo-7-(2-nitrophenyl)-6-oxo-6,7-dihydrothieno[2,3-b]pyridine-2-carboxylate Sodium hydride (440 mg, 60% in mineral oil, 11 mmol) was added portion-wise to a suspension of intermediate 4 (3.02 g, 10 mmol) in DMF (40 mL) at r.t. After 15 min, 2-fluoronitrobenzene (2.11 mL, 20 mmol) was added and the mixture heated at 90° C. for 4 days. The DMF was removed in vacuo and the residue purified by column chromatography (silica, 0% to 3% THF in DCM). The title compound was obtained as a yellow solid (1.36 g, 32%). δH (DMSO-d6) 8.37 (1H, dd, J 1.4, 8.1 Hz), 8.10-8.06 (1H, m), 8.01-7.92 (3H, m), 6.71 (1H, d, J 9.7 Hz), 4.27 (2H, q, J 7.1 Hz), 1.24 (3H, t, J 7.1 Hz). LCMS (ES$^+$) RT 3.644 minutes, 424.9 (M+H)$^+$.

Intermediate 52

Sodium 3-[(2,4-difluorophenyl)amino]-7-(2-nitrophenyl)-6-oxo-6,7-dihydrothieno[2,3-b]pyridine-2-carboxylate

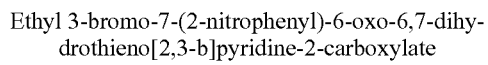

A mixture of Example 95 (405 mg, 0.86 mmol) and sodium hydroxide (38 mg, 0.946 mmol) in water (5 mL) and EtOH (10 mL) was heated at reflux for 90 min. The solvent was removed in vacuo to give a brown solid, crude title compound. This was used in the next step without purification. LCMS (ES$^+$) RT 3.262 minutes, 443.8 (M+H)$^+$.

Intermediate 53

2-Amino-4-methyl-6-oxo-1-phenyl-1,6-dihydropyridine-3-carbonitrile

The title compound was prepared according to Habashi et al, Liebigs Ann. Chem. 1986, 1632-1638. δH (DMSO-d6) 7.63-7.45 (3H, m), 7.25 (2H, m), 6.70 (2H, br s), 5.68 (1H, s), 2.18 (3H, s). LCMS (Conditions B) (ES$^+$) RT 1.97 minutes, 226 (M+H)$^+$.

Intermediate 54

2,5-Dibromo-4-methyl-6-oxo-1-phenyl-1,6-dihydropyridine-3-carbonitrile

To a stirred mixture of copper (II) bromide (10.35 g) and tert. butyl nitrite (6.6 mL) in acetonitrile (75 mL), was added Intermediate 53 (7.45 g) portionwise over 15 minutes. The resulting mixture was stirred at ambient temperature for a further 2 hours when it was poured into 2M HCl(aq) (100 mL). Ethyl acetate (150 mL) was added and the mixture stirred for approximately one hour. After this time, the layers were separated and the aqueous phase was re-extracted with ethyl acetate (50 mL). The combined organic extracts were washed with 2M HCl(aq) (100 mL). Any insoluble material was removed by filtration and the resulting filtrate was washed with brine and then concentrated in vacuo. The residue was purified by chromatography on silica eluting with DCM to give the title compound as a pale green solid (5.63 g). δH (CDCl$_3$) 7.55 (3H, m), 7.17 (2H, m), 2.65 (3H, s). LCMS (Conditions B) (ES$^+$) RT 3.59 minutes, 369 (M+H)$^+$.

Intermediate 55

Ethyl 3-amino-5-bromo-4-methyl-6-oxo-7-Phenyl-6,7-dihydrothieno[2,3-b]pyridine-2-carboxylate

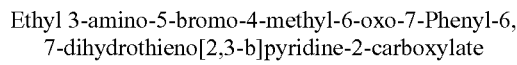

A mixture of Intermediate 54 (5.6 g), ethyl 2-mercaptoacetate (2.1 mL) and sodium carbonate (1.70 g) in absolute ethanol (56 mL) was heated at reflux for 2.5 hours. After this time, the reaction was cooled to ambient temperature, water (56 mL) was added and the resulting mixture stirred for an additional hour. The product was collected by filtration, washed with water and dried in vacuo to give the title compound as an off-white solid (5.83 g). δH (CDCl$_3$) 7.55 (3H, m), 7.35 (2H, m), 6.15 (2H, br s), 4.25 (2H, q, J 7.0 Hz), 2.86 (3H, s), 1.28 (3H, t, J 7.0 Hz). LCMS (Conditions B) (ES$^+$) RT 3.77 minutes, 407 (M+H)$^+$.

Intermediate 56

Ethyl 3-amino-4-methyl-6-oxo-7-phenyl-6,7-dihydrothieno[2,3-b]pyridine-2-carboxylate

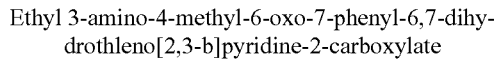

To a solution of Intermediate 55 (5.83 g) in DCM (650 mL) containing triethylamine (4 mL), was added 5% palladium on carbon (Johnson Matthey type 38H paste; 0.58 g) and the resulting mixture was stirred under a hydrogen atmosphere until hydrogen uptake ceased. The catalyst was removed by filtration and the organic phase washed with water (twice), and then evaporated in vacuo to leave the title compound as a white solid (4.73 g). δH (CDCl$_3$) 7.57 (3H, m), 7.35 (2H, m), 6.36 (1H, s), 6.09 (2H, br s), 4.25 (2H; q, J 7.0 Hz), 2.63 (3H, s), 1.26 (3H, t, J 7.0 Hz). LCMS (Conditions B) (ES$^+$) RT 3.41 minutes, 329 (M+H)$^+$.

Intermediate 57

Ethyl 3-bromo-4-methyl-6-oxo-7-phenyl-6,7-dihydrothieno[2,3-b]pyridine-2-carboxylate

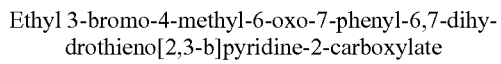

To a stirred mixture of copper (II) bromide (2.9 g) and tert. butyl nitrite (1.84 mL) in acetonitrile (90 mL), was added Intermediate 56 (3.05 g) portionwise over 15 minutes. The resulting mixture was stirred at ambient temperature for a further 0.5 h when 2M HCl(aq) (150 mL) was added. The reaction mixture was extracted with ethyl acetate (twice) and the combined organic extracts were washed with water (75 mL), brine (100 mL) and then dried (Na$_2$SO$_4$) and evaporated in vacuo. The residue was purified by chromatography on silica eluting with DCM to give the title compound as an off-white solid (1.23 g). δH (CDCl$_3$) 7.63 (3H, m), 7.35 (2H, m), 6.53 (1H, s), 4.30 (2H, q, J 7.0 Hz), 2.79 (3H, s), 1.32 (3H, t, J 7.0 Hz). LCMS (Conditions B) (ES$^+$) RT 3.98 minutes, 392 (M+H)$^+$.

Intermediate 58

3-[(2,4-Difluorophenyl)amino]-7-phenylthieno[2,3-b]pyridin-6(7H)-one

From Intermediate 67 by the method of Example 15. δH (CDCl$_3$) (DMSO-d6) 7.94 (1H, d, J 9.4 Hz), 7.64-7.53 (3H, m), 7.46 (2H, m), 7.45 (1H, m), 7.20 (1H, m), 6.99 (1H, m), 6.48 1H, d, J 9.4 Hz), 5.74 (1H, s). LCMS (ES$^+$) RT 3.54 minutes, 354.9 (M+H)$^+$.

Intermediate 59 tert-Butyl (2,4-difluorophenyl)(6-oxo-7-phenyl-6,7-dihydrothieno[2,3-b]pyridin-3-yl)carbamate Sodium bis(trimethylsilyl)amide (6.0 mL, 1.0M in THF, 6 mmol) was added to a solution of Intermediate 58 (2.0 g, 5.65 mmol) in THF (50 mL) at 0° C. After 30 min, di-tert-butyl dicarbonate (1.36 g, 6.22 mmol) was added and the mixture stirred at r.t. for 1 h. The reaction mixture was partitioned between EtOAc and brine. The aqueous phase was extracted with EtOAc (×3), the combined organic extracts washed with brine, dried (MgSO$_4$) and concentrated in vacuo. Purification by column chromatography (silica, 10% EtOAc in DCM) gave the title compound (1.2 g, 47%). δH (CDCl$_3$) 7.45 (1H, d, J 9.5 Hz), 7.43-7.30 (3H, m), 7.22-7.19 (2H, m), 7.08-7.03 (1H, m), 6.76-6.65 (2H, m), 6.49-6.45 (2H, m), 1.26 (9H, s). LCMS (ES$^+$) RT 3.79 minutes, 455 (M+H)$^+$.

Intermediate 60 tert-Butyl [2-(aminosulfonyl)-6-oxo-7-phenyl-6,7-dihydrothieno[2,3-b]pyridin-3-yl](2,4-difluorophenyl)carbamate n-Butyl lithium (0.18 mL of a 2.5M solution in hexanes, 0.44 mmol) was added to a solution of Intermediate 59 (200 mg, 0.44 mmol) in THF (10 mL) at −78° C. After 3 min, sulfur dioxide gas was bubbled through the solution for 2 min. The reaction mixture was allowed to warm to r.t. and solvents were removed in vacuo. The residue was dissolved in DCM (15 mL) and N-chlorosuccinimide (60 mg, 0.44 mmol) was added. After 20 min at r.t. aqueous ammonia (conc) (5 mL) was added and the mixture stirred for a further 10 min. The mixture was diluted with DCM and washed with brine. The organic phase was dried (MgSO$_4$) and concentrated in vacuo. Purification by column chromatography (silica, 10% EtOAc in DCM) gave the title compound (50 mg, 21%). δH (CDCl$_3$) 7.42-7.36 (3H, m), 7.23-7.16 (4H, m), 6.81-6.77 (1H, m), 6.75-6.63 (1H, m), 6.39 (1H, d, J 10.3 Hz), 5.43 (2H, brs), 1.27 (9H, s). LCMS (ES$^+$) RT 3.58 minutes, 534 (M+H)$^+$.

Intermediate 61

Ethyl 3-bromo-7-[2-(2-methoxyethoxy)ethyl]-6-oxo-6,7-dihydrothieno[2,3-b]pyridine-2-carboxylate Sodium hydride (60% in mineral oil, 240 mg, 6 mmol) was added to a suspension of Intermediate 4 (1.50 g, 4.97 mmol) in DMF (12 mL). After 10 min at r.t., bromomethoxyethoxyethane (1.0 g, 5.5 mmol), was added and the mixture heated at 60° C. for 4 h. The mixture was partitioned between brine (200 mL) and DCM (200 mL). The organic phase was washed with brine (2×100 mL), dried (Na$_2$SO$_4$) and concentrated in vacuo. Purification by column chromatography (silica, 5% to 15% THF in DCM) gave the title compound as a white solid (420 mg, 21%). δH (CDCl$_3$) 7.78 (1H, d, J 9.6 Hz), 6.65 (1H, d, J 9.6 Hz), 4.42 (2H, q, J 7.1 Hz), 7.38-7.34 (2H, m), 3.96-3.07 (2H, m), 3.68-3.64 (2H, m), 3.48-3.45 (2H, m), 3.32 (3H, s), 1.41 (3H, t, J 7.1 Hz).

Intermediate 62

Ethyl 3-bromo-6-oxo-7-(tetrahydro-2H-pyran-2-ylmethyl)-6,7-dihydrothieno[2,3-b]pyridine-2-carboxylate Sodium hydride (60% in mineral oil, 320 mg, 8 mmol) was added to a suspension of Intermediate 4 (2.0 g, 6.67 mmol) in DMF (15 mL). After 10 min at r.t., 2-(bromomethyl)-tetrahydro-2H-pyran (0.895 mL, 7 mmol), was added and the mixture heated at 80° C. for 18 h. The mixture was partitioned between brine (200 mL) and EtOAc (120 mL). The organic phase was washed with brine (3×75 mL), dried (Na$_2$SO$_4$) and concentrated in vacuo. Purification by column chromatography (silica, 0% to 10% EtOAc in DCM) gave the title compound as a white solid (642 mg, 24%). δH (CDCl$_3$) 7.76 (1H, d, J 9.6 Hz), 6.63 (1H, d, J 9.6 Hz), 4.45-4.30 (3H, m), 3.93-3.78 (3H, m), 3.32-3.26 (1H, m), 1.90-1.86 (1H, m), 1.77-1.74 (1H, m), 1.66-1.38 (4H, m), 1.42 (3H, t, J 7.1 Hz). LCMS (ES$^+$) RT 3.90 minutes, 440.0/402.0 ($^{79}$Br/$^{81}$Br) (M+H)$^+$.

Intermediate 63

Ethyl 3-bromo-7-benzyl-6-oxo-6,7-dihydrothieno[2,3-b]pyridine-2-carboxylate

From Intermediate 4 and benzyl bromide by the method of Intermediate 61. δH (CDCl$_3$) 7.80 (1H, d, J 9.6 Hz), 7.41-7.32 (5H, m), 6.74 (1H, d, J 9.6 Hz), 5.37 (2H, s), 4.38 (2H, q, J 7.1 Hz), 1.40 (3H, t, J 7.1 Hz). LCMS (ES$^+$) RT 3.89 minutes, 392.0/394.0 ($^{79}$Br/$^{81}$Br) (M+H)$^+$.

Intermediate 64

Ammonium 3-anilino-7-benzyl-6-oxo-6,7-dihydrothieno[2,3-b]pyridine-2-carboxylate From Example 102 by the method of Intermediate 31. δH (DMSO-d6) 7.47-7.25 (9H, m), 7.19-7.02 (3H, m), 6.43 (1H, d, J 9.6 Hz), 5.35 (2H, s).

Intermediate 65

Ethyl 3-bromo-7-[4-(dimethylamino)phenyl]-6-oxo-6,7-dihydrothieno[2,3-b]pyridine-2-carboxylate From Intermediate 4 and 4-(dimethylamino)phenylboronic acid by the method of Intermediate 5. Light tan solid. δH (CDCl$_3$) 7.68 (1H, d, J 9.7 Hz), 7.08 (2H, d, J 9.0 Hz), 6.71 (2H, d, J 9.0 Hz), 6.59 (1H, d, J 9.7 Hz), 4.20 (2H, q, J 7.1 Hz), 2.93 (6H, s), 1.21 (3H, t, J 7.1 Hz).

Intermediate 66

Ammonium 3-anilino-7-[4-(dimethylamino)phenyl]-6-oxo-6,7-dihydrothieno[2,3-b]pyridine-2-carboxylate From Example 105 by the method of Example 31. δH (DMSO-d6) 7.26-7.17 (6H, m), 6.93-6.89 (2H, m), 6.83 (2H, d, J 9.0 Hz), 6.26 (1H, d, J 9.6 Hz), 2.97 (6H, s). LCMS (ES$^+$) RT 3.30 minutes, 406 (M+H)$^+$.

Intermediate 67

Ammonium 3-[(2,4-difluorophenyl)amino]-6-oxo-7-phenyl-6,7-dihydrothieno[2,3-b]pyridine-2-carboxylate From Example 12 by the method of Intermediate 31. δH (DMSO-d6) 9.75 (1H, br s), 7.75-7.50 (3H, m), 7.49-7.37 (2H, m), 7.31-7.27 (2H, m), 7.00-6.80 (2H, br m), 6.35-6.31 (1H, br m). LCMS (ES+) RT 3.25 minutes, no (M+H)+ observed.

Intermediate 68

Ethyl 3-bromo-7-(4-fluorophenyl)-6-oxo-6,7-dihydrothieno[2,3-b]pyridine-2-carboxylate From Intermediate 4 and 4-fluorophenylboronic acid by the method of Intermediate 5. White solid. δH (CDCl$_3$) 7.84 (1H, d, J 9.7 Hz), 7.41-7.37 (2H, m), 7.32-7.25 (2H, m), 6.72 (1H, d, J 9.7 Hz), 4.33 (2H, q, J 7.1 Hz), 1.34 (3H, t, J 7.1 Hz). LCMS (ES+) RT 3.729 minutes, 397.8 (M+H)+.

Intermediate 69

Ethyl 3-bromo-7-(4-chlorophenyl)-6-oxo-6,7-dihydrothieno[2,3-b]pyridine-2-carboxylate From Intermediate 4 and 4-chlorophenylboronic acid by the method of Intermediate 5. δH (CDCl$_3$) 7.86 (1H, d, J 9.6 Hz), 7.60 (2H, d, J 8.5 Hz), 7.37 (2H, d, J 8.5 Hz), 6.74 (1H, d, J 9.6 Hz), 4.35 (2H, q, J 7.1 Hz), 1.36 (3H, t, J 7.1 Hz). LCMS (ES+) RT 3.937 minutes, 413 (M+H)+.

Intermediate 70

Ethyl 3-bromo-7-(3-methylphenyl)-6-oxo-6,7-dihydrothieno[2,3-b]pyridine-2-carboxylate From Intermediate 4 and 3-methylphenylboronic acid by the method of Intermediate 5. δH (CDCl$_3$) 7.85 (1H, d, J 9.6 Hz), 7.51-7.48 (1H, m), 7.38-7.27 (1H, m), 7.29 (2H, br m), 6.75 (1H, d, J 9.6 Hz), 4.34 (2H, q, J 7.1 Hz), 2.46 (3H, s), 1.35 (3H, t, J 7.1 Hz). LCMS (ES+) RT 3.865 minutes, 393 (M+H)+.

Intermediate 71

3-[(3-(trifluoromethyl)phenyl)amino]-6-oxo-7-phenyl-6,7-dihydrothieno[2,3-b]pyridine-2-carbonitrile From Intermediate 9 and 3-(trifluoromethyl)aniline by the method of Example 1. LCMS (ES+) RT 3.63 minutes, 412 (M+H)+.

Intermediate 72

3-Bromo-7-(4-fluorophenyl)-6-oxo-6,7-dihydrothieno[2,3-b]pyridine-2-carbonitrile From Intermediate 8 and 4-fluorophenylboronic acid by the method of Intermediate 5. δH (DMSO-d6) 8.1-8.0 (1H, m), 7.8-7.7 (2H, m), 7.65-7.6 (2H, m), 6.9-6.85 (1H, m). LCMS (ES+) RT 3.460 minutes, 350.8 (M+H)+.

Intermediate 73

3-Bromo-7-(4-methoxyphenyl)-6-oxo-6,7-dihydrothieno[2,3-b]pyridine-2-carbonitrile From Intermediate 8 and 4-methoxyphenylboronic acid by the method of Intermediate 5. δH (CDCl$_3$) 7.53 (1H, d, J 9.7 Hz), 7.10-7.05 (2H, m), 6.92-6.87 (2H, m), 6.56 (1H, d, J 9.7 Hz), 3.69 (3H, s). LCMS (ES+) RT 3.452 minutes, 361/363 ($^{79}$Br/$^{81}$Br) (M+H)+.

Intermediate 74

7-(4-Acetylphenyl)-3-bromo-6-oxo-6,7-dihydrothieno[2,3-b]pyridine-2-carbonitrile From Intermediate 8 and 4-acetylphenylboronic acid by the method of Intermediate 5. δH (CDCl$_3$) 7.98 (2H, d, J 8.7 Hz), 7.55 (1H, d, J 9.7 Hz), 7.29 (2H, d, J 8.7 Hz), 6.56 (1H, d, J 9.7 Hz), 2.46 (3H, s). LCMS (ES+) 375 (M+Na)+.

Intermediate 75

Ammonium 3-[(3-chloro-4-fluorophenyl)amino]-6-oxo-7-phenyl-6,7-dihydrothieno[2,3-b]pyridine-2-carboxylate From Example 129 by the method of Intermediate 31. δH (DMSO-d6) 7.65-7.59 (3H, m), 7.52-7.50 (2H, m), 7.34-7.29 (2H, m), 7.10-7.21 (3H, br m), 6.99-6.95 (1H, m), 6.40 (1H, d, J 9.6 Hz). LCMS (ES+) RT 3.363 minutes.

Intermediate 76

Ammonium 3-[(4-fluorophenyl)amino]-6-oxo-7-phenyl-6,7-dihydrothieno[2,3-b]pyridine-2-carboxylate From Example 127 by the method of Intermediate 31.

Intermediate 77

Ammonium 3-[(3-chlorophenyl)amino]-6-oxo-7-phenyl-6,7-dihydrothieno[2,3-b]pyridine-2-carboxylate From Example 3 by the method of Intermediate 31. δH (DMSO-d6) 7.65-7.57 (3H, m), 7.51-7.49 (2H, m), 7.34 (1H, d, J 9.6 Hz), 7.28-7.22 (1H, m), 7.00-6.99 (1H, m), 6.96-6.89 (2H, m), 6.39 (1H, d, J 9.6 Hz). LCMS (ES+) RT 3.372 minutes, 396.8 (M+H)+.

Intermediate 78 tert-Butyl (imino{3-[(3-methylphenyl)amino]-6-oxo-7-phenyl-6,7-dihydrothieno[2,3-b]pyridin-2-yl}methyl)carbamate A solution of ethyl magnesium bromide (1M, 2.8 mL, 2.8 mmol) was added to tert-butyl carbamate (328 mg, 2.8 mmol) in ether at r.t. After 10 min, Example 139 (200 mg, 0.56 mmol) was added and the mixture heated at reflux for 1 h. THF (7 mL) was added and the mixture heated at 60° C. for 18 h. Water was added and the mixture was extracted with DCM. The organic phase was dried (Na$_2$SO$_4$) and concentrated in vacuo. Purification by column chromatography (silica, Et$_2$O) gave the title compound as a yellow solid (46 mg). δH (CDCl$_3$) 9.53 (1H, s), 7.58-7.45 (3H, m), 7.34 (2H, d, J 7.7 Hz), 7.19-7.12 (2H, m), 6.88-6.80 (3H, m), 6.29 (1H, d, J 9.7 Hz), 2.27 (3H, s), 1.41 (9H, s). LCMS (ES+) RT 3.343 minutes, 475 (M+H)+.

Intermediate 79

Pentafluorophenyl 3-[(2,4-difluorophenyl)amino]-6-oxo-7-phenyl-6,7-dihydrothieno[2,3-b]pyridine-2-carboxylate CDI (1.42 g, 7.42 mmol) was added to a solution of Intermediate 67 (2.5 g, 6.18 mmol) in DMF (100 mL). After 20 min, pentafluorophenol (1.71 g, 9.27 mmol) was added and the mixture stirred at r.t. overnight. Solvent was removed in vacuo, the residue partitioned between DCM and water and the aqueous phase was extracted with DCM. The combined organics were dried (MgSO$_4$) and concentrated in vacuo. Purification by column chromatography (silica, 20% to 100% EtOAc in hexane) gave the title compound as a white solid (666 mg, 19%). δH (CDCl$_3$) 8.66 (1H, br s), 7.76 (3H, m), 7.58 (2H, m), 7.47 (1H, m), 7.14 (3H, m), 6.54 (1H, d, J 9.9 Hz). LCMS (ES$^+$) RT 4.57 minutes, 564.9 (M+H)$^+$.

Intermediate 80

2-[4-(5,5-Dimethyl-1,3,2-dioxaborinan-2-yl)phenyl]propan-2-ol

A mixture of 2-(4-bromophenyl)propan-2-ol (3.50 g, 16.3 mmol), bis(neopentylglycolato)diboron (4.05 g, 17.93 mmol), KOAc (2.40 g, 24.45 mmol) and [1,1′-bis(diphenylphosphino)ferrocene]dichloropalladium (II) (665 mg, 0.815 mmol) in DMF (25 mL) was heated at 60° C. for 18 h. The DMF was removed in vacuo and the residue azeotroped with toluene (×3). The residue was dissolved in Et$_2$O, filtered, and the filtrated concentrated in vacuo to give the title compound as a brown solid (3.08 g). δH (CDCl$_3$) 7.70 (2H, d, J 9.8 Hz), 7.41 (2H, d, J 9.8 Hz), 3.69 (4H, s), 1.51 (6H, s), 0.95 (6H, s).

Intermediate 81

Ethyl 3-bromo-7-[4-(1-hydroxy-1-methylethyl)phenyl]-6-oxo-6,7-dihydrothieno[2,3-b]pyridine-2-carboxylate From Intermediate 4 and Intermediate 80 by the method of Intermediate 5. White solid. δH (CDCl$_3$) 7.77 (1H, d, J 9.7 Hz), 7.66 (2H, d, J 8.5 Hz), 7.28 (2H, d, J 8.5 Hz), 6.66 (1H, d, J 9.6 Hz), 4.26 (2H, q, J 7.1 Hz), 1.75 (1H, br s), 1.58 (6H, s), 1.27 (3H, t, J 7.1 Hz). LCMS (ES$^+$) RT 3.41 minutes, 438 (M+H)$^+$.

Intermediate 82

Ethyl 3-bromo-7-{4-[(tert-butoxycarbonyl)amino]phenyl}-6-oxo-6,7-dihydrothieno[2,3-b]pyridine-2-carboxylate From Intermediate 4 and {4-[(tert-butoxycarbonyl)amino]phenyl}boronic acid by the method of Intermediate 5. δH (CDCl$_3$) 8.85 (1H, d, J 8.8 Hz), 7.61 (2H, d, J 8.8 Hz), 7.32 (2H, d, J 8.8 Hz), 6.75 (1H, s), 6.73 (1H, d, J 9.6 Hz), 4.34 (2H, q, J 7.1 Hz), 1.56 (9H, s), 1.36 (3H, t, J 7.1 Hz).

Intermediate 83

Ethyl 7-{4-[(tert-butoxycarbonyl)amino]phenyl}-3-[(2,4-difluorophenyl)amino]-6-oxo-6,7-dihydrothieno[2,3-b]pyridine-2-carboxylate From Intermediate 82 and 2,4-difluoroaniline by the method of Example 1. δH (CDCl$_3$) 8.56 (1H, s), 7.78 (2H, d, J 9.8 Hz), 7.45 (2H, d, J 8.6 Hz), 7.35-7.28 (1H, m), 7.20 (1H, d, J 9.8 Hz), 7.14-6.99 (2H, m), 6.84 (1H, s), 6.51 (1H, d, J 9.8 Hz), 4.41 (2H, q, J 7.1 Hz), 1.69 (9H, s), 1.45 (3H, t, J 7.1 Hz). LCMS (ES*) RT 4.288 minutes, 542 (M+H)$^+$.

Intermediate 84

Ethyl 7-(4-aminophenyl)-3-[(2,4-difluorophenyl)amino]-6-oxo-6,7-dihydrothieno[2,3-b]pyridine-2-carboxylate Trifluoroacetic acid (0.5 mL) was added to a solution of Intermediate 83 in DCM (2 mL). After 1 h at r.t., the solvent was removed in vacuo and the residue azeotroped with heptane. The residue was dissolved in DCM and the solution washed with aq NaHCO$_3$. The organic phase was dried (Na$_2$SO$_4$) and concentrated in vacuo. Purification by column chromatography (silica, EtOAc) gave the title compound (72 mg, 82%). δH (CDCl$_3$) 8.30 (1H, s), 7.05-6.97 (3H, m), 6.89 (1H, d, J 9.7 Hz), 6.83-6.68 (3H, m), 6.66 (1H, d, J 8.6 Hz), 6.20 (1H, d, J 9.8 Hz), 4.11 (2H, q, J 7.1 Hz), 3.80 (2H, br s), 1.14 (3H, t, J 7.1 Hz).

Intermediate 85

Ethyl 7-{4-[bis(methylsulfonyl)amino]phenyl}-3-[(2,4-difluorophenyl)amino]-6-oxo-6,7-dihydrothieno[2,3-b]pyridine-2-carboxylate A mixture of Intermediate 84 (70 mg, 0.16 mmol), methanesulfonylchloride (18 mg, 0.16 mmol) and triethylamine (0.023 mL, 0.16 mmol) in DCM (2 mL) was stirred overnight at r.t. The volatiles were removed in vacuo and the residue dissolved in DCM. The solution was washed with aq NaHCO$_3$, dried (Na$_2$SO$_4$), and concentrated in vacuo. Purification by column chromatography (silica, EtOAc) gave the title compound (50 mg, 53%). δH (CDCl$_3$) 8.50 (1H, s), 7.51 (2H, d, J 6.5 Hz), 7.45 (2H, d, J 6.5 Hz), 7.11 (1H, m), 7.01 (1H, d, J 9.8 Hz), 6.93-6.72 (2H, m), 6.30 (1H, d, J 9.8 Hz), 4.22 (2H, q, J 7.1 Hz), 3.39 (6H, s), 1.25 (3H, t, J 7.1 Hz). LCMS (ES$^+$) RT 3.704 minutes, 598 (M+H)$^+$.

Intermediate 86

Ethyl 3-[(4-fluoro-3-methylphenyl)amino]-6-oxo-7-phenyl-6,7-dihydrothieno[2,3-b]pyridine-2-carboxylate From Intermediate 5 and 4-fluoro-3-methylaniline by the method of Example 1. White solid. δH (DMSO-d6) 8.72 (1H, s), 7.67-7.60 (3H, m), 7.51-7.49 (2H, m), 7.18-7.10 (3H, m), 7.09-6.99 (1H, m), 6.39 (1H, d, J 9.7 Hz), 4.15 (2H, q, J 7.07 Hz), 2.22 (3H, s), 1.72 (3H, t, J 7.08 Hz). LCMS (ES$^+$) 423 (M+H)$^+$.

Intermediate 87

Ammonium 3-[(4-fluoro-3-methylphenyl)amino]-6-oxo-7-phenyl-6,7-dihydrothieno[2,3-b]pyridine-2-carboxylate From Intermediate 86 by the method of Intermediate 31 Beige solid. δH (DMSO-d6) 7.81-7.75 (3H, m), 7.64-7.62 (2H, m), 7.41-7.38 (1H, d, J 9.55 Hz), 7.20-7.15 (1H, t, J 9.01 Hz), 7.04-7.03 (1H, br m), 6.93-6.90 (1H, br m), 6.48-6.46 (1H, d, J 9.54 Hz), 2.35 (3H, s). LCMS (ES$^+$) 395 (M+H)$^+$.

Intermediate 88

Pentafluorophenyl 3-[(4-fluoro-3-methylphenyl) amino]-6-oxo-7-phenyl-6,7-dihydrothieno[2,3-b] pyridine-2-carboxylate EDC (0.163 g, 0.852 mmol) was added to a solution of Intermediate 87 (0.284 g, 0.710 mmol) in DMF (10 mL) and the mixture stirred at r.t. for 30 min. Pentafluorophenol (0.196 g, 1.065 mmol) was added and the mixture stirred at r.t. for 24 hr. The solvent was removed in vacuo and the residue was dissolved in DCM which was then washed with water, dried ($MgSO_4$) and concentrated in vacuo. Purification by column chromatography (silica, 50% Hexane/EtOAc) to produce the title compound as a white solid (0.226 g). δH (DMSO-d6) 8.96 (1H, s), 7.07-6.95 (5H, br m), 7.55-7.39 (4H, br m), 6.29 (1H, d, J 9.86 Hz), 2.08 (3H, s). LCMS ($ES^+$) 561 $(M+H)^+$.

Intermediate 89

2-Acetyl-3-amino-7-phenylthieno[2,3-b]pyridin-6(7H)-one

A mixture of Intermediate 10 (2.5 g, 10 mmol) and chloroacetone (0.88 mL, 11 mmol) in acetonitrile (45 mL) was heated at 50° C. for 2 h. The solvent was removed in vacuo and purification by column chromatography (silica, 2.5% to 3% MeOH in DCM) gave the title compound as a yellow solid (2.32 g, 82%). δH (DMSO-d6) 8.27 (1H, d, J 9.6 Hz), 7.92 (2H, br s), 7.72-7.63 (3H, m), 7.59-7.50 (2H, m), 6.61 (1H, d, J 9.6 Hz), 2.18 (3H, s). LCMS ($ES^+$) RT 2.883 minutes, 284.9 $(M+H)^+$.

Intermediate 90

2-Acetyl-3-bromo-7-phenylthieno[2,3-b]pyridin-6(7H)-one

From Intermediate 89 by the method of Intermediate 14. Light brown solid. δH (DMSO-d6) 7.98 (1H, d, J 9.7 Hz), 7.74-7.65 (3H, m), 7.59-7.56 (2H, m), 6.77 (1H, d, J 9.7 Hz), 2.68 (3H, s). LCMS ($ES^+$) RT 3.388 minutes, 349.8 $(M+H)^+$.

Intermediate 91

3-Amino-6-oxo-7-pyridin-3-yl-6,7-dihydrothieno[2,3-b]pyridine-2-carbonitrile

Acetonitrile (5 mL) was added to a solution of sodium bis(trimethylsilyl)amide (16.1 mL of 1M solution in THF, 16.1 mmol) in THF (50 mL) at −78° C. Pyridylisothiocyanate (0.820 mL, 7.34 mmol) was added and the mixture allowed to warm to r.t. over 2 h. EtOH (30 mL) and N,N-dimethyluracil (1.03 g, 7.34 mmol) were added and the mixture heated at reflux for 18 h. Volatiles were removed in vacuo. The residue was dissolved in acetonitrile (20 mL), chloroacetonitrile (0.470 mL, 7.34 mmol) was added and the mixture heated at 50° C. for 3 h. The bulk of the solvent was removed in vacuo, water (50 mL) was added and the mixture cooled to 0° C. The precipitate was filtered off, washed with water and ether and dried to give the title compound as a brown solid (1.47 g, 75%). δH (DMSO-d6) 8.80-8.64 (2H, m), 8.13-7.95 (2H, m), 7.60-7.56 (1H, m), 7.09 (2H, s), 6.48 (1H, d, J 9.5 Hz). LCMS ($ES^+$) RT 2.493 minutes, 268.9 $(M+H)^+$.

Intermediate 92

3-Bromo-6-oxo-7-pyridin-3-yl-6,7-dihydrothieno[2,3-b]pyridine-2-carbonitrile

From Intermediate 91 by the method of Intermediate 14. LCMS ($ES^+$) RT 2.954 minutes, 331.8 $(M+H)^+$.

Intermediate 93

Benzyl 3-[({3-[(2,4-difluorophenyl)amino]-6-oxo-7-phenyl-6,7-dihydrothieno[2,3-b]pyridin-2-yl}carbonyl)amino]pyrrolidine-1-carboxylate To a solution of Intermediate 79 (250 mg, 0.44 mmol) in DCM (5 mL) was added benzyl 3-amino-pyrrolidine-1-carboxylate (350 mg, 1.6 mmol) and the reaction stirred at room temperature for 18 h. An additional equivalent of the aminopyrrolidine (96 mg, 0.44 mmol) was added and the reaction stirred for a further 18 h. Solvent was then removed in vacuo and the crude residue subject to column chromatography (silica, 60% EtOAc in isohexane) to give the title compound as a yellow oil (141 mg, 53%). LCMS ($ES^+$) RT 3.63 minutes, 601 $(M+H)^+$.

EXAMPLE 1

Ethyl 3-(phenylamino)-6-oxo-7-phenyl-6,7-dihydrothieno[2,3-b]pyridine-2-carboxylate Tris(dibenzylideneacetone)dipalladium(0) (12 mg, 0.0133 mmol, 5 mol %) was added to a mixture of Intermediate 5 (100 mg, 0.265 mmol), caesium carbonate (120 mg, 0.37 mmol), aniline (0.030 mL, 0.32 mmol) and BINAP (17 mg, 0.027 mmol, 10 mol %) in anhydrous toluene (2 mL) and the reaction heated to reflux under nitrogen for 18 h. Solvent was removed in vacuo and the crude residue purified by chromatography on silica (0-20% EtOAc in DCM) to give the title compound as a white solid (80 mg). δH ($CDCl_3$) 8.70 (1H, bs), 7.57-7.47 (3H, m), 7.33-7.25 (4H, m), 7.20-7.10 (4H, m), 6.27 (1H, d, J 9.7 Hz), 4.19 (2H, q, J 7.1 Hz), 1.22 (3H, t, J 7.1 Hz). LCMS ($ES^*$) RT 4.10 minutes, 391 $(M+H)^+$.

General procedure for the preparation of Ethyl 3-anilino-6-oxo-7-phenyl-6,7-dihydrothieno[2,3-b]pyridine-2-carboxylates The compounds of Examples 2-13 were prepared by parallel synthesis using a Radleys Carousel reaction station (Radleys Ltd., Saffron Walden, U.K.) following a procedure similar to that described for Example 1. Therefore to each oven dried reaction tube in the Carousel was added a magnetic stirrer, the appropriate substituted aniline (0.64 mmol), anhydrous toluene (3 mL), Intermediate 5 (200 mg, 0.53 mmol), caesium carbonate (240 mg, 0.74 mmol) and tris (dibenzylideneacetone)dipalladium(0) (48 mg, 0.053 mmol, 10 mol %) and BINAP (66 mg, 0.106 mmol, 20 mol %). The reactions were heated to reflux under nitrogen and with magnetic stirring for 48 h. Each reaction was then diluted with DCM (10 mL), washed with water (10 mL), dried ($MgSO_4$) and concentrated in vacuo. The crude products were purified on silica eluting with 0-20% EtOAc in DCM to give the title compounds as solids.

EXAMPLE 2

Ethyl 3-[(2-chlorophenyl)amino]-6-oxo-7-phenyl-6,7-dihydrothieno[2,3-b]pyridine-2-carboxylate From 2-chloroaniline to give the title compound (92 mg). δH (CDCl$_3$) 8.60 (1H, bs), 7.56-7.48 (3H, m), 7.40-7.38 (1H, m), 7.36-7.32 (2H, m), 7.20-7.15 (2H, m), 7.14-7.05 (1H, m), 7.05-6.98 (1H, m), 6.35 (1H, d, J 9.8 Hz), 4.21 (2H q, J 7.1 Hz), 1.23 (3H, t, J 7.1 Hz). LCMS (ES$^+$) RT 4.38 minutes, 425 (M+H)$^+$.

EXAMPLE 3

Ethyl 3-[(3-chlorophenyl)amino]-6-oxo-7-phenyl-6,7-dihydrothieno[2,3-b]pyridine-2-carboxylate From 3-chloroaniline to give the title compound (65 mg). δH (CDCl$_3$) 8.60 (1H, bs), 7.57-7.50 (3H, m), 7.36-7.30 (2H, m), 7.20-7.18 (1H, m), 7.18 (1H, d, J 9.7 Hz), 7.05 (1H, d, J 1.5 Hz), 7.05-7.04 (1H, m), 6.96-6.92 (1H, m), 6.35 (1H, d, J 9.8 Hz), 4.19 (2H, q, J 7.1 Hz), 1.22 (3H, t, J 7.1 Hz). LCMS (ES$^+$) RT 4.30 minutes, 425 (M+H)$^+$.

EXAMPLE 4

Ethyl 3-[(4-chlorophenyl)amino]-6-oxo-7-phenyl-6,7-dihydrothieno[2,3-b]pyridine-2-carboxylate From 4-chloroaniline to give the title compound (115 mg). δH (CDCl$_3$) 8.63 (1H, bs), 7.56-7.50 (3H, m), 7.34-7.31 (2H, m), 7.28-7.24 (2H, m), 7.12 (1H, d, J 9.8 Hz), 7.02-6.99 (2H, m), 6.32 (1H, d, J 9.8 Hz), 4.19 (2H, q, J 7.2 Hz), 1.22 (3H, t, J 7.2 Hz). LCMS (ES$^+$) RT 4.32 minutes, 425 (M+H)$^+$.

EXAMPLE 5

Ethyl 3-[methyl(phenyl)amino]-6-oxo-7-phenyl-6,7-dihydrothieno[2,3-b]pyridine-2-carboxylate From N-methylaniline to give the title compound (53 mg). δH (CDCl$_3$) 7.61-7.43 (3H, m), 7.40-7.32 (2H, m), 7.26 (1H, d, J 9.6 Hz), 7.22-7.10 (2H, m), 6.77 (1H, t, J 7.3 Hz), 6.67 (2H, dd, J 8.7, 1.0 Hz), 6.43 (1H, d, J 9.6 Hz), 4.10 (2H, q, J 7.1 Hz), 3.33 (3H, s), 1.11 (3H, t, J 7.1 Hz). LCMS (ES$^+$) RT 4.01 minutes, 405 (M+H)$^+$.

EXAMPLE 6

Ethyl 3-[(2-methoxyphenyl)amino]-6-oxo-7-phenyl-6,7-dihydrothieno[2,3-b]pyridine-2-carboxylate From 2-methoxyaniline to give the title compound (133 mg). δH (CDCl$_3$) 8.53 (1H, bs), 7.58-7.41 (3H, m), 7.36-7.29 (2H, m), 7.26 (1H, d, J 9.7 Hz), 7.07-6.96 (2H, m), 6.89-6.75 (2H, m), 6.30 (1H, d, J 9.7 Hz), 4.18 (2H, q, J 7.2 Hz), 3.84 (3H, s), 1.22 (3H, t, J 7.2 Hz). LCMS (ES$^+$) RT 4.06 minutes, 421 (M+H).

EXAMPLE 7

Ethyl 6-oxo-7-phenyl-3-[(3-trifluoromethoxyphenyl)amino]-6,7-dihydrothieno[2,3-b]pyridine-2-carboxylate From 3-trifluoromethoxyaniline to give the title compound (60 mg). δH (CDCl$_3$) 8.66 (1H, bs), 7.58-7.41 (3H, m), 7.34 (2H, d, J 8.0 Hz), 7.28 (1H, t, J 8.3 Hz), 7.20 (1H, d, J 9.8 Hz), 6.98-6.93 (1H, m), 6.92-6.83 (2H, m), 6.35 (1H, d, J 9.8 Hz), 4.19 (2H, q, J 7.1 Hz), 1.22 (3H, t, J 7.1 Hz). LCMS (ES$^+$) RT 4.39 minutes, 475 (M+H)$^+$.

EXAMPLE 8

Ethyl 3-[(4-cyanophenyl)amino]-6-oxo-7-phenyl-6,7-dihydrothieno[2,3-b]pyridine-2-carboxylate From 4-cyanoaniline to give the title compound (110 mg). δH (CDCl$_3$) 8.59 (1H, bs), 7.61-7.45 (5H, m), 7.36-7.31 (2H, m), 7.28 (1H, d, J 9.7 Hz), 7.02 (2H, d, J 8.6 Hz), 6.43 (1H, d, J 9.7 Hz), 4.20 (2H, q, J 7.1 Hz), 1.23 (3H, t, J 7.1 Hz). LCMS (ES$^+$) RT 3.71 minutes, 416 (M+H)$^+$.

EXAMPLE 9

Ethyl 3-[(3-cyanophenyl)amino]-6-oxo-7-phenyl-6,7-dihydrothieno[2,3-b]pyridine-2-carboxylate From 3-cyanoaniline to give the title compound (100 mg). δH (CDCl$_3$) 8.58 (1H, bs), 7.61-7.43 (3H, m), 7.40-7.20 (6H, m), 7.14 (1H, d, J 9.8 Hz), 6.38 (1H, d, J 9.8 Hz), 4.19 (2H, q, J 7.1 Hz), 1.23 (3H, t, J 7.1 Hz). LCMS (ES$^+$) RT 3.78 minutes, 416 (M+H)$^+$.

EXAMPLE 10

Ethyl 3-[(2-cyanophenyl)amino]-6-oxo-7-phenyl-6,7-dihydrothieno[2,3-b]pyridine-2-carboxylate From 2-cyanoaniline to give the title compound (133 mg). δH (CDCl$_3$) 8.72 (1H, bs), 7.61-7.47 (4H, m), 7.43-7.40 (1H, m), 7.36-7.31 (2H, m), 7.22-7.15 (1H, m), 7.11-7.00 (2H, m), 6.40 (1H, d, J 9.8 Hz), 4.22 (2H, q, J 7.1 Hz), 1.24 (3H, t, J 7.1 Hz). LCMS (ES$^+$) RT 3.80 minutes, 416 (M+H)$^+$.

EXAMPLE 11

Ethyl 3-[(3-fluoro-4-methoxyphenyl)amino]-6-oxo-7-phenyl-6,7-dihydrothieno[2,3-b]pyridine-2-carboxylate From 3-fluoro-4-methoxyaniline to give the title compound (122 mg). δH (CDCl$_3$) 8.63 (1H, bs), 7.58-7.40 (3H, m), 7.32-7.25 (2H, m), 6.99 (1H, d, J 9.8 Hz), 6.93-6.78 (3H, m), 6.28 (1H, d, J 9.8 Hz), 4.18 (2H, q, J 7.1 Hz), 3.85 (3H, s), 1.22 (3H, t, J 7.1 Hz). LCMS (ES$^+$) RT 3.99 minutes, 439 (M+H)$^+$.

EXAMPLE 12

Ethyl 3-[(2,4-difluorophenyl)amino]-6-oxo-7-phenyl-6,7-dihydrothieno[2,3-b]pyridine-2-carboxylate From 2,4-difluoroaniline to give the title compound (99 mg). δH (CDCl$_3$) 8.49 (1H, bs), 7.58-7.40 (3H, m), 7.32-7.25 (2H, m), 7.13-7.04 (1H, m), 7.01 (1H, d, J 9.8 Hz), 6.93-6.86 (1H, m), 6.82-6.75 (1H, m), 6.31 (1H, d, J, 9.8 Hz), 4.20 (2H, q, J 7.1 Hz), 1.23 (3H, J 7.1 Hz). LCMS (ES$^+$) RT 4.06 minutes, 427 (M+H)$^+$.

EXAMPLE 13

Ethyl 6-oxo-7-phenyl-3-[(3-tolyl)amino]-6,7-dihydrothieno[2,3-b]pyridine-2-carboxylate From 3-toluidine to give the title compound (95 mg). δH (CDCl$_3$) 8.66 (1H, bs), 7.59-7.41 (3H, m), 7.36-7.27 (2H, m), 7.22-7.13 (1H, m), 7.11 (1H, d, J 9.8 Hz), 6.95-6.84 (3H, m), 6.27 (1H, d, J 9.8 Hz), 4.18 (2H, q, J 7.1 Hz), 2.28 (3H, s), 1.22 (3H, t, J 7.1 Hz). LCMS (ES$^+$) RT 4.36 minutes, 405 (M+H)$^+$.

EXAMPLE 14

Ammonium 6-oxo-3-(phenylamino)-7-phenyl-6,7-dihydrothieno[2,3-b]pyridine-2-carboxylate Lithium hydroxide monohydrate (302 mg, 7.2 mmol) was added to a suspension of the compound of Example 1 (1.49 g, 3.6 mmol) in THF (20 mL) and water (20 mL) and the mixture heated at 60° C. for 18 h. The reaction was cooled to r.t. and bulk of THF removed in vacuo. The remaining concentrate was diluted with saturated ammonium chloride(aq) (50 mL) and the solid precipitate filtered and washed with water (2×20 mL), Et$_2$O (2×20 mL) and dried in vacuo to give the title compound as a white solid in quantitative yield. LCMS (ES$^+$) RT 3.24 minutes, 363 (M+H)$^+$.

EXAMPLE 15

3-(Phenylamino)-7-phenylthieno[2,3-b]pyridin-6(7H)-one

To a solution of the compound of Example 14 (200 mg) in 1,4-dioxan (10 mL) was added 2M HCl(aq) (0.5 mL) and the reaction mixture heated at 70° C. for 1 h. The reaction was diluted with water (30 mL), extracted with EtOAc (3×20 mL) and the EtOAc extracts dried (MgSO$_4$) and concentrated in vacuo. The crude residue was purified by chromatography on silica (0-5% EtOAc in DCM) to give the title compound as a white solid (90 mg). δH (DMSO-d6) 8.21 (1H, bs), 7.96 (1H, d, J 9.6 Hz), 7.63-7.47 (3H, m), 7.43-7.36 (2H, m), 7.25-7.11 (2H, m), 7.10-7.03 (2H, m), 6.82-6.71 (1H, m), 6.46 (1H, d, J 9.6 Hz), 6.44 (1H, s). LCMS (ES$^+$) RT 3.54 minutes, 319 (M+H)$^+$.

EXAMPLE 16

6-Oxo-3-(Phenylamino)-7-phenyl-6,7-dihydrothieno[2,3-b]pyridine-2-carboxamide

To a suspension of the compound of Example 14 (370 mg, 1.02 mmol) in anhydrous DMF (5 mL) was added 1,1'-carbonyldiimidazole (182 mg, 1.12 mmol) and the reaction stirred at r.t. under nitrogen for 20 mins. Ammonium hydroxide (2 mL of 28% NH$_3$ in water) was added and the reaction stirred for 72 h. Solvents were removed in vacuo and the crude residue purified by chromatography on silica (0-15% THF in DCM) to give the title compound as a white solid (123 mg). δH (DMSO-d6) 8.74 (1H, s), 7.67-7.34 (3H, m), 7.33-7.27 (2H, m), 7.22-7.00 (5H, m), 6.82-6.71 (3H, m), 6.21 (1H, d, J 9.7 Hz). LCMS (ES$^+$) RT 3.04 minutes, 362 (M+H)$^+$.

EXAMPLE 16

Alternative Route

6-Oxo-7-phenyl-3-phenylamino-6,7-dihydro-thieno[2,3-b]pyridine-2-carboxamide

To a 100 mL round bottomed flask, fitted with nitrogen inlet/outlet was added Example 18 (1.45 g) and 13.3 mL of a solution of 0.382 g of sodium hydroxide in water (20 mL), plus 30 mL of absolute ethanol. The reaction was then set to reflux. After approximately 1 hour at reflux the reaction had gone to completion. The reaction mixture was cooled to ambient, and poured onto 100 mL of 1M HCl. This mixture was then extracted with 2×75 mL of dichloromethane. The combined organics were washed with 1M HCl (2×50 mL), dried (MgSO$_4$) and evaporated to dryness. The resulting crude product was then passed down a silica column eluting with 4:1 DCM:EtOAc. The product was then dried under vacuum at 50° C., to give the title compound as a light yellow solid (1.47 g). δH (DMSO-d6) 8.85 (1H, s), 7.60-7.40 (5H, m), 7.30-7.10 (5H, m), 6.80 (3H, m), 6.30 (1H, d, J 8.5 Hz). LCMS (Conditions B) (ES$^+$) RT 2.92 minutes, 362 (M+H)$^+$.

EXAMPLE 17

6-Oxo-N-(2-piperidinoethyl)-3-(phenylamino)-7-phenyl-6,7-dihydrothieno[2,3-b]pyridine-2-carboxamide To a suspension of the compound of Example 14 (90 mg, 0.23 mmol) in DCM (2 mL) was added EDC (60 mg, 0.30 mmol) and HOBT (41 mg, 0.30 mmol) and the mixture stirred at r.t. for 15 minutes. A solution 1-(2-aminoethyl)piperidine (45 mg, 0.35 mmol) in DCM (0.5 mL) was added and the reaction stirred at r.t. for 18 h. The reaction mixture was diluted with DCM (10 mL), washed with water (2×5 mL), dried (MgSO$_4$) and concentrated in vacuo. The crude product was purified by chromatography on silica (0-20% THF in DCM) to give the title compound as an off-white solid (23 mg). δH (CDCl$_3$) 8.61 (1H, s), 7.61-7.43 (3H, m), 7.40-7.27 (2H, m), 7.25-7.13 (3H, m), 7.00-6.89 (3H, m), 6.50 (1H, bs), 6.33 (1H, d, J 9.7 Hz), 3.43-3.25 (2H, m), 2.47-2.32 (2H, m), 2.31-2.11 (4H, m), 1.50-1.40 (4H, m), 1.39-1.25 (2H, m). LCMS (ES$^+$) RT 2.40 minutes, 473 (M+H)$^+$.

EXAMPLE 18

6-Oxo-3-(Phenylamino)-7-phenyl-6,7-dihydrothieno[2,3-b]pyridine-2-carbonitrile

Tris(dibenzylideneacetone)dipalladium(0) (34 mg, 0.0375 mmol, 5 mol %) was added to a mixture of Intermediate 9 (250 mg, 0.75 mmol), caesium carbonate (342 mg, 1.05 mmol), aniline (0.082 mL, 0.9 mmol) and BINAP (47 mg, 0.075 mmol, 10 mol %) in anhydrous toluene (7 mL) and the reaction heated to reflux under nitrogen for 24 h. The reaction mixture was partitioned between DCM (60 mL) and water (25 mL) and the DCM extracts dried (Na$_2$SO$_4$) and concentrated in vacuo. The crude residue was purified by chromatography on silica (10-15% EtOAc in DCM) to give the title compound as an off-white solid (185 mg). δH (CDCl$_3$) 7.79-7.71 (3H, m), 7.56-7.41 (5H, m), 7.33-7.29 (1H, m), 7.24 (2H, dd, J 7.5, 1.0 Hz), 6.65 (1H, d, J 9.8 Hz), 6.59 (1H, bs). LCMS (ES$^+$) 344 (M+H)$^+$.

EXAMPLE 18

Alternative Route

6-Oxo-7-phenyl-3-Phenylamino-6,7-dihydro-thieno[2,3-b]pyridine-2-carbonitrile

To a dry 50 ml 2 necked round bottomed flask, fitted with nitrogen inlet/outlet was added $Cs_2CO_3$ (1.38 g), (+/−)-BINAP (188 mg), intermediate 9 (1.00 g) and tris(dibenzylideneacetone)dipalladium(0) (138.4 mg). To this mixture was added 20 ml of anhydrous toluene, which had been thoroughly degassed. The reaction mixture was then put through a vacuum and nitrogen cycle. To the reaction mixture was added aniline (0.338g) via syringe. The reaction was then set to reflux. After 16 hours at reflux the reaction had gone to completion. The reaction mixture was cooled to ambient, held at this temperature for 1 hour. The solid was then collected by filtration. This crude solid was then slurried in 10 mL of 1.0M HCl for 1 hour. The beige coloured solid was collected by filtration, washing with 10 mL of water. The product was then dried under vacuum at 50° C., to give the title compound as a light brown solid (0.68 g). δH (DMSO-d6) 9.60 (1H, s), 8.25 (1H, d, J 8.5 Hz), 7.75-7.90 (5H, m), 7.50 (2H, m), 7.40 (2H, m), 7.30 (1H, t, J 7.5 Hz), 6.85 (1H, d, J 8.5 Hz). LCMS (Conditions B) (ES+) RT 3.58 minutes, 344 (M+H)+

EXAMPLE 19

3-(3-Bromophenylamino)-6-oxo-7-phenyl-6,7-dihydrothieno[2,3-b]pyridine-2-carbonitrile The title compound was prepared from 3-bromoaniline (155 mg, 0.9 mmol) following the method described for the compound of Example 18 to give the product as a pale yellow solid (183 mg). δH (CDCl3) 7.91-7.83 (3H, m), 7.83-7.66 (2H, m), 7.62 (1H, d, J 9.7 Hz), 7.52-7.44 (3H, m), 7.23 (1H, dt, J 7.1, 1.7 Hz), 6.81 (1H, d, J 9.7 Hz), 6.74 (1H, bs). LCMS (ES+) 422 (M+H)+ 79Br, 424 (M+H)+ 81Br.

EXAMPLE 20

3-(3-chlorophenylamino)-6-oxo-7-phenyl-6,7-dihydrothieno[2,3-b]pyridine-2-carbonitrile The title compound was prepared from 3-chloroaniline (115 mg, 0.9 mmol) following the method described for the compound of Example 18 to give the product as a pale yellow solid (125 mg). δH (CDCl3) 7.67-7.58 (3H, m), 7.44-7.41 (2H, m), 7.39 (1H, d, J 9.7 Hz), 7.31-7.26 (1H, m), 7.12-7.09 (1H, m), 7.04 (1H, t, J 2.0 Hz), 6.95-6.92 (1H, m), 6.57 (1H, d, J 9.7 Hz), 6.54 (1H, bs). LCMS (ES+) 378 (M+H)+ 35Cl, 380 (M+H)+ 37Cl.

EXAMPLE 21

7-(2-Chlorophenyl)-3-[(4-fluoro-3-methylphenyl)amino]-6-oxo-6,7-dihydrothieno[2,3-b]pyridine-2-carbonitrile A mixture of Intermediate 14 (500 mg, 1.37 mmol), 4-fluoro-3-methyl aniline (206 mg, 1.64 mmol), caesium carbonate (625 mg, 1.92 mmol), BINAP (85 mg, 0.37 mmol, 10 mol %) and tris(dibenzylideneacetone)dipalladium(0) (63 mg, 0.0685 mmol, 5 mol %) in toluene was heated at reflux for 18 h. A second charge of BINAP (42 mg, 5 mol %) and tris(dibenzylideneacetone)-dipalladium(0) (31.5 mg, 2.5 mol %) was added and the mixture heated at reflux for a further 4 days. The mixture was partitioned between DCM (100 mL) and water (50 mL). The organic layer was dried ($Na_2SO_4$) and concentrated in vacuo. Purification by column chromatography (silica, 10% EtOAc in DCM) gave the title compound as an off-white solid (160 mg, 28%). δH (DMSO-d6) 9.39 (1H, s), 8.17 (1H, d, J 9.7 Hz), 7.87 (1H, dd, J 1.7, 7.9 Hz), 7.79 (1H, dd, J 2.1, 7.Hz), 7.75-7.66 (2H, m), 7.24-7.12 (3H, m), 6.71 (1H, d, J 9.7 Hz), 2.29 (3H, d, J 1.7 Hz). LCMS (ES+) RT 3.63 minutes, 410 (M+H)+

EXAMPLE 22

7-(2-Chlorophenyl)-3-[(4-fluoro-3-methylphenyl)amino]-6-oxo-6,7-dihydrothieno[2,3-b]pyridine-2-carboxamide Sodium hydroxide (0.68 mL of a 0.25M aq. solution, 0.17 mmol) was added to Example 21 (136 mg, 0.33 mmol) in ethanol (6 mL) and the mixture heated at reflux for 1 h. The mixture was concentrated in vacuo, the residue suspended in water and the solid filtered off and dried. Purification by column chromatography (silica, 20% EtOAc in DCM) gave the title compound as a pale yellow solid (65 mg, 46%). δH (CDCl3) 9.08 (1H, br s), 7.60-7.57 (1H, m), 7.48-7.41 (2H, m), 7.38-7.35 (1H, m), 7.06 (1H, d, J 9.8 Hz), 6.93-6.85 (3H, m), 6.29 (1H, d, J 9.8 Hz), 5.18 (2H, br s), 2.20 (3H, d, J 1.4 Hz). LCMS (ES+) RT 3.28 minutes, 428 (M+H)+

EXAMPLE 23

3-Anilino-7-(2-chlorophenyl)-6-oxo-6,7-dihydrothieno[2,3-b]pyridine-2-carbonitrile Prepared from Intermediate 14 and aniline by the method of Example 21. Pale yellow solid (100 mg, 32%). δH (DMSO-d6) 9.45 (1H, br s), 8.12 (1H, d, J 9.7 Hz), 7.90-7.87 (1H, m), 7.80-7.78 (1H, m), 7.74-7.69 (2H, m), 7.44-7.39 (2H, m), 7.27-7.24 (2H, m), 7.17-7.13 (1H, m), 6.71 (1H, d, J 9.7 Hz). LCMS (ES+) RT 3.95 minutes, 378.0 (M+H)+.

EXAMPLE 24

3-Anilino-7-(2-chlorophenyl)-6-oxo-6,7-dihydrothieno[2,3-b]pyridine-2-carboxamide Sodium hydroxide (1.44 mL of a 0.25M aq. solution, 0.24 mmol) was added to Example 23 (90 mg, 0.24 mmol) in ethanol (10 mL) and the mixture heated at reflux for 1 h. The mixture was concentrated in vacuo, the residue suspended in water and the solid filtered off and dried to give the title compound as an off-white solid (66 mg, 70%). δH (DMSO-d6) 9.04 (1H, br s), 7.89-7.86 (1H, m), 7.81-7.79 (1H, m), 7.74-7.67 (2H, m), 7.43 (2H, br s), 7.42-7.40 (1H, m), 7.36-7.32 (2H, m), 7.04-6.99 (3H, m), 6.50 (1H, d, J 9.7 Hz). LCMS (ES+) RT 3.07 minutes, 396.0 (M+H)+

EXAMPLE 25

3-[(4-Fluoro-3-methylphenyl)amino]-7-(4-methylphenyl)-6-oxo-6,7-dihydrothieno[2,3-b]pyridine-2-carboxamide Sodium hydroxide (2.0 mL of a 0.25M aq. solution, 0.5 mmol) was added to Intermediate 18 (350 mg, 0.65 mmol) in ethanol (20 mL) and the mixture heated at reflux for 1 h. The mixture was concentrated in vacuo, the residue suspended in water (2×15 mL) and the solid filtered off and dried. Purification by column chromatography (silica, 20% EtOAc in DCM) gave a pale brown solid which was triturated with $Et_2O$/hexane (1:2, 20 mL). The solid was filtered off to give the title compound as a pale brown solid (80 mg, 30%). δH (DMSO-d6) 9.00 (1H, br s), 7.43-7.36 (4H, m), 7.29 (2H, br s), 7.24 (1H, d, J 9.7 Hz), 7.06-7.01 (1H, m), 6.92-6.89 (1H, m), 6.79-6.77 (1H, m), 6.37 (1H, d, J 9.7 Hz), 2.41 (3H, s), 2.18 (3H, d, $J_{H-F}$ 1.2 Hz). LCMS (ES$^+$) RT 3.33 minutes, 408.0 (M+H)$^+$

EXAMPLE 26

7-(4-Methylphenyl)-3-[(3-methylphenyl)amino]-6-oxo-6,7-dihydrothieno[2,3-b]pyridine-2-carbonitrile A mixture of Intermediate 17 (225 mg, 0.65 mmol), 3-methylaniline (0.165 mL, 0.78 mmol), caesium carbonate (297 mg, 0.91 mmol), BINAP (41 mg, 0.065 mmol) and tris(dibenzylideneacetone)dipalladium(0) (30 mg, 0.0325 mmol) in toluene (5 mL) was heated at 100° C. under N$_2$ for 18 h. The mixture was partitioned between DCM (100 mL) and water (50 mL). The organic phase was dried (Na$_2$SO$_4$) and concentrated in vacuo. Purification by column chromatography (silica, 5 to 10% EtOAc in DCM) gave the title compound as a pale brown solid (63 mg, 26%). δH (DMSO-d6) 9.04 (1H, br s), 7.77 (1H, d, J 9.7 Hz), 7.23-7.16 (4H, m), 7.02-6.98 (1H, m), 6.77-6.74 (2H, m), 6.68-6.66 (1H, m), 6.37 (1H, d, J 9.7 Hz), 2.21 (3H, s), 2.08 (3H, s). LCMS (ES$^+$) RT 3.72 minutes, 372.0 (M+H)$^+$

EXAMPLE 27

7-(4-Methylphenyl)-3-[(3-methylphenyl)amino]-6-oxo-6,7-dihydrothieno[2,3-b]pyridine-2-carboxamide Sodium hydroxide (0.30 mL of a 0.25M aq. solution, 0.075 mmol) was added to Example 26 (56 mg, 0.15 mmol) in ethanol (4 mL) and the mixture heated at reflux for 1 h. The mixture was concentrated in vacuo, the residue suspended in water, acidified with 1M HCl aq, and the solid filtered off and dried to give the title compound (40 mg, 68%). δH (DMSO-d6) 8.93 (1H, br s), 7.44-7.37 (4H, m), 7.30 (2H, brs), 7.29 (1H, d, J 9.6 Hz), 7.14 (1H, t, J 7.6 Hz), 6.78-6.71 (3H, m), 6.39 (1H, d, J 9.6 Hz), 2.42 (3H, s), 2.25 (3H, s). LCMS (ES$^+$) RT 3.29 minutes, 390.0 (M+H)$^+$

EXAMPLE 28

7-Cyclopropyl-3-[(4-fluoro-3-methylphenyl)amino]-6-oxo-6,7-dihydrothieno[2,3-b]pyridine-2-carbonitrile Prepared from Intermediate 21 and 4-fluoro-3-methylaniline by the method of Example 21. Light yellow solid. δH (CDCl$_3$) 7.19 (1H, d, J 9.7 Hz), 6.97-6.84 (3H, m), 6.51 (1H, br s), 6.35 (1H, d, J 9.7 Hz), 3.08-3.02 (1H, m), 2.25 (3H, s), 1.32-1.23 (2H, m), 1.14-1.07 (2H, m). LCMS (ES$^+$) RT 3.385 minutes, 339.9 (M+H)$^+$

EXAMPLE 29

7-Cyclopropyl-3-[(4-fluoro-3-methylphenyl)amino]-6-oxo-6,7-dihydrothieno[2,3-b]pyridine-2-carboxamide Prepared from Example 28 by the method of Example 22. Light yellow solid. δH (CDCl$_3$) 9.0-8.8 (1H, br s), 7.01 (1H, d, J 9.7 Hz), 6.98-6.84 (3H, m), 6.23 (1H, d, J 9.7 Hz), 5.51 (2H, br s), 3.07-3.03 (1H, m), 2.22 (3H, s), 1.30-1.23 (2H, m), 1.15-1.12 (2H, m). LCMS (ES$^+$) RT 3.009 minutes, 358.0 (M+H)$^+$

EXAMPLE 30

7-Cyclopropyl-3-[(3-methylphenyl)amino]-6-oxo-6,7-dihydrothieno[2,3-b]pyridine-2-carbonitrile Prepared from Intermediate 21 and m-toluidine by the method of Example 21. Light yellow solid. δH (CDCl$_3$) 7.25 (1H, d, J 9.6 Hz), 7.20-7.16 (1H, m), 6.04 (1H, d, J 7.6 Hz), 7.82-7.80 (2H, m), 6.67 (1H, s), 6.33 (1H, d, J 9.6 Hz), 3.07-3.02 (1H, m), 2.31 (3H, s), 1.32-1.17 (2H, m), 1.14-1.07 (2H, m). LCMS (ES$^+$) RT 3.336 minutes, 321.9 (M+H)$^+$

EXAMPLE 31

7-Cyclopropyl-3-[(3-methylphenyl)amino]-6-oxo-6,7-dihydrothieno[2,3-b]pyridine-2-carboxamide Prepared from Intermediate 30 by the method of Example 22. Light yellow solid. δH (CDCl$_3$) 8.65 (1H, brs), 7.25-7.11 (2H, m), 6.88 (1H, d, J 7.5 Hz), 6.83-6.80 (2H, m), 6.24 (1H, d, J 9.7 Hz), 5.68 (2H, br s), 3.08-3.05 (1H, m), 2.3 (3H, s), 1.34-1.23 (2H, m), 1.15-1.13 (2H, m). LCMS (ES$^+$) RT 2.888 minutes, 340.0 (M+H)$^+$

EXAMPLE 32

3-[(4-fluoro-3-methylphenyl)amino]-7-(2-methylphenyl)-6-oxo-6,7-dihydrothieno[2,3-b]pyridine-2-carbonitrile Prepared from Intermediate 24 and 4-fluoro-3-methyl aniline by the method of Example 21. δH (CDCl$_3$) 7.52-7.38 (4H, m), 7.28-7.26 (1H, m), 7.03-6.90 (3H, m), 6.50 (1H, d, J 9.7 Hz), 6.27 (1H, s), 2.29 (3H, s), 2.14 (3H, s). LCMS (ES$^+$) RT 3.641 minutes, 389.9 (M+H)$^+$

EXAMPLE 33

3-[(2,4-Difluorophenyl)amino]-7-(2-methylphenyl)-6-oxo-6,7-dihydrothieno[2,3-b]pyridine-2-carbonitrile Prepared from Intermediate 24 and 2,4-difluoroaniline by the method of Example 21. δH (CDCl$_3$) 7.5-7.34 (4H, m), 7.26-7.24 (1H, m), 7.2-7.14 (1H, m), 7.0-6.88 (2H, m), 6.57 (1H, d, J 9.7 Hz), 6.36 (1H, br s), 2.14 (3H, s). LCMS (ES$^+$) RT 3.464 minutes, 394.0 (M+H)$^+$

EXAMPLE 34

7-(2-Methylphenyl)-3-[(3-methylphenyl)amino]-6-oxo-6,7-dihydrothieno[2,3-b]pyridine-2-carboxamide Prepared from Intermediate 25 by the method of Example 22. δH (CDCl$_3$) 7.48-7.36 (3H, m), 7.28-7.18 (3H, m), 6.95-6.89 (3H, m), 6.36 (1H, d, J 9.8 Hz), 5.48 (2H, br s), 2.34 (3H, s), 2.13 (3H, s). LCMS (ES$^+$) RT 3.24 minutes, 390.0 (M+H)$^+$

EXAMPLE 35

3-[(4-Fluoro-3-methylphenyl)amino]-7-(2-methylphenyl)-6-oxo-6,7-dihydrothieno[2,3-b]pyridine-2-carboxamide Prepared from Example 32 by the method of Example 22. δH (CDCl$_3$) 7.48-7.37 (3H, m), 7.27-7.26 (1H, m), 7.13 (1H,

EXAMPLE 36

3-[(2,4-Difluorophenyl)amino]-7-(2-methylphenyl)-6-oxo-6,7-dihydrothieno[2,3-b]pyridine-2-carboxamide Prepared from Example 33 by the method of Example 22. δH (DMSO-d6) 9.27 (1H, s), 7.59-7.40 (7H, m), 7.35-7.31 (1H, m), 7.19-7.06 (2H, m), 6.48 (1H, d, J 9.7 Hz), 2.55 (3H, s). LCMS (ES$^+$) RT 3.18 minutes, 412.0 (M+H)$^+$

EXAMPLE 37

Ethyl 3-anilino-7-(1H-indol-5-yl)-6-oxo-6,7-dihydrothieno[2,3-b]pyridine-2-carboxylate From Intermediate 26 and aniline by the method of Example 1. Pale yellow solid. δH (CDCl$_3$) 8.70 (1H, br s), 8.56 (1H, br s), 7.56 (1H, br s), 7.41-7.26 (3H, m), 7.21-7.09 (5H, m), 7.01 (1H, dd, J 8.5, 2.0 Hz), 6.53 (1H, br s), 6.32 (1H, d, J 9.7 Hz), 4.15 (2H, q, J 7.1 Hz), 1.18 (3H, t, J 7.1 Hz). LCMS (ES$^+$) RT 3.77 minutes, 430 (M+H)$^+$.

EXAMPLE 38

3-Anilino-7-(1H-indol-5-yl)-6-oxo-6,7-dihydrothieno[2,3-b]pyridine-2-carboxamide A mixture of Example 37 (200 mg) and liquid ammonia (5 mL) in ethoxyethanol (10 mL) was heated in a sealed vessel at 80° C. at 400 p.s.i. for 48 h. The solvent was removed in vacuo and purification by column chromatography (silica, 10% to 40% EtOAc in DCM) gave the title compound (42 mg). δH (CDCl$_3$) 9.00 (1H, br s), 8.65 (1H, br s), 7.57 (1H, s), 7.37 (1H, d, J 8.5 Hz), 7.30-7.24 (2H, m), 7.20-7.18 (2H, m), 7.16 (1H, d, J 9.7 Hz), 7.18-6.98 (3H, m), 6.52 (1H, br s), 6.33 (1H, d, J 9.7 Hz), 5.20 (2H, br s). LCMS (ES$^+$) RT 3.77 minutes, 430 (M+H)$^+$. LCMS (ES$^+$) RT 2.93 minutes, 401 (M+H)$^+$.

EXAMPLE 39

Ethyl 3-[(2-cyanophenyl)amino]-7-(1H-indol-5-yl)-6-oxo-6,7-dihydrothieno[2,3-b]pyridine-2-carboxylate From Intermediate 26 and 2-cyanoaniline by the method of Example 1. δH (CDCl$_3$) 8.96 (1H, br s), 8.67 (1H, br s), 7.89-7.74 (2H, m), 7.72-7.56 (2H, m), 7.48-7.44 (2H, m), 7.31-7.27 (3H, m), 6.79 (1H, br s), 6.66 (1H, d, J 9.7 Hz), 4.41 (2H, q, J 7.1 Hz), 1.42 (3H, t, J 7.1 Hz). LCMS (ES$^+$) RT 3.53 minutes, 455 (M+H)$^+$.

EXAMPLE 40

3-[(2-Cyanophenyl)amino]-7-(1H-indol-5-yl)-6-oxo-6,7-dihydrothieno[2,3-b]pyridine-2-carboxamide From Example 39 by the method of Example 38. δH (DMSO-d6) 11.21 (1H, br s), 9.33 (1H, m), 7.51-7.49 (1H, m), 7.44 (1H, d, J 1.8 Hz), 7.38 (1H, d, J 8.5 Hz), 7.28-7.19 (4H, m), 7.10 (1H, d, J 9.6 Hz), 6.87 (1H, dd, J 8.6, 2.0 Hz), 6.85-6.73 (1H, m), 6.72-6.63 (1H, m), 6.33 (1H, m), 6.20 (1H, d, J 9.6 Hz). LCMS (ES$^+$) RT 2.89 minutes, 426 (M+H)$^+$.

EXAMPLE 41

Ethyl 3-[(2-cyanophenyl)amino]-7-[1-(methylsulfonyl)-1H-indol-5-yl]-6-oxo-6,7-dihydrothieno[2,3-b]pyridine-2-carboxylate From Intermediate 27 and 2-cyanoaniline by the method of Example 1. δH (CDCl$_3$) 8.73 (1H, br s), 8.08 (1H, d, J 8.7 Hz), 7.64 (1H, s), 7.60 (1H, d, J 7.7 Hz), 7.53 (1H, d, J 3.8 Hz), 7.44 (1H, t, J 7.9 Hz), 7.32 (1H, dd, J 8.7, 1.8 Hz), 7.19 (1H, d, J 2.4 Hz), 7.09-7.04 (1H, d, J 9.7 Hz), 6.74 (1H, d, J 3.6 Hz), 6.42 (1H, d, J 9.7 Hz), 4.21 (2H, q, J 7.2 Hz), 3.15 (3H, s), 1.22 (3H, t, J 7.2 Hz). LCMS (ES$^+$) RT 3.68 minutes, 533 (M+H)$^+$.

EXAMPLE 42

Ethyl 3-[(2-cyanophenyl)amino]-7-(1-methyl-1H-indol-5-yl)-6-oxo-6,7-dihydrothieno[2,3-b]pyridine-2-carboxylate From Intermediate 28 and 2-cyanoaniline by the method of Example 1. δH (CDCl$_3$) 8.73 (1H, brs), 7.58-7.55 (2H, m), 7.47-7.41 (2H, m), 7.18 (1H, d, J 1.7 Hz), 7.13-7.11 (2H, m), 7.07-7.04 (2H, m), 6.52 (1H, d, J 2.4 Hz), 6.42 (1H, d, J 9.7 Hz), 4.19 (2H, q, J 7.1 Hz), 3.80 (3H, s), 1.19 (3H, t, J 7.1 Hz). LCMS (ES$^+$) RT 3.83 minutes, 469 (M+H)$^+$.

EXAMPLE 43

3-Anilino-7-(cyclopropylmethyl)-6-oxo-6,7-dihydrothieno[2,3-b]pyridine-2-carbonitrile A mixture of Intermediate 30 (225 mg, 0.73 mmol), aniline (0.082 mL, 0.9 mmol), caesium carbonate (342 mg, 1.08 mmol), BINAP (47 mg, 10 mol %) and tris(dibenzylideneacetone)dipalladium(0) (34 mg, 5 mol %) in toluene (7 mL) was heated at 105° C. for 24 h. The mixture was partitioned between EtOAc (75 mL) and water (75 mL). The organic layer was dried (Na$_2$SO$_4$) and concentrated in vacuo. Purification by column chromatography (silica, 5% THF in DCM) gave the title compound as a pale yellow solid (110 mg, 47%). δH (CDCl$_3$) 7.29-7.25 (2H, m), 7.19 (1H, d, J 9.7 Hz), 7.15-7.04 (1H, m), 7.00-6.97 (2H, m), 6.40 (1H, br s), 6.34 (1H, d, J 9.7 Hz), 3.91 (2H, d, J 7.1 Hz), 1.33-1.19 (1H, m), 0.80-0.45 (4H, m). LCMS (ES$^+$) 322.0 (M+H)$^+$.

EXAMPLE 44

Ethyl 3-anilino-7-(cyclopropylmethyl)-6-oxo-6,7-dihydrothieno[2,3-b]pyridine-2-carboxylate From Intermediate 29 and aniline by the method of Example 1. Pale yellow solid. δH (CDCl$_3$) 8.71 (1H, br s), 7.29-7.22 (2H, m), 7.10-6.97 (4H, m), 6.18 (1H, d, J 9.7 Hz), 4.27 (2H, q, J 7.1 Hz), 3.94 (2H, d, J 7.2 Hz), 1.40-1.33 (1H, m), 1.32 (3H, t, J 7.1 Hz), 0.53-0.48 (4H, m). LCMS (ES$^+$) RT 3.79 minutes, 369.0 (M+H)$^+$

EXAMPLE 45

3-Anilino-7-(cyclopropylmethyl)-6-oxo-6,7-dihydrothieno[2,3-b]pyridine-2-carboxamide A mixture of 1,1'-carbonyldiimidazole (433 mg, 2.7 mmol), and Intermediate 31 (650 mg, 1.91 mmol) in DMF (10 mL) was stirred at r.t. for 30 min. conc. NH$_3$ aq (15 mL) was added and the mixture stirred for 2 h then diluted with water (100 mL) and extracted with EtOAc (100 mL). The organic extract was washed with brine (3×50 mL), dried (Na$_2$SO$_4$) and concentrated in vacuo. Purification by column chromatography (silica, 15% to 25% EtOAc in DCM) gave the title compound as a white solid (210 mg, 32%). δH (CDCl$_3$) 8.62 (1H, br s), 7.09-7.03 (2H, m), 6.90 (1H, d, J 9.7 Hz), 6.88-6.82 (3H, m), 6.07 (1H, d, J 9.7 Hz), 5.28 (2H, br s), 3.78 (2H, d, J 7.1 Hz), 1.20-1.14 (1H, m), 0.40-0.33 (4H, m). LCMS (ES$^+$) 340.0 (M+H)$^+$.

EXAMPLE 46

3-Anilino-7-(cyclopropylmethyl)-N-methoxy-N-methyl-6-oxo-6,7-dihydrothieno[2,3-b]pyridine-2-carboxamide Prepared from Intermediate 31 and N,O-dimethylhydroxylamine hydrochloride by the method of Example 17. Pale yellow solid δH (CDCl$_3$) 9.98 (1H, brs), 7.24-7.19 (2H, m), 7.07 (1H, d, J 9.7 Hz), 7.04-7.00 (3H, m), 6.18 (1H, d, J 9.7 Hz), 3.96 (2H, d, J 7.1 Hz), 3.76 (3H, s), 3.26 (3H, s), 1.41-1.31 (1H, m), 0.54-0.50 (4H, m). LCMS (ES$^+$) 384.0 (M+H)$^+$.

EXAMPLE 47

Ethyl 7-(cyclopropylmethyl)-3-[(2,4-difluorophenyl) amino]-6-oxo-6,7-dihydrothieno[2,3-b]pyridine-2-carboxylate From Intermediate 29 and 2,4-difluoroaniline by the method of Example 1. Pale yellow solid. δH (CDCl$_3$) 8.68 (1H, br s), 7.25-7.19 (1H, m), 7.09 (1H, d, J 9.7 Hz), 7.06-6.91 (2H, m), 6.39 (1H, d, J 9.7 Hz), 4.45 (2H, q, J 7.1 Hz), 4.11 (2H, d, J 7.2 Hz), 1.57-1.50 (1H, m), 1.49 (3H, t, J 7.1 Hz), 0.70-0.65 (4H, m). LCMS (ES$^+$) 384.0 (M+H)$^+$.

EXAMPLE 48

7-(Cyclopropylmethyl)-3-[(2,4-difluorophenyl) amino]-6-oxo-6,7-dihydrothieno[2,3-b]pyridine-2-carboxamide 7-(Cyclopropyl methyl)-3-[(2,4-difluorophenyl)amino]-6-oxo-6,7-dihydrothieno[2,3-b]pyridine-2-carboxylic acid was prepared from Example 47 by the method of Intermediate 31. The title compound was prepared from this acid by the method of Example 46. δH (CDCl$_3$) 8.72 (1H, br s), 7.02-6.94 (2H, m), 6.89-6.82 (1H, m), 6.78-6.73 (1H, m), 6.26 (1H, d, J 9.7 Hz), 5.46 (2H, brs), 3.94 (2H, d, J 7.2 Hz), 1.37-1.29 (1H, m), 0.50-0.48 (4H, m). LCMS (ES$^+$) 376.0 (M+H)$^+$.

EXAMPLE 49

7-(Cyclopropylmethyl)-3-[(3-methylphenyl)amino]-6-oxo-6,7-dihydrothieno[2,3-b]pyridine-2-carbonitrile From Intermediate 30 and m-toluidine by the method of Example 1. Orange solid. δH (CDCl$_3$) 7.26-7.18 (3H, m), 6.94 (1H, d, J 7.6 Hz), 7.84 (1H, d, J 8.7 Hz), 6.39 (1H, d, J 9.7 Hz), 6.38 (1H, s), 3.97 (2H, d, J 7.2 Hz), 2.32 (3H, s), 1.41-1.31 (1H, m), 0.62-0.53 (4H, m). LCMS (ES$^+$) RT 3.593 minutes, 335.9 (M+H)$^+$.

EXAMPLE 50

7-(Cyclopropylmethyl)-3-[(4-fluoro-3-methylphenyl)amino]-6-oxo-6,7-dihydrothieno[2,3-b]pyridine-2-carbonitrile From Intermediate 30 and 4-fluoro-3-methylaniline by the method of Example 1. Yellow solid. δH (CDCl$_3$) 7.19 (1H, d, J 9.6 Hz), 7.0-6.87 (3H, m), 6.42 (1H, d, J 9.6 Hz), 6.36 (1H, s), 3.98 (2H, d, J 7.2 Hz), 2.27 (3H, s), 1.42-1.32 (1H, m), 0.67-0.52 (4H, m). LCMS (ES$^+$) RT 3.577 minutes, 354 (M+H)$^+$.

EXAMPLE 51

3-[(3-Chloro-4-fluorophenyl)amino]-7-(cyclopropylmethyl)-6-oxo-6,7-dihydrothieno[2,3-b]pyridine-2-carbonitrile From Intermediate 30 and 3-chloro-4-fluoroaniline by the method of Example 1. Yellow solid. δH (CDCl$_3$) 7.27-7.25 (1H, d, J 9.6 Hz), 7.16-7.11 (2H, m), 6.97-6.93 (1H, m), 6.48 (1H, d, J 9.6 Hz), 6.41 (1H, s), 4.0 (2H, d, J 7.2 Hz), 1.40-1.26 (1H, m), 0.65-0.54 (4H, m). LCMS (ES$^+$) RT 3.608 minutes, 374 (M+H)$^+$.

EXAMPLE 52

7-(Cyclopropylmethyl)-3-[(2,4-dimethylphenyl) amino]-6-oxo-6,7-dihydrothieno[2,3-b]pyridine-2-carbonitrile From Intermediate 30 and 2,4-dimethylaniline by the method of Example 1. Orange-yellow solid. δH (CDCl$_3$) 7.08-6.95 (4H, m), 6.34 (1H, d, J 9.6 Hz), 6.08 (1H, s), 3.97 (2H, d, J 7.2 Hz), 2.31 (3H, s), 2.28 (3H, s), 1.41-1.27 (1H, m), 0.62-0.51 (4H, m). LCMS (ES$^+$) RT 3.626 minutes, 350.0 (M+H)$^+$.

EXAMPLE 53

7-(Cyclopropylmethyl)-3-[(3,4-dimethylphenyl) amino]-6-oxo-6,7-dihydrothieno[2,3-b]pyridine-2-carbonitrile From Intermediate 30 and 3,4-dimethylaniline by the method of Example 1. Yellow solid. δH (CDCl$_3$) 7.19 (1H, d, J 9.6 Hz), 7.09 (1H, d, J 7.9 Hz), 6.88-6.81 (2H, m), 6.38 (1H, d, J 9.6 Hz), 6.31 (1H, s), 3.98 (2H, d, J 7.2 Hz), 2.22 (3H, s), 2.21 (3H, s), 1.41-1.34 (1H, m), 0.63-0.53 (4H, m). LCMS (ES$^+$) RT 3.693 minutes, 350.0 (M+H)$^+$.

EXAMPLE 54

7-(Cyclopropylmethyl)-3-[(3-methylphenyl)amino]-6-oxo-6,7-dihydrothieno[2,3-b]pyridine-2-carboxamide From Example 49 by the method of Example 22. δH (CDCl$_3$) 8.76 (1H, br s), 7.20-7.14 (2H, m), 6.93-6.85 (3H, m), 6.31 (1H, d, J 9.7 Hz), 5.46 (2H, br s), 4.02 (2H, d, J 7.1 Hz), 2.37 (3H, s), 1.48-1.38 (1H, m), 0.63-0.54 (4H, m). LCMS (ES$^+$) RT 3.153 minutes, 353.9 (M+H)$^+$.

EXAMPLE 55

7-(Cyclopropylmethyl)-3-[(4-fluoro-3-methylphenyl)amino]-6-oxo-6,7-dihydrothieno[2,3-b]pyridine-2-carboxamide From Example 50 by the method of Example 22. Yellow solid. δH (CDCl$_3$) 9.06 (1H, br s), 7.04 (1H, d, J 9.7 Hz), 7.0-6.80 (3H, m), 6.29 (1H, d, J 9.7 Hz), 5.34 (2H, br s), 4.0 (2H, d, J 7.1 Hz), 2.25 (3H, s), 1.46-1.37 (1H, m), 0.63-0.54 (4H, m). LCMS (ES$^+$) RT 3.207 minutes, 370.4 (M+H)$^+$.

EXAMPLE 56

7-(Cyclopropylmethyl)-3-[(3-chloro-4-fluorophenyl)amino]-6-oxo-6,7-dihydrothieno[2,3-b]pyridine-2-carboxamide From Example 51 by the method of Example 22. Yellow solid. δH (CDCl$_3$) 9.06 (1H, br s), 7.14-7.06 (3H, m), 6.96-6.92 (1H, m), 6.36 (1H, d, J 9.7 Hz), 5.4 (2H, br s), 4.02 (2H, d, J 7.1 Hz), 1.45-1.37 (1H, m), 0.64-0.55 (4H, m). LCMS (ES$^+$) RT 3.202 minutes, 391.9 (M+H)$^+$.

EXAMPLE 57

7-(Cyclopropylmethyl)-3-[(2,4-dimethylphenyl)amino]-6-oxo-6,7-dihydrothieno[2,3-b]pyridine-2-carboxamide From Example 52 by the method of Example 22. δH (CDCl$_3$) 9.2 (1H, br s), 7.01 (1H, s), 6.98 (2H, s), 6.89 (1H, d, J 9.8 Hz), 6.25 (1H, d, J 9.7 Hz), 5.33 (2H, br s), 4.03 (2H, d, J 7.1 Hz), 2.37 (3H, s), 2.33 (3H, s), 1.48-1.40 (1H, m), 0.65-0.56 (4H, m). LCMS (ES$^+$) RT 3.389 minutes, 368.0 (M+H)$^+$.

EXAMPLE 58

7-(Cyclopropylmethyl)-3-[(3,4-dimethylphenyl)amino]-6-oxo-6,7-dihydrothieno[2,3-b]pyridine-2-carboxamide From Example 53 by the method of Example 22. δH (CDCl$_3$) 8.9 (1H, br s), 7.10 (1H, d, J 9.7 Hz), 7.05 (1H, d, J 8 Hz), 6.87 (1H, s), 6.81 (1H, d, J 7.2 Hz), 6.27 (1H, d, J 9.7 Hz), 5.39 (2H, br s), 4.0 (2H, d, J 7.2 Hz), 2.24 (3H, s), 2.22 (3H, s), 1.45-1.37 (1H, m), 0.62-0.53 (4H, m). LCMS (ES$^+$) RT 3.321 minutes, 368.0 (M+H)$^+$.

EXAMPLE 59

Ethyl 3-[(2-cyano-3-methylphenyl)amino]-7-(cyclopropylmethyl)-6-oxo-6,7-dihydrothieno[2,3-b]pyridine-2-carboxylate From Intermediate 29 and 2-cyano-3-methylaniline by the method of Example 1. δH (CDCl$_3$) 8.75 (1H, br s), 7.33-7.29 (1H, m), 7.17 (1H, d, J 9.6 Hz), 6.97 (1H, d, J 7.5 Hz), 6.85 (1H, d, J 8.2 Hz), 6.36 (1H, d, J 9.6 Hz), 4.37 (2H, q, J 7.1 Hz), 4.03 (2H, d, J 7.1 Hz), 2.57 (3H, s), 1.48-1.38 (4H, m), 0.63-0.55 (4H, m). LCMS (ES$^+$) RT 4.044 minutes, 408.0 (M+H)$^+$.

EXAMPLE 60

3-[(2-Cyano-3-methylphenyl)amino]-7-(cyclopropylmethyl)-6-oxo-6,7-dihydrothieno[2,3-b]pyridine-2-carboxamide From Example 59 by the method of Example 38. Yellow solid. δH (CDCl$_3$) 8.4 (1H, br s), 7.30-7.22 (1H, m), 7.19 (1H, d, J 9.6 Hz), 6.94 (1H, d, J 7.6 Hz), 6.72 (1H, d, J 8.2 Hz), 6.42 (1H, d, J 9.6 Hz), 5.78 (2H, br s), 4.02 (2H, d, J 7.2 Hz), 2.56 (3H, s), 1.44-1.35 (1H, m), 0.64-0.55 (4H, m). LCMS (ES$^+$) RT 3.05 minutes, 378.9 (M+H)$^+$.

EXAMPLE 61

3-Anilino-7-(cyclopropylmethyl)-6-oxo-N-(2-piperidin-1-ylethyl)-6,7-dihydrothieno[2,3-b]pyridine-2-carboxamide From Intermediate 31 and 1-(2-aminoethyl)piperidine by the method of Example 17. δH (CDCl$_3$) 7.22-7.17 (2H, m), 7.13 (1H, d, J 9.7 Hz), 6.98-6.92 (3H, m), 6.79 (1H, br s), 6.26 (1H, d, J 9.7 Hz), 3.97 (2H, d, J 7.1 Hz), 3.44-3.40 (2H, m), 2.50-2.48 (2H, m), 2.47-2.39 (4H, m), 1.54-1.51 (4H, m), 1.41-1.32 (3H, m), 0.54-0.50 (4H, m). LCMS (ES$^+$) RT 2.42 minutes, 451 (M+H)$^+$.

EXAMPLE 62

Ethyl 3-[(3-bromophenyl)amino]-7-(cyclopropylmethyl)-6-oxo-6,7-dihydrothieno[2,3-b]pyridine-2-carboxylate From Intermediate 29 and 3-bromoaniline by the method of Example 1. δH (CDCl$_3$) 8.50 (1H, br s), 7.25-6.99 (4H, m), 6.86-6.82 (1H, m), 6.15 (1H, d, J 9.7 Hz), 4.16 (2H, q, J 7.4 Hz), 3.84 (2H, d, J 7.2 Hz), 1.86 (3H, t, J 7.4 Hz), 1.05-0.95 (1H, m), 0.43-0.38 (4H, m). LCMS (ES$^+$) RT 4.54 minutes, 448/449 ($^{79}$Br/$^{80}$Br) (M+H)$^+$.

EXAMPLE 63

3-[(3-bromophenyl)amino]-7-(cyclopropylmethyl)-6-oxo-6,7-dihydrothieno[2,3-b]pyridine-2-carboxamide From Example 62 by the method of Example 38. δH (CDCl$_3$) 8.72 (1H, br s), 7.14-7.05 (4H, m), 6.89-6.86 (1H, m), 6.30 (1H, d, J 9.6 Hz), 5.57 (2H, s), 3.95 (2H, d, J 7.1 Hz), 0.54-0.48 (5H, m). LCMS (ES$^+$) RT 3.202 minutes, 419 (M+H)$^+$.

EXAMPLE 64

Ethyl 3-anilino-6-oxo-7-(3-thienyl)-6,7-dihydrothieno[2,3-b]pyridine-2-carboxylate A mixture of Intermediate 34 (20 mg, 0.63 mmol), 3-thiophene boronic acid (161 mg, 1.26 mmol) and copper (II) acetate (115 mg, 0.63 mmol) in pyridine (0.29 mL) was stirred at r.t. for 24 h. More copper (II) acetate (115 mg, 0.63 mmol) was added and reaction continued for a further 24 h. The mixture was diluted with DCM, washed with 2M HCl aq, dried (MgSO$_4$) and concentrated in vacuo. Purification by column chromatography (silica, 20% EtOAc in hexane) gave the title compound (30 mg, 12%). δH (CDCl$_3$) 8.67 (1H, br s), 7.48-7.45 (2H, m), 7.29-7.25 (2H, m), 7.10-7.05 (5H, m), 6.23 (1H, d, J 9.8 Hz), 4.20 (2H, q, J 7.1 Hz), 1.24 (3H, t, J 7.1 Hz). LCMS (ES+) RT 3.898 minutes, 397 (M+H)+

EXAMPLE 65

3-Anilino-6-oxo-7-(3-thienyl)-6,7-dihydrothieno[2,3-b]pyridine-2-carboxamide

A mixture of Example 64 (129 mg), 2-ethoxyethanol and liquid ammonia was placed in a sealed pressure vessel and heated at 80° C. and 400 p.s.i. for 24 h. The volatiles were removed in vacuo and the residue purified by column chromatography (silica, 50% to 100% EtOAc in hexane) to give the title compound (20 mg). δH (CDCl$_3$) 8.75 (1H, brs), 7.36-7.34 (2H, m), 7.16-7.11 (2H, m), 7.03 (1H, d, J 9.7 Hz), 6.99-6.88 (4H, m), 6.17 (1H, d, J 9.7 Hz), 5.47 (2H, br s). LCMS (ES+) RT 2.927 minutes, 368 (M+H)+

EXAMPLE 66

Ethyl 3-[(2-cyanophenyl)amino]-6-oxo-7-(3-thienyl)-6,7-dihydrothieno[2,3-b]pyridine-2-carboxylate A mixture of Intermediate 35 (270 mg, 0.7 mmol), 2-cyano aniline (122 mg, 0.84 mmol), caesium carbonate (319 mg, 0.98 mmol), BINAP (87 mg, 20 mol %) and tris(dibenzylideneacetone)dipalladium(0) (64 mg, 10 mol %) in toluene (1 mL) was heated at reflux for 3 days. Brine was added and the mixture extracted with EtOAc. The organic extract was dried (MgSO$_4$) and concentrated in vacuo. Purification by column chromatography (silica, 20% to 40% EtOAc in hexane) gave the title compound (120 mg, 41%). δH (CDCl$_3$) 8.7 (1H, br s), 7.67 (1H, d, J 7.8 Hz), 7.58 (2H, m), 7.50 (1H, t, J 7.9 Hz), 7.26-7.09 (4H, m), 6.46 (1H, d, J 9.8 Hz), 4.33 (2H, q, J 7.1 Hz), 1.35 (3H, t, J 7.2 Hz). LCMS (ES+) RT 3.624 minutes, 421.9 (M+H)+

EXAMPLE 67

3-[(2-Cyanophenyl)amino]-6-oxo-7-(3-thienyl)-6,7-dihydrothieno[2,3-b]pyridine-2-carboxamide A mixture of Example 66 (100 mg), 2-ethoxyethanol and liquid ammonia was placed in a sealed pressure vessel and heated at 80° C. and 400 psi for 48 h. The volatiles were removed in vacuo and the residue purified by column chromatography (silica, EtOAc) to give the title compound (30 mg). δH (CDCl$_3$) 7.59-7.46 (4H, m), 7.28-7.21 (3H, m), 7.20 (1H, t, J 2.0 Hz), 7.01 (1H, d, J 8.3 Hz), 6.49 (1H, d, J 9.7 Hz), 5.55 (2H, br s). LCMS (ES+) RT 2.845 minutes, 392.9 (M+H)+

EXAMPLE 68

Ethyl 3-[(4-fluoro-3-methylphenyl)amino]-6-oxo-7-(3-thienyl)-6,7-dihydrothieno[2,3-b]pyridine-2-carboxylate From Intermediate 37 by the method of Example 64. δH (CDCl$_3$) 8.7 (1H, br s), 7.55 (1H, br s), 7.28 (1H, br s), 7.17 (1H, m), 7.07-6.99 (4H, m), 6.33 (1H, d, J 9.8 Hz), 4.30 (2H, q, J 7.2 Hz), 2.29 (3H, s), 1.28 (3H, t, J 7.1 Hz). LCMS (ES+) RT 4.276 minutes, 429 (M+H)+

EXAMPLE 69

3-[(4-Fluoro-3-methylphenyl)amino]-6-oxo-7-(3-thienyl)-6,7-dihydrothieno[2,3-b]pyridine-2-carboxamide From Example 68 by the method of Example 65. White solid. δH (CDCl$_3$) 9.03 (1H, br s), 7.48-7.45 (2H, m), 7.09-7.08 (1H, m), 7.03-7.00 (1H, d, J 9.8 Hz), 6.92-6.82 (3H, m), 6.27 (1H, d, J 9.8 Hz), 5.12 (2H, br s), 2.19 (3H, s). LCMS (ES+) RT 3.144 minutes, 401 (M+H)+

EXAMPLE 70

Ethyl 3-[(2,4-difluorophenyl)amino]-6-oxo-7-(3-thienyl)-6,7-dihydrothieno[2,3-b]pyridine-2-carboxylate From Intermediate 35 and 2,4-difluoroaniline by the method of Example 1. δH (CDCl$_3$) 8.64 (1H, br s), 7.65-7.62 (2H, m), 7.30-7.22 (2H, m), 7.15 (1H, d, J 9.8 Hz), 7.09-6.94 (2H, m), 6.45 (1H, d, J 9.8 Hz), 4.39 (2H, q, J 7.1 Hz), 1.41 (3H, t, J 7.1 Hz). LCMS (ES+) RT 3.962 minutes, 434 (M+H)+

EXAMPLE 71

Ethyl 6-oxo-7-phenyl-3-(pyridin-3-ylamino)-6,7-dihydrothieno[2,3-b]pyridine-2-carboxylate From Intermediate 5 and 3-aminopyridine by method of Example 1. Pale yellow solid. δH (CDCl$_3$) 8.56 (1H, br s), 8.35-8.32 (1H, m), 8.22-8.20 (1H, m), 7.45-7.37 (3H, m), 7.25-7.16 (3H, m), 7.11-7.06 (1H, m), 6.98 (1H, d, J 9.8 Hz), 6.21 (1H, d, J 9.8 Hz), 4.07 (2H, q, J 7.1 Hz), 1.10 (3H, t, J 7.1 Hz). LCMS (ES+) 392.1 (M+H)+.

EXAMPLE 72

Ethyl 3-[(2-chloropyridin-3-yl)amino]-6-oxo-7-phenyl-6,7-dihydrothieno[2,3-b]pyridine-2-carboxylate From Intermediate 5 and 3-amino-2-chloropyridine by method of Example 1. Off-white solid. δH (CDCl$_3$) 8.52 (1H, br s), 8.02 (1H, d, J 4.5 Hz), 7.57-7.48 (3H, m), 7.34 (2H, m), 7.25-7.08 (3H, m), 6.42 (1H, d, J 9.6 Hz), 4.21 (2H, q, J 7.0 Hz), 1.23 (3H, t, J 7.0 Hz). LCMS (ES+) 426.0 ($^{35}$Cl)(M+H)+.

EXAMPLE 74

3-[(6-Methylpyridin-2-yl)amino]-6-oxo-7-phenyl-6,7-dihydrothieno[2,3-b]pyridine-2-carbonitrile Phosphorous trichloride (0.175 mL, 2.01 mmol) was added to a solution of Intermediate 38 (500 mg, 1.34 mmol) in chloroform (15 mL) and the mixture heated at 90° C. for 4 h. The mixture was cooled, diluted with DCM, washed with water, dried (MgSO$_4$) and concentrated in vacuo. Purification by column chromatography (silica, 10% EtOAc in DCM) gave the title compound (75 mg). δH (CDCl$_3$) 7.65-7.40 (6H, m), 7.38-7.25 (2H, m), 6.75 (1H, d, J 7.4 Hz), 6.60-6.40 (2H, m), 2.38 (3H, s). LCMS (ES+) RT 3.15 minutes, 359 (M+H)+.

EXAMPLE 75

3-[(6-Methylpyridin-2-yl)amino]-6-oxo-7-phenyl-6,7-dihydrothieno[2,3-b]pyridine-2-carboxamide From Example 74 by the method of Example 22. δH (CDCl$_3$) 9.00 (1H, br s), 7.65-7.45 (4H, m), 7.42-7.25 (3H, m), 6.70 (1H, d, J 7.4 Hz), 6.54 (1H, d, J 8.1 Hz), 6.46 (1H, d, J 9.7 Hz), 5.44 (2H, br s), 2.36 (3H, s). LCMS (ES$^+$) RT 2.18 minutes, 377 (M+H)$^+$.

EXAMPLE 76

3-[(6-Chloropyridin-2-yl)amino]-6-oxo-7-phenyl-6,7-dihydrothieno[2,3-b]pyridine-2-carbonitrile Sodium hydride (90 mg, 60% in mineral oil, 2.25 mmol) was added to a solution of Intermediate 11 (500 mg, 1.87 mmol) in DMSO. After 10 min, 2,6-dichloropyridine (277 mg, 1.87 mmol) was added and the mixture heated at 70° C. overnight. The mixture was poured in to brine and this was then extracted with EtOAc (×3). The organics were dried (MgSO$_4$) and concentrated in vacuo. Purification by column chromatography (silica, 10% EtOAc in DCM) gave the title compound as a pale yellow solid (440 mg, 62%). δH (CDCl$_3$) 7.58-7.41 (5H, m), 7.28-7.24 (2H, m), 7.16 (1H, br s), 6.81 (1H, d, J 7.6 Hz), 6.57 (1H, d, J 8.1 Hz), 6.50 (1H, d, J 9.7 Hz). LCMS (ES$^+$) RT 3.34 minutes, 379 (M+H)$^+$.

EXAMPLE 77

3-[(6-Chloropyridin-2-yl)amino]-6-oxo-7-phenyl-6,7-dihydrothieno[2,3-b]pyridine-2-carboxamide From Example 76 by the method of Example 22. δH (CDCl$_3$) 9.55 (1H, br s), 7.79-7.66 (4H, m), 7.61-7.58 (3H, m), 7.48 (2H, br s), 6.95 (1H, d, J 7.5 Hz), 6.84 (1H, d, J 8.1 Hz), 6.54 (1H, d, J 9.7 Hz). LCMS (ES$^+$) RT 2.91

EXAMPLE 78

Ethyl 3-[(2-cyanophenyl)amino]-7-[4-(methylthio)phenyl]-6-oxo-6,7-dihydrothieno[2,3-b]pyridine-2-carboxylate From Intermediate 39 and 2-cyanoaniline by the method of Example 1. δH (CDCl$_3$) 8.81 (1H, br s), 7.68 (1H, br d, J 7.8 Hz), 7.53-7.45 (3H, m), 7.36-7.32 (2H, m), 7.28-7.24 (1H, m), 7.18-7.11 (2H, m), 6.48 (1H, d, J 9.7 Hz), 4.32 (2H, m), 2.58 (3H, s), 1.34 (3H, m). LCMS (ES$^+$) RT 3.96 minutes, 462 (M+H)$^+$.

EXAMPLE 79

Ethyl 3-[(2-cyanophenyl)amino]-7-[4-(methylsulfinyl)phenyl]-6-oxo-6,7-dihydrothieno[2,3-b]pyridine-2-carboxylate A mixture of Example 78 (1.0 g, 2.17 mmol) and m-chloroperbenzoic acid (534 mg, 1 eq) in DCM (50 mL) was stirred at r.t. for 2 h. The mixture was diluted with DCM, washed with NaHCO$_3$ aq, dried (MgSO$_4$) and concentrated in vacuo. Purification by column chromatography (silica, 50% EtOAc in DCM) gave the title compound (850 mg, 82%). δH (CDCl$_3$) 8.80 (1H, s), 8.12-7.70 (2H, m), 7.65-7.53 (3H, m), 7.50 (1H, t, J 7.4 Hz), 7.27 (1H, d, J 9.8 Hz), 7.17-7.09 (2H, m), 6.45 (1H, d, J 9.8 Hz), 4.28 (2H, q, J 7.1 Hz), 2.83 (3H, s), 1.30 (3H, t, J 7.1 Hz). LCMS (ES$^+$) RT 3.16 minutes, 478 (M+H)$^+$.

EXAMPLE 80

3-[(2-Cyanophenyl)amino]-1-[4-(methylsulfinyl)phenyl]-6-oxo-6,7-dihydrothieno[2,3-b]pyridine-2-carboxamide From Example 79 by the method of Example 38. δH (DMSO-d6) 9.32 (1H, br s), 7.85-7.75 (2H, m), 7.62-7.57 (3H, m), 7.38-7.33 (3H, m), 7.19 (1H, d, J 9.7 Hz), 6.91 (1H, t, J 7.5 Hz), 6.76 (1H, d, J 8.3 Hz), 6.30 (1H, d, J 9.7 Hz), 2.70 (3H, s). LCMS (ES$^+$) RT 2.57 minutes, 449 (M+H)$^+$.

EXAMPLE 81

Ethyl 3-anilino-7-[4-(methylthio)phenyl]-6-oxo-6,7-dihydrothieno[2,3-b]pyridine-2-carboxylate From Intermediate 39 and aniline by the method of Example 1. δH (CDCl$_3$) 8.79 (1H, br s), 7.47-7.19 (10H, m), 6.36 (1H, d, J 9.6 Hz), 4.28 (2H, q, J 7.1 HZ), 2.57 (3H, s), 1.32 (3H, t, J 7.1 Hz). LCMS (ES$^+$) RT 4.268 minutes, 437 (M+H)$^+$.

EXAMPLE 82

Ethyl 3-anilino-7-[4-(methylsulfinyl)phenyl]-6-oxo-6,7-dihydrothieno[2,3-b]pyridine-2-carboxylate From Example 81 by the method of Example 79. δH (CDCl$_3$) 8.70 (1H, s), 7.85 (1H, br s), 7.75 (1H, br s), 7.53 (2H, m), 7.31-7.27 (2H, m), 7.10-7.08 (4H, m), 6.27 (1H, d, J 9.8 Hz), 4.20 (2H, q, J 7.1 Hz), 2.76 (3H, s), 1.24 (3H, t, J 6.7 Hz). LCMS (ES$^+$) RT 3.325 minutes, 452.8 (M+H)$^+$.

EXAMPLE 83

Ethyl 3-[(3-methylphenyl)amino]-7-[4-(methylthio)phenyl]-6-oxo-6,7-dihydrothieno[2,3-b]pyridine-2-carboxylate From Intermediate 39 and m-toluidine by the method of Example 1. δH (CDCl$_3$) 8.65 (1H, br s), 7.36-7.25 (2H, m), 7.23-7.11 (4H, m), 6.92-6.87 (3H, m), 6.27 (1H, d, J 9.7 Hz), 4.18 (2H, q, J 7.12 Hz), 2.48 (3H, s), 2.27 (3H, s), 1.22 (3H, t, J 7.1 Hz). LCMS (ES$^+$) RT 4.613 minutes, 451 (M+H)$^+$.

EXAMPLE 84

Ethyl 3-[(3-methylphenyl)amino]-7-[4-(methylsulfonyl)phenyl]-6-oxo-6,7-dihydrothieno[2,3-b]pyridine-2-carboxylate A mixture of Example 83 (100 mg, 0.22 mmol) and m-chloroperbenzoic acid (54 mg, 2 eq) in DCM (5 mL) was stirred at r.t. overnight. The mixture was diluted with DCM, washed with NaHCO$_3$ aq, dried (MgSO$_4$) and concentrated in vacuo. Purification by column chromatography (silica, 50% EtOAc in hexane) gave the title compound (10 mg). δH (CDCl$_3$) 8.66 (1H, br s), 8.11 (2H, d, J 8.5 Hz), 7.59 (2H, d, J 8.5 Hz), 7.19-7.13 (2H, m), 6.94-6.89 (3H, m), 6.26 (1H, d, J 9.8 Hz), 4.19 (2H, q, J 7.1 Hz), 3.08 (3H, s), 2.28 (3H, s), 1.18 (3H, t, J 7.1 Hz). LCMS (ES$^+$) RT 3.713 minutes, 483 (M+H)$^+$.

EXAMPLE 85

3-[(3-Methylphenyl)amino]-7-[4-(methylsulfonyl)phenyl]-6-oxo-6,7-dihydrothieno[2,3-b]pyridine-2-carboxamide From Example 84 by the method of Example 38. δH (CDCl$_3$) 8.21 (2H, d, J 8.6 Hz), 7.70 (2H, d, J 8.6 Hz), 7.26-7.21 (3H, m), 6.97-6.92 (3H, m), 6.40 (1H, d, J 9.8 Hz), 3.17 (3H, s), 2.36 (3H, s). LCMS (ES$^+$) RT 2.954 minutes, 454 (M+H)$^+$.

EXAMPLE 86

Ethyl 3-anilino-6-oxo-7-[4-(pyrrolidin-1-ylmethyl)phenyl]-6,7-dihydrothieno[2,3-b]pyridine-2-carboxylate From Intermediate 41 and aniline by the method of Example 1. δH (CDCl$_3$) 8.62 (1H, br s), 7.60-7.53 (4H, m), 7.37-7.25 (4H, m), 7.18-7.07 (4H, m), 6.26 (1H, d, J 9.8 Hz), 4.19 (2H, q, J 7.1 Hz), 2.63 (4H, m), 1.82 (4H, m), 1.22 (3H, t, J 7.09 Hz). LCMS (ES$^+$) RT 2.479 minutes, 474 (M+H)$^+$.

EXAMPLE 87

Ethyl 3-[(2,4-difluorophenyl)amino]-7-{4-[2-(2-methyl-1H-imidazol-1-yl)ethoxy]phenyl}-6-oxo-6,7-dihydrothieno[2,3-b]pyridine-2-carboxylate A mixture of Intermediate 45 (375 mg, 0.68 mmol), 2-methylimidazole (84 mg, 1.02 mmol) and caesium carbonate (332 mg, 1.02 mmol) in DMF (5 mL) was heated at 80° C. for 18 h. The mixture was partitioned between DCM and water and the aqueous phase was extracted with DCM (2×20 mL). The combined organics were washed with water (2×20 mL) and brine, dried (MgSO$_4$) and concentrated in vacuo. Purification by column chromatography (silica, 5% MeOH in DCM) gave the title compound (165 mg). δH (DMSO-d6) 8.65 (1H, s), 7.43-7.30 (4H, m), 7.20-7.10 (4H, m), 6.77 (1H, d, J 1.2 Hz), 6.40 (1H, d, J 9.8 Hz), 4.40-4.34 (4H, br m), 4.17 (2H, q, J 7.1 Hz), 2.47 (3H, s), 1.19 (3H, t, J 7.1 Hz). LCMS (ES$^+$) RT 1.929 minutes, 551 (M+H)$^+$.

EXAMPLE 88

3-[(2,4-Difluorophenyl)amino]-7-{4-[2-(2-methyl-1H-imidazol-1-yl)ethoxy]phenyl}-6-oxo-6,7-dihydrothieno[2,3-b]pyridine-2-carboxamide From Example 87 by the method of Example 38. δH (d$_3$-MeOD) 7.32-7.25 (3H, m), 7.07-6.91 (5H, m), 6.86-6.74 (2H, m), 6.34 (1H, d, J 9.6 Hz), 4.31-4.25 (4H, br m), 2.36 (3H, s). LCMS (ES$^+$) RT 2.356 minutes, 522 (M+H)$^+$.

EXAMPLE 89

Ethyl 3-[(2,4-difluorophenyl)amino]-6-oxo-7-(4-vinylphenyl)-6,7-dihydrothieno[2,3-b]pyridine-2-carboxylate From Intermediate 46 and 2,4-difluoroaniline by the method of Example 1. δH (CDCl$_3$) 8.5 (1H, br s), 7.6 (2H, d, J 2.3 Hz), 7.28 (2H, d, J 2.4 Hz), 7.23-6.68 (5H, m), 6.309 (1H, d, J 9.8 Hz), 5.78 (1H, d, J 17 Hz), 5.32 (1H, d, J 11.8 Hz), 4.2 (2H, q, J 7.1 Hz), 1.22 (3H, t, J 7.1 Hz). LCMS (ES$^+$) RT 4.225 minutes, 453 (M+H)$^+$.

EXAMPLE 90

Ethyl 3-anilino-6-oxo-7-(4-vinylphenyl)-6,7-dihydrothieno[2,3-b]pyridine-2-carboxylate From Intermediate 46 and aniline by the method of Example 1. δH (CDCl$_3$) 8.72 (1H, br s), 7.53-7.50 (2H, m), 7.32-7.26 (4H, m), 7.13-7.05 (4H, m), 6.72 (1H, dd, J 17.5, 11.0 Hz), 6.27 (1H, d, J 9.8 Hz), 5.78 (1H, d, J 17.5 Hz), 5.32 (1H, d, J 11.0 Hz), 4.18 (2H, q, J 7.1 Hz), 1.22 (3H, t, J 7.1 Hz). LCMS (ES$^+$) RT 4.324 minutes, 417 (M+H)$^+$.

EXAMPLE 91

3-Anilino-6-oxo-7-(4-vinylphenyl)-6,7-dihydrothieno[2,3-b]pyridine-2-carboxamide From Example 90 by the method of Example 38. δH (CDCl$_3$) 8.96 (1H, br s), 7.54 (2H, d, J 10.5 Hz), 7.29-7.03 (8H, m), 6.72 (1H, dd, J 17.6, 11.0 Hz), 6.31 (1H, d, J 9.8 Hz), 5.78 (1H, dd, J 17.6, 0.4 Hz), 5.32 (1H, d, J 11.0 Hz), 5.23 (2H, s). LCMS (ES$^+$) RT 3.214 minutes, 388 (M+H)$^+$.

EXAMPLE 92

Ethyl 3-anilino-7-[4-(1,2-dihydroxyethyl)phenyl]-6-oxo-6,7-dihydrothieno[2,3-b]pyridine-2-carboxylate A mixture of Example 91 (134 mg, 0.32 mmol), 4-methylmorpholine N-oxide (113 mg, 0.97 mmol) and osmium tetroxide (98 mg of a 2.5 wt. % solution in 2-methyl-2-propanol, 0.1 mmol) in acetone/water (8:1) (10 mL) and EtOAc (10 mL) was stirred at r.t. overnight. Sodium sulfite solution (sat. 10 mL) was added and the mixture stirred for 15 min. The mixture was extracted with EtOAc (2×20 mL) and the combined organics washed with brine, dried (MgSO$_4$) and concentrated in vacuo. Purification by column chromatography (silica, EtOAc) gave the title compound (104 mg, 72%). δH (DMSO-d6) 8.70 (1H, s), 7.54-7.49 (2H, m), 7.37-7.35 (2H, m), 7.28-7.23 (2H, m), 7.15 (1H, d, J 9.7 Hz), 7.07-7.00 (3H, m), 6.31 (1H, d, J 9.7 Hz), 5.35 (1H, d, J 4.3 Hz), 4.75 (1H, t, J 5.7 Hz), 4.59-4.58 (1H, m), 4.08 (2H, q, J 7.1 Hz), 4.03-4.00 (1H, m), 3.48-3.45 (1H, br m), 1.09 (3H, t, J 7.1 Hz). LCMS (ES$^+$) RT 3.3 minutes, 451 (M+H)$^+$.

EXAMPLE 93

3-Anilino-7-[4-(1,2-dihydroxyethyl)phenyl]-6-oxo-6,7-dihydrothieno[2,3-b]pyridine-2-carboxamide From Example 91 by the method of Example 92. δH (CDCl$_3$) 8.93 (1H, s), 7.56 (10H, m), 6.31 (1H, d, J 9.7 Hz), 5.23 (2H, s), 4.85-4.82 (1H, m), 3.79-3.75 (1H, m), 3.66-3.59 (2H, m), 2.22 (1H, br s). LCMS (ES$^+$) RT 2.62 minutes, 422 (M+H)$^+$.

EXAMPLE 94

3-[(2,4-Difluorophenyl)amino]-7-(4-{[(2R)-2,3-dihydroxypropyl]oxy}Phenyl)-6-oxo-6,7-dihydrothieno[2,3-b]pyridine-2-carbonitrile A mixture of Intermediate 50 (49 mg, 0.1 mmol) and Dowex (50×4 200) (cat. amount) in EtOH (2 mL) and water (0.5 mL) was heated at 50° C. overnight. The mixture was diluted with EtOH (3 mL) and filtered hot. The filtrate was concentrated in vacuo to give the title compound (33 mg). δH (CDCl$_3$) 7.30 (1H, d, J 9.7 Hz), 7.25-7.23 (2H, m), 7.11-7.03 (3H, m), 6.92-6.82 (2H, m), 6.49 (1H, d, J 9.7 Hz), 6.10 (1H, s), 4.12-4.05 (3H, m), 3.81 (1H, dd, J 11.3, 3.7 Hz), 3.71 (1H, dd, J 11.3, 5.0 Hz). LCMS (ES$^+$) RT 2.864 minutes, 470 (M+H).

EXAMPLE 95

Ethyl 3-[(2,4-difluorophenyl)amino]-7-(2-nitrophenyl)-6-oxo-6,7-dihydrothieno[2,3-b]pyridine-2-carboxylate A mixture of Intermediate 51 (423 mg, 1.0 mmol), 2,4-difluoroaniline (0.122 mL, 1.2 mmol), caesium carbonate (456 mg, 1.4 mmol), BINAP (62 mg, 10 mol %) and tris(dibenzylideneacetone)dipalladium(0) (46 mg, 5 mol %) in toluene (10 mL) was heated at reflux for 24 h. The mixture was diluted with DCM, washed with 1M HCl aq and 10% NaOH aq, dried (Na$_2$SO$_4$) and concentrated in vacuo. Purification by column chromatography (silica, 0 to 2% THF in DCM) gave the title compound as a yellow gum (411 mg, 87%). δH (DMSO-d6) 8.78 (1H, s), 8.42 (1H, dd, J 1.3, 8.1 Hz), 8.14-8.10 (1H, m), 8.03-7.97 (2H, m), 7.50-7.38 (2H, m), 7.31 (1H, d, J 9.8 Hz), 7.21-7.16 (1H, m), 6.47 (1H, d, J 9.8 Hz), 4.22 (2H, q, J 7.1 Hz), 1.22 (3H, t, J 7.1 Hz). LCMS (ES$^+$) RT 3.916 minutes, 471.9 (M+H)$^+$.

EXAMPLE 96

3-[(2,4-Difluorophenyl)amino]-7-(2-nitrophenyl)-6-oxo-6,7-dihydrothieno[2,3-b]pyridine-2-carboxamide CDI (211 mg, 1.29 mmol) was added to crude Intermediate 52 (0.86 mmol) in DMF (10 mL). After 90 min, conc. ammonia (5 mL) was added and the mixture stirred for 4 h. Volatiles were removed in vacuo and the residue partitioned between DCM and water. The DCM layer was dried (Na$_2$SO$_4$) and concentrated in vacuo. Purification by column chromatography (silica, 20% EtOAc in DCM) gave the title compound as a yellow solid (218 mg, 57%). δH (DMSO-d6) 9.21 (1H, s), 8.43-8.41 (1H, m), 8.15-8.11 (1H, m), 8.05-8.03 (1H, m), 8.00-7.96 (1H, m), 7.49-7.39 (3H, m), 7.36 (1H, d, J 9.7 Hz), 7.14-7.08 (2H, m), 6.47 (1H, d, J 9.7 Hz). LCMS (ES$^+$) RT 3.125 minutes, 442.8 (M+H)$^+$.

EXAMPLE 97

Ethyl 3-anilino-4-methyl-6-oxo-7-phenyl-6,7-dihydrothieno[2,3-b]pyridine-2-carboxylate A mixture of Intermediate 57 (1.20 g, 3.06 mmol), aniline (0.334 mL, 3.67 mmol), caesium carbonate (1.40 g, 4.28 mmol), BINAP (190 mg, 0.306 mmol) and tris(dibenzylideneacetone)dipalladium(0) (140 mg, 0.153 mmol) in toluene (30 mL) was heated at reflux for 3 days. The solvent was removed in vacuo and the residue partitioned between DCM and water.

The organic phase was washed with 1M HCl aq, dried (Na$_2$SO$_4$) and concentrated in vacuo. Purification by column chromatograph (silica, 2% THF in DCM) gave the title compound as a yellow powder (1.15 g, 77%). δH (CDCl$_3$) 8.01 (1H, s), 7.47-7.55 (3H, m), 7.33-7.37 (2H, m), 7.17-7.22 (2H, m), 6.93 (1H, t, J 7.4 Hz), 6.80 (2H, d, J 7.9 Hz), 6.25 (1H, s), 4.16 (2H, q, J 7.1 Hz), 2.03 (3H, s), 1.19 (3H, t, J 7.1 Hz). LCMS (ES$^+$) RT 4.04 minutes, 405 (M+H)$^+$

EXAMPLE 98

3-Anilino-4-methyl-6-oxo-7-phenyl-6,7-dihydrothieno[2,3-b]pyridine-2-carboxamide A mixture of Example 97 (150 mg, 0.37 mmol), ethoxyethanol and liquid ammonia was heated in a sealed vessel at 80° C. at 400 psi for 16 h. The mixture was concentrated in vacuo and the solid recrystallised from MeOH to give the title compound as a yellow solid (92 mg, 66%). δH (DMSO-d6) 8.05 (1H, s), 7.68-7.59 (3H, m), 7.53-7.51 (2H, m), 7.5 (1H, br), 7.24-7.20 (2H, m), 6.80 (1H, t, J 7.3 Hz), 6.64 (2H, d, J 7.7 Hz), 6.29 (1H, s), 2.22 (3H, s). LCMS (ES$^+$) RT 3.074 minutes, 375.9 (M+H)$^+$

EXAMPLE 99

3-[(2,4-Difluorophenyl)amino]-6-oxo-7-phenyl-6,7-dihydrothieno[2,3-b]pyridine-2-sulfonamide A mixture of Intermediate 60 (50 mg), trifluoroacetic acid (2 mL) and DCM (10 mL) was stirred at r.t. overnight. Solvents were removed in vacuo and the residue azeotroped with toluene (×3). The residue was dissolved in DCM, treated with triethylamine (3 mL) and the mixture concentrated in vacuo. Purification by column chromatography (silica, 5% EtOAc in DCM) gave the title compound (25 mg, 63%). δH (CDCl$_3$) 7.51-7.47 (3H, m), 7.33-7.29 (2H, m), 7.07-6.98 (3H, m), 6.93-6.78 (2H, m), 6.38 (1H, d, J 9.2 Hz), 4.87 (2H, br s). LCMS (ES$^+$) RT 3.17 minutes, 434 (M+H)$^+$.

EXAMPLE 100

Ethyl 3-anilino-7-[2-(2-methoxyethoxy)ethyl]-6-oxo-6,7-dihydrothieno[2,3-b]pyridine-2-carboxylate From Intermediate 61 and aniline by the method of Example 1. δH (CDCl$_3$) 8.85 (1H, brs), 7.42-7.30 (2H, m), 7.24-7.19 (4H, m), 6.34 (1H, d, J 9.7 Hz), 4.45 (2H, q, J 7.1 Hz), 4.41-3.98 (2H, m), 3.79-3.75 (2H, m), 3.65-3.62 (2H, m), 3.60-3.55 (2H, m), 3.47 (3H, s), 1.49 (3H, t, J 7.1 Hz). LCMS (ES$^+$) 417.1 (M+H)$^+$.

EXAMPLE 101

Ethyl 3-[(2,4-difluorophenyl)amino]-6-oxo-7-(tetrahydro-2H-pyran-2-ylmethyl)-6,7-dihydrothieno[2,3-b]pyridine-2-carboxylate From Intermediate 62 and 2,4-difluoroaniline by the method of Example 1. δH (CDCl$_3$) 8.45 (1H, br s), 7.05-6.99 (1H, m), 6.95 (1H, d, J 9.7 Hz), 6.89-6.72 (2H, m), 6.21 (1H, d, J 9.7 Hz), 4.33-4.23 (2H, m), 4.21-4.13 (1H, m), 3.89-3.74 (3H, m), 3.31-3.22 (1H, m), 1.97-1.78 (2H, m), 1.68-1.39 (4H, m), 1.32 (3H, t, J 7.1 Hz). LCMS (ES$^+$) 449.0 (M+H)$^+$.

EXAMPLE 102

Ethyl 3-anilino-7-benzyl-6-oxo-6,7-dihydrothieno[2,3-b]pyridine-2-carboxylate

From Intermediate 63 and aniline by the method of Example 1. Pale yellow solid. δH (CDCl$_3$) 8.52 (1H, br s), 7.20-7.05 (7H, m), 6.98-6.88 (4H, m), 6.11 (1H, d, J 9.7 Hz), 5.11 (2H, s), 4.10 (2H, q, J 7.1 Hz), 1.15 (3H, t, J 7.1 Hz). LCMS (ES$^+$) 405 (M+H)$^+$.

EXAMPLE 103

3-Anilino-7-benzyl-6-oxo-6,7-dihydrothieno[2,3-b]pyridine-2-carboxamide

From Intermediate 64 by the method of Example 45. δH (DMSO-d6) 8.69 (1H, br s), 7.43 (2H, br s), 7.40-7.30 (6H, m), 7.25-7.20 (2H, m), 6.91-6.84 (3H, m), 6.45 (1H, d, J 9.6 Hz), 5.32 (2H, s). LCMS (ES*) 376 (M+H)$^+$.

EXAMPLE 104

3-Anilino-6-oxo-7-phenyl-6,7-dihydrothieno[2,3-b]pyridine-2-carbohydrazide

To a stirred solution of Example 1 (200 mg, 0.5 mmol) in ethoxyethanol (5 mL) was added hydrazine hydrate (1.5 mmol). The reaction mixture was heated to 120° C. for 6 h. Upon cooling the reaction mixture was poured into sat NaHCO$_3$ aq and extracted with DCM (×2). The combined organic fractions were dried (MgSO$_4$) and concentrated in vacuo. Purification by flash column chromatography (silica, 5% EtOH in DCM) gave the title compound (86 mg, 46%). δH (CDCl$_3$) 8.76 (1H, br s), 8.60 (1H, br s), 7.55-7.7 (3H, m), 7.4-7.5 (2H, m), 7.25-7.35 (3H, m), 6.9-7.0 (2H, m), 6.35 (1H, d, J 10 Hz), 4.3 (2H, br s). LCMS (ES$^+$) RT 2.84 minutes, 377 (M+H)$^+$.

EXAMPLE 105

Ethyl 3-anilino-7-[4-(dimethylamino)phenyl]-6-oxo-6,7-dihydrothieno[2,3-b]pyridine-2-carboxylate From Intermediate 65 and aniline by the method of Example 1. δH (CDCl$_3$) 8.69 (1H, br s), 7.26 (2H, t, J 8.0 Hz), 7.14 (2H, d, J 9.0 Hz), 7.10-7.05 (4H, m), 6.75 (2H, d, J 9.0 Hz), 6.26 (1H, d, J 9.7 Hz), 4.17 (2H, q, J 7.1 Hz), 2.96 (6H, s), 1.21 (3H, t, J 7.1 Hz). LCMS (ES$^+$) RT 4.31 minutes, 434 (M+H)$^+$.

EXAMPLE 106

3-Anilino-7-[4-(dimethylamino)phenyl]-N-methoxy-N-methyl-6-oxo-6,7-dihydrothieno[2,3-b]pyridine-2-carboxamide From Intermediate 66 and N,O-dimethylhydroxylamine hydrochloride by the method of Example 17. δH (CDCl$_3$) 9.92 (1H, br s), 7.26-7.13 (6H, m), 7.05-7.01 (2H, m), 6.75 (2H, d, J 8.8 Hz), 6.26 (1H, d, J 9.7 Hz), 3.57 (3H, s), 3.19 (3H, s), 2.97 (6H, s). LCMS (ES$^+$) RT 3.77 minutes, 449 (M+H)$^+$.

EXAMPLE 107

3-Anilino-7-[4-(dimethylamino)phenyl]-N-[3-(1H-imidazol-1-yl)propyl]-6-oxo-6,7-dihydrothieno[2,3-b]pyridine-2-carboxamide From Intermediate 66 and 1-(3-aminopropyl)imidazole by the method of Example 17. δH (CDCl$_3$) 8.52 (1H, brs), 7.35 (1H, s), 7.24 (1H, m), 7.21-7.12 (3H, m), 7.02-6.95 (4H, m), 6.81 (1H, s), 6.74 (2H, d, J 9.0 Hz), 6.31 (1H, d, J 9.6 Hz), 5.89 (1H, br t, J 6.0 Hz), 3.86 (2H, t, J 6.4 Hz), 3.23 (2H, q, J 6.3 Hz), 2.96 (6H, s), 1.93-1.89 (2H, m). LCMS (ES$^+$) RT 2.39 minutes, 513 (M+H)$^+$.

EXAMPLE 108

3-Anilino-7-[4-(dimethylamino)phenyl]-6-oxo-N-(2-piperidin-1-ylethyl)-6,7-dihydrothieno[2,3-b]pyridine-2-carboxamide From Intermediate 66 and 1-(2-aminoethyl)piperidine by the method of Example 17. δH (CDCl$_3$) 8.63 (1H, brs), 7.23-7.14 (5H, m), 6.97-6.94 (3H, m), 6.76-6.73 (2H, m), 6.43 (1H, br s), 6.31 (1H, d, J 9.7 Hz), 3.33 (2H, q, J 5.7 Hz), 2.96 (6H, s), 2.39 (2H, t, J 4.9 Hz), 2.35-2.22 (4H, m), 1.53-1.43 (4H, m), 1.29-1.28 (2H, m). LCMS (ES$^+$) RT 2.44 minutes, 516 (M+H)$^+$.

EXAMPLE 109

3-Anilino-N,N-dimethyl-6-oxo-7-phenyl-6,7-dihydrothieno[2,3-b]pyridine-2-carboxamide From Example 14 and dimethylamine hydrochloride by the method of Example 17. δH (CDCl$_3$) 8.45 (1H, br), 7.55-7.46 (3H, m), 7.36-7.30 (3H, m), 7.23-7.18 (2H, m), 6.95-6.92 (3H, m), 6.36 (1H, d, J 9.7 Hz), 2.98 (6H, s). LCMS (ES$^+$) RT 3.18 minutes, 390 (M+H)$^+$.

EXAMPLE 110

3-Anilino-N,N-diethyl-6-oxo-7-phenyl-6,7-dihydrothieno[2,3-b]pyridine-2-carboxamide From Example 14 and diethylamine by the method of Example 17. δH (CDCl$_3$) 7.55-7.45 (3H, m), 7.37-7.30 (3H, m), 7.23-7.18 (2H, m), 6.94-6.91 (3H, m), 6.37 (1H, d, J 9.7 Hz), 3.38 (4H, q, J 7.1 Hz), 1.05 (6H, t, J 7.1 Hz). LCMS (ES$^+$) RT 3.49 minutes, 418 (M+H)$^+$.

EXAMPLE 111

3-Anilino-N-methoxy-N-methyl-6-oxo-7-phenyl-6,7-dihydrothieno[2,3-b]pyridine-2-carboxamide From Example 14 and N,O-dimethylhydroxylamine hydrochloride by the method of Example 17. δH (CDCl$_3$) 9.93 (1H, br s), 7.54-7.44 (3H, m), 7.35-7.32 (2H, m), 7.27-7.23 (2H, m), 7.16 (1H, d, J 9.7 Hz), 7.07-7.02 (3H, m), 6.27 (1H, d, J 9.7 Hz), 3.54 (3H, s), 3.19 (3H, s). LCMS (ES$^+$) RT 3.64 minutes, 376 (M+H)$^+$.

EXAMPLE 112

3-Anilino-N-[3-(4-methylpiperazin-1-yl)propyl]-6-oxo-7-phenyl-6,7-dihydrothieno[2,3-b]pyridine-2-carboxamide From Example 14 and 1-(3-aminopropyl)-4-methylpiperazine by the method of Example 17. δH (CDCl$_3$) 9.21 (1H, br s), 7.55-7.45 (3H, m), 7.38-7.30 (2H, m), 7.27-7.17 (3H, m), 7.01-6.98 (3H, m), 6.33 (1H, d, J 9.7 Hz), 3.39-3.35 (2H, m), 2.50-2.05 (10H, m), 2.07 (3H, s), 1.64-1.60 (2H, m). LCMS (ES*) RT 2.26 minutes, 502 (M+H)$^+$.

EXAMPLE 113

3-Anilino-N-[3-(1H-imidazol-1-yl)propyl]-6-oxo-7-phenyl-6,7-dihydrothieno[2,3-b]pyridine-2-carboxamide From Example 14 and 1-(3-aminopropyl)imidazole by the method of Example 17. δH (CDCl$_3$) 8.51 (1H, br s), 7.56-7.39 (3H, m), 7.34-7.30 (3H, m), 7.26-7.18 (3H, m), 7.02-6.96 (3H, m), 6.92 (1H, s), 6.80 (1H, s), 6.31 (1H, d, J 9.7 Hz), 6.14 (1H, m), 3.85 (2H, t, J 6.8 Hz), 3.22 (2H, q, J 6.3 Hz), 1.90 (2H, m). LCMS (ES$^+$) RT 2.36 minutes, 470 (M+H)$^+$.

EXAMPLE 114

3-Anilino-N-[2-(diethylamino)ethyl]-6-oxo-7-phenyl-6,7-dihydrothieno[2,3-b]pyridine-2-carboxamide From Example 14 and N,N-diethylethylenediamine by the method of Example 17. δH (CDCl$_3$) 8.72 (1H, br s), 7.56-7.47 (3H, m), 7.36-7.33 (2H, m), 7.25-7.19 (3H, m), 7.01-6.94 (3H, m), 6.33 (1H, d, J 9.7 Hz), 6.42-6.28 (1H, br s), 3.31-3.27 (2H, m), 2.50-2.40 (6H, m), 0.88 (6H, t, J 7.1 Hz). LCMS (ES$^+$) RT 2.40 minutes, 461 (M+H)$^+$.

EXAMPLE 115

3-Anilino-N-[2-(diethylamino)ethyl]-N-methyl-6-oxo-7-phenyl-6,7-dihydrothieno[2,3-b]pyridine-2-carboxamide From Example 14 and N,N-diethyl-N'-methylethylenediamine by the method of Example 17. δH (CDCl$_3$) 8.35 (1H, br s), 7.47-7.38 (3H, m), 7.29-7.25 (2H, m), 7.20 (1H, d, J 9.7 Hz), 7.15-7.12 (2H, m), 6.88-6.85 (3H, m), 6.28 (1H, d, J 9.7 Hz), 3.38 (2H, t, J 7.0 Hz), 2.92 (3H, s), 2.44 (2H, t, J 7.0 Hz), 2.39-2.33 (4H, m), 0.81 (6H, m). LCMS (ES$^+$) RT 2.35 minutes, 475 (M+H)$^+$.

EXAMPLE 116

3-Anilino-N-methyl-6-oxo-7-phenyl-6,7-dihydrothieno[2,3-b]pyridine-2-carboxamide From Example 14 and methylamine by the method of Example 17. δH (CDCl$_3$) 8.73 (1H, br s), 7.54-7.45 (3H, m), 7.35-7.31 (2H, m), 7.26-7.18 (3H, m), 7.03-6.97 (3H, m), 6.31 (1H, d, J 9.7 Hz), 5.57-5.54 (1H, br m), 2.78 (3H, d, J 4.8 Hz). LCMS (ES$^+$) RT 3.22 minutes, 376 (M+H)$^+$.

EXAMPLE 117

3-Anilino-N-ethyl-6-oxo-7-phenyl-6,7-dihydrothieno[2,3-b]pyridine-2-carboxamide

From Example 14 and ethylamine by the method of Example 17. δH (CDCl$_3$) 8.84 (1H, brs), 7.56-7.47 (3H, m), 7.36-7.33 (2H, m), 7.26-7.19 (3H, m), 7.02-6.99 (3H, m), 6.33 (1H, d, J 9.7 Hz), 5.40 (1H, m), 3.28 (2H, m), 1.07 (3H, t, J 7.3 Hz). LCMS (ES$^+$) RT 3.39 minutes, 390 (M+H)$^+$.

EXAMPLE 118

3-Anilino-N-(2-morpholin-4-ylethyl)-6-oxo-7-phenyl-6,7-dihydrothieno[2,3-b]pyridine-2-carboxamide From Example 14 and 4-(2-aminoethyl)morpholine by the method of Example 17. δH (CDCl$_3$) 8.47 (1H, br s), 7.58-7.49 (3H, m), 7.37-7.35 (2H, m), 7.25-7.17 (3H, m), 7.01-6.91 (3H, m), 6.35 (1H, d, J 9.7 Hz), 6.37-6.33 (1H, br m), 3.55-3.53 (4H, m), 3.37-3.34 (2H, m), 2.43-2.41 (2H, m), 2.35-2.33 (4H, m). LCMS (ES$^+$) RT 2.34 minutes, 475 (M+H)$^+$.

EXAMPLE 119

3-Anilino-N-[2-(dimethylamino)ethyl]-N-methyl-6-oxo-7-phenyl-6,7-dihydrothieno[2,3-b]pyridine-2-carboxamide From Example 14 and N,N-dimethyl-N'-methylethylenediamine by the method of Example 17. δH (CDCl$_3$) 8.32 (1H, br s), 7.55-7.48 (3H, m), 7.37-7.34 (2H, m), 7.26 (1H, d, J 9.7 Hz), 7.25-7.18 (2H, m), 6.96-6.92 (3H, m), 6.36 (1H, d, J 9.7 Hz), 3.52 (2H, t, J 6.7 Hz), 2.97 (3H, s), 2.41 (2H, t, J 6.7 Hz), 2.19 (6H, s). LCMS (ES$^+$) RT 2.27 minutes, 447 (M+H)$^+$.

EXAMPLE 120

3-Anilino-N-(3-morpholin-4-ylpropyl)-6-oxo-7-phenyl-6,7-dihydrothieno[2,3-b]pyridine-2-carboxamide From Example 14 and 4-(3-aminopropyl)morpholine by the method of Example 17. δH (CDCl$_3$) 9.30 (1H, brs), 7.72 (1H, brs), 7.65-7.56 (3H, m), 7.46-7.43 (2H, m), 7.35-7.28 (3H, m), 7.11-7.08 (3H, m), 6.42 (1H, d, J 9.7 Hz), 3.51-3.44 (6H, m), 2.52-2.44 (6H, m), 1.74-1.68 (2H, m). LCMS (ES$^+$) RT 2.33 minutes, 489 (M+H)$^+$.

EXAMPLE 121

3-[(2,4-Difluorophenyl)amino]-N-methoxy-N-methyl-6-oxo-7-phenyl-6,7-dihydrothieno[2,3-b]pyridine-2-carboxamide From Intermediate 67 and N,O-dimethylhydroxylamine hydrochloride by the method of Example 17. δH (CDCl$_3$) 9.90 (1H, br s), 7.73-7.63 (3H, m), 7.51-7.47 (2H, m), 7.25-7.19 (2H, m), 7.06-6.90 (2H, m), 6.46 (1H, d, J 9.7 Hz), 3.70 (3H, s), 3.36 (3H, s). LCMS (ES$^+$) RT 3.67 minutes, 442 (M+H)$^+$.

EXAMPLE 122

3-[(2,4-Difluorophenyl)amino]-6-oxo-7-phenyl-N-(2-piperidin-1-ylethyl)-6,7-dihydrothieno[2,3-b]pyridine-2-carboxamide From Intermediate 67 and 1-(2-aminoethyl)piperidine by the method of Example 17. δH (CDCl$_3$) 8.40 (1H, s), 7.43-7.58 (3H, m), 7.32-7.37 (2H, m), 7.13 (1H, d, J 9.7 Hz), 6.82-6.98 (2H, m), 6.74 (1H, tq, J 1.5, 7.9 Hz), 6.55 (1H, s), 6.37 (1H, d, J 9.7 Hz), 3.34 (2H, q, J 5.8 Hz), 2.22-2.44 (6H, m), 1.32-1.48 (6H, m). LCMS (ES$^+$) RT 2.42 minutes, 509 (M+H)$^+$.

EXAMPLE 123

3-Anilino-N-(2-hydroxy-1,1-dimethylethyl)-6-oxo-7-phenyl-6,7-dihydrothieno[2,3-b]pyridine-2-carboxamide A mixture of Example 1 and 2-amino-2-methyl-1-propanol (1.22 mL, 13 mmol) was heated at 150° C. for 16 h. The mixture was partitioned between DCM (60 mL) and 10% citric acid (75 mL). The aqueous phase was extracted with DCM (20 mL). The combined organics were dried (Na$_2$SO$_4$)

and concentrated in vacuo. Purification by column chromatography (silica, 40% EtOAc in DCM) gave the title compound as a pale brown solid (45 mg, 16%). δH (CDCl₃) 8.44 (1H, br s), 7.56-7.46 (3H, m), 7.34-7.31 (2H, m), 7.26-7.20 (3H, m), 7.03-6.96 (3H, m), 6.33 (1H, d, J 9.7 Hz), 5.65 (1H, br s), 4.21-4.18 (1H, br m), 3.49 (2H, d, J 5.5 Hz), 1.18 (6H, s). LCMS (ES⁺) 434 (M+H)⁺.

EXAMPLE 124

Ethyl 3-[(3-chloro-2-cyanophenyl)amino]-6-oxo-7-phenyl-6,7-dihydrothieno[2,3-b]pyridine-2-carboxylate From Intermediate 5 and 2-amino-6-chlorobenzonitrile by the method of Example 1. δH (DMSO-d6) 8.96 (1H, br s), 7.63-7.53 (4H, m), 7.45-7.29 (3H, m), 7.15 (1H, d, J 9.6 Hz), 6.90 (1H, d, J 8.3 Hz), 6.44 (1H, d, J 9.6 Hz), 4.01 (2H, q, J 7.1 Hz), 1.0 (3H, t, J 7.1 Hz). LCMS (ES⁺) RT 3.916 minutes, 450.0 (M+H)⁺.

EXAMPLE 125

Ethyl 3-[(2-cyano-3-methylphenyl)amino]-6-oxo-7-phenyl-6,7-dihydrothieno[2,3-b]pyridine-2-carboxylate From Intermediate 5 and 2-amino-6-methylbenzonitrile by the method of Example 1. δH (DMSO-d6) 8.91 (1H, s), 7.74-7.48 (7H, m), 7.16 (1H, d, J 7.6 Hz), 7.03 (1H, d, J 8.2 Hz), 6.53 (1H, d, J 9.7 Hz), 4.20 (2H, q, J 7.1 Hz), 2.57 (3H, s), 1.20 (3H, t, J 7.1 Hz). LCMS (ES⁺) RT 3.888 minutes, 430.0 (M+H)⁺.

EXAMPLE 126

Ethyl 3-[(2-cyano-5-methylphenyl)amino]-6-oxo-7-phenyl-6,7-dihydrothieno[2,3-b]pyridine-2-carboxylate From Intermediate 5 and 2-amino-4-methylbenzonitrile by the method of Example 1. δH (DMSO-d6) 9.06 (1H, s), 7.86-7.78 (4H, m), 7.72-7.69 (2H, m), 7.63 (1H, d, J 9.7 Hz), 7.20-7.17 (2H, m), 6.66 (1H, d, J 9.7 Hz), 4.32 (2H, q, J 7.1 Hz), 2.47 (3H, s), 1.31 (3H, t, J 7.1 Hz). LCMS (ES⁺) RT 3.914 minutes, 430.0 (M+H)⁺.

EXAMPLE 127

Ethyl 3-[(4-fluorophenyl)amino]-6-oxo-7-phenyl-6,7-dihydrothieno[2,3-b]pyridine-2-carboxylate From Intermediate 5 and 4-fluoroaniline by the method of Example 1. Off-white solid. δH (DMSO-d6) 8.68 (1H, s), 7.46-7.58 (3H, m), 7.37-7.43 (2H, m), 7.05-7.12 (5H, m), 6.30 (1H, d, J 9.7 Hz), 4.05 (2H, q, J 7.1 Hz), 1.06 (3H, t, J 7.1 Hz). LCMS (ES⁺) RT 3.98 minutes, 409 (M+H)⁺.

EXAMPLE 128

Ethyl 3-[(4-fluorophenyl)amino]-6-oxo-7-phenyl-6,7-dihydrothieno[2,3-b]pyridine-2-carboxylate From Intermediate 5 and 4-amino-2-chlorobenzonitrile by the method of Example 1. Pale orange solid. δH (CDCl₃) 8.53 (1H, br s), 7.58-7.49 (4H, m), 7.37-7.34 (2H, m), 7.30 (1H, d, J 9.7 Hz), 7.04 (1H, d, J 2.3 Hz), 6.89 (1H, dd, J 8.6, 2.3 Hz), 6.48 (1H, d, J 9.7 Hz), 4.20 (2H, q, J 7.1 Hz), 1.22 (3H, t, J 7.1 Hz). LCMS (ES⁺) RT 3.77 minutes, 450 (M+H)⁺.

EXAMPLE 129

Ethyl 3-[(3-chloro-4-fluorophenyl)amino]-6-oxo-7-phenyl-6,7-dihydrothieno[2,3-b]pyridine-2-carboxylate From Intermediate 5 and 3-chloro-4-fluoroaniline by the method of Example 1. δH (CDCl₃) 8.70 (1H, s), 7.67-7.59 (3H, m), 7.44-7.41 (2H, m), 7.24-7.02 (4H, m), 6.43 (1H, d, J 9.8 Hz), 4.28 (2H, q, J 7.1 Hz), 1.31 (3H, t, J 7.1 Hz). LCMS (ES⁺) RT 4.245 minutes, 443 (M+H)⁺.

EXAMPLE 130

Ethyl 3-[(2-cyanophenyl)amino]-7-(4-fluorophenyl)-6-oxo-6,7-dihydrothieno[2,3-b]pyridine-2-carboxylate From Intermediate 68 and anthranilonitrile by the method of Example 1. δH (CDCl₃) 8.77 (1H, br s), 7.62 (1H, d, J 7.6 Hz), 7.47 (1H, t, J 6.6 Hz), 7.40-7.37 (2H, m), 7.28-7.21 (3H, m), 7.13-7.07 (2H, m), 6.42 (1H, d, J 9.7 Hz), 4.29 (2H, q, J 7.0 Hz), 1.28 (3H, t, J 7.0 Hz). LCMS (ES⁺) RT 3.770 minutes, 433.9 (M+H)⁺.

EXAMPLE 131

Ethyl 3-[(2-cyano-3-methylphenyl)amino]-7-(4-fluorophenyl)-6-oxo-6,7-dihydrothieno[2,3-b]pyridine-2-carboxylate From Intermediate 68 and 2-amino-6-methylbenzonitrile by the method of Example 1. Light yellow solid. δH (CDCl₃) 8.76 (1H, br s), 7.40-7.19 (6H, m), 6.97 (1H, d, J 7.6 Hz), 6.89 (1H, d, J 8.2 Hz), 6.4 (1H, d, J 9.7 Hz), 4.26 (2H, q, J 7.0 Hz), 2.54 (3H, s), 1.28 (3H, t, J 7.0 Hz). LCMS (ES⁺) RT 3.937 minutes, 448.0 (M+H)⁺.

EXAMPLE 132

Ethyl 3-[(4-fluoro-3-methylphenyl)amino]-7-(4-fluorophenyl)-6-oxo-6,7-dihydrothieno[2,3-b]pyridine-2-carboxylate From Intermediate 68 and 4-fluoro-3-methylaniline by the method of Example 1. Light yellow solid. δH (CDCl₃) 8.78 (1H, br s), 7.38-7.35 (2H, m), 7.28-7.24 (2H, m), 7.04-6.96 (4H, m), 6.3 (1H, d, J 9.8 Hz), 4.24 (2H, q, J 7.1 Hz), 2.25 (3H, s), 1.28 (3H, t, J 7.1 Hz). LCMS (ES⁺) RT 4.298 minutes, 441.0 (M+H)⁺.

EXAMPLE 133

Ethyl 3-[(4-fluoro-3-methylphenyl)amino]-7-(4-chlorophenyl)-6-oxo-6,7-dihydrothieno[2,3-b]pyridine-2-carboxylate From Intermediate 69 and 4-fluoro-3-methylaniline by the method of Example 1. δH (CDCl₃) 8.72 (1H, br s), 7.58-7.38 (2H, m), 7.35-7.28 (2H, m), 6.99-6.98 (4H, m), 6.34 (1H, d, J 9.8 Hz), 4.28 (2H, q, J 7.1 Hz), 2.29 (3H, s), 1.32 (3H, t, J 7.1 Hz). LCMS (ES⁺) RT 4.57 minutes, 457 (M+H)⁺.

EXAMPLE 134

Ethyl 3-[(4-fluoro-3-methylphenyl)amino]-7-(3-methylphenyl)-6-oxo-6,7-dihydrothieno[2,3-b]pyridine-2-carboxylate From Intermediate 70 and 4-fluoro-3-methylaniline by the method of Example 1. δH (CDCl$_3$) 8.63 (1H, br s), 7.4-7.15 (1H, m), 7.30-7.27 (1H, m), 7.18-7.10 (2H, m), 7.04-6.90 (4H, m), 6.27 (1H, d, J 9.7 Hz), 4.18 (2H, q, J 7.1 Hz), 2.21 (3H, s), 2.20 (3H, s), 1.21 (3H, t, J 7.1 Hz). LCMS (ES$^+$) RT 4.469 minutes, 437 (M+H)$^+$.

EXAMPLE 135

Ethyl 3-[(3-methylphenyl)amino]-7-(3-methylphenyl)-6-oxo-6,7-dihydrothieno[2,3-b]pyridine-2-carboxylate From Intermediate 70 and 3-methylaniline by the method of Example 1. δH (CDCl$_3$) 8.55 (1H, br s), 7.32-7.28 (1H, m), 7.27-7.17 (1H, m), 7.08-7.00 (4H, m), 7.88-7.75 (3H, m), 6.15 (1H, d, J 9.8 Hz), 4.08 (2H, q, J 7.1 Hz), 2.27 (3H, s), 2.17 (3H, s), 1.12 (3H, t, J 7.1 Hz). LCMS (ES$^+$) RT 4.543 minutes, 419 (M+H)$^+$.

EXAMPLE 136

3-[(2,4-Difluorophenyl)amino]-6-oxo-7-phenyl-6,7-dihydrothieno[2,3-b]pyridine-2-carbonitrile From Intermediate 9 and 2,4-difluoroaniline by the method of Example 1. Off-white solid. δH (DMSO-d6) 9.34 (1H, s), 8.20 (1H, d, J 9.6 Hz), 7.42-7.72 (7H, m), 7.19 (1H, dq, J 1.1, 9.6 Hz), 6.70 (1H, d, J 9.6 Hz). LCMS (ES$^+$) RT 3.43 minutes, 380 (M+H)$^+$.

EXAMPLE 137

3-[(3-Chloro-4-fluorophenyl)amino]-6-oxo-7-phenyl-6,7-dihydrothieno[2,3-b]pyridine-2-carbonitrile From Intermediate 9 and 3-chloro-4-fluoroaniline by the method of Example 1. δH (DMSO-d6) 9.30 (1H, br s), 7.87 (1H, d, J 9.7 Hz), 7.55-7.48 (3H, m), 7.42-7.38 (2H, m), 7.31-7.23 (2H, m), 7.09-7.00 (1H, m), 6.51 (1H, d, J 9.7 Hz). LCMS (ES$^+$) RT 3.578 minutes, 396 (M+H)$^+$.

EXAMPLE 138

3-[(2-Methylphenyl)amino]-6-oxo-7-phenyl-6,7-dihydrothieno[2,3-b]pyridine-2-carbonitrile From Intermediate 9 and 2-methylaniline by the method of Example 1. Orange solid. δH (DMSO-d6) 8.9 (1H, s), 8.08 (1H, d, J 9.6 Hz), 7.6-7.4 (5H, m), 7.26 (1H, s), 7.25-7.15 (3H, m), 6.6 (1H, d, J 9.6 Hz), 2.2 (3H, s). LCMS (ES$^+$) RT 3.46 minutes, 358 (M+H)$^+$.

EXAMPLE 139

3-[(3-Methylphenyl)amino]-6-oxo-7-phenyl-6,7-dihydrothieno[2,3-b]pyridine-2-carbonitrile From Intermediate 9 and 3-methylaniline by the method of Example 1. Orange solid. δH (DMSO-d6) 9.2 (1H, s), 8.0 (1H, d, J 9.6 Hz), 7.6-7.5 (5H, m), 7.2 (3H, m), 6.9 (1H, m), 6.6 (1H, d, J 9.6 Hz), 2.2 (3H, s). LCMS (ES$^+$) RT 3.54 minutes, 358 (M+H)$^+$.

EXAMPLE 140

3-[(3,5-Dichlorophenyl)amino]-6-oxo-7-phenyl-6,7-dihydrothieno[2,3-b]pyridine-2-carbonitrile From Intermediate 9 and 3,5-dichloroaniline by the method of Example 1. Off-white solid. δH (DMSO-d6) 9.3 (1H, s), 7.65 (1H, d, J 9.6 Hz), 7.4-7.3 (5H, m), 6.9 (1H, s), 6.8 (2H, s), 6.4 (1H, d, J 9.6 Hz). LCMS (ES$^+$) RT 3.63 minutes, 412 (M+H)$^+$.

EXAMPLE 141

3-[(3-Nitrophenyl)amino]-6-oxo-7-phenyl-6,7-dihydrothieno[2,3-b]pyridine-2-carbonitrile From Intermediate 9 and 3-nitroaniline by the method of Example 1. Yellow solid. δH (DMSO-d6) 9.8 (1H, s), 8.0 (1H, d, J 9.6 Hz), 7.9-7.5 (9H, m), 6.6 (1H, d, J 9.6 Hz). LCMS (ES$^+$) RT 3.42 minutes, 389 (M+H)$^+$.

EXAMPLE 142

6-Oxo-7-phenyl-3-{[2-(trifluoromethoxy)phenyl]amino}-6,7-dihydrothieno[2,3-b]pyridine-2-carbonitrile From Intermediate 9 and 2-(trifluoromethoxy)aniline by the method of Example 1. δH (DMSO-d6) 9.31 (1H, s), 8.10 (1H, d, J 9.7 Hz), 7.7-7.3 (9H, m), 6.69 (1H, d, J 9.7 Hz). LCMS (ES$^+$) RT 3.676 minutes, 427.8 (M+H)$^+$.

EXAMPLE 143

3-[(2,6-Dichlorophenyl)amino]-6-oxo-7-phenyl-6,7-dihydrothieno[2,3-b]pyridine-2-carbonitrile From Intermediate 9 and 2,6-dichloroaniline by the method of Example 1. δH (DMSO-d6) 9.60 (1H, s), 8.32 (1H, d, J 9.7 Hz), 7.71-7.46 (8H, m), 6.73 (1H, d, J 9.7 Hz). LCMS (ES$^+$) RT 3.454 minutes, 411.8 (M+H)$^+$.

EXAMPLE 144

3-{[2-(Difluoromethoxy)phenyl]amino}-6-oxo-7-phenyl-6,7-dihydrothieno[2,3-b]pyridine-2-carbonitrile From Intermediate 9 and 2-(difluoromethoxy)aniline by the method of Example 1. δH (DMSO-d6) 9.15 (1H, s), 8.13 (1H, d, J 9.7 Hz), 7.70-7.04 (10H, m), 6.66 (1H, d, J 9.7 Hz). LCMS (ES$^+$) RT 3.425 minutes, 409.8 (M+H)$^+$.

EXAMPLE 145

3-[(2,6-Difluorophenyl)amino]-6-oxo-7-phenyl-6,7-dihydrothieno[2,3-b]pyridine-2-carbonitrile From Intermediate 9 and 2,6-difluoroaniline by the method of Example 1. δH (DMSO-d6) 8.43 (1H, s), 8.10 (1H, d, J 9.7 Hz), 7.54-7.42 (5H, m), 7.31 (1H, m), 7.12 (2H, t, J 8.0 Hz), 6.55 (1H, d, J 9.7 Hz). LCMS (ES$^+$) RT 3.300 minutes, 380.0 (M+H)$^+$.

EXAMPLE 146

3-[(4-Fluoro-2-methylphenyl)amino]-6-oxo-7-phenyl-6,7-dihydrothieno[2,3-b]pyridine-2-carbonitrile From Intermediate 9 and 2-methyl-4-fluoroaniline by the method of Example 1. δH (DMSO-d6) 8.99 (1H, s), 8.08 (1H, d, J 9.7 Hz), 7.58-7.43 (5H, m), 7.23 (1H, dd, J 5.5, 8.7 Hz), 7.11 (1H, dd, J 2.9, 9.7 Hz), 7.00 (1H, dt, J 2.9, 8.6 Hz), 6.56 (1H, d, J 9.7 Hz), 2.18 (3H, s). LCMS (ES$^+$) RT 3.422 minutes, 376.0 (M+H)$^+$.

EXAMPLE 147

6-Oxo-7-phenyl-3-({3-[(trifluoromethyl)thio]phenyl}amino)-6,7-dihydrothieno[2,3-b]pyridine-2-carbonitrile From Intermediate 9 and 3-trifluoromethylthioaniline by the method of Example 1. δH (DMSO-d6) 9.62 (1H, s), 8.00 (1H, d, J 9.7 Hz), 7.74-7.65 (3H, m), 7.60 (2H, dt, J 1.7, 6.5 Hz), 7.55 (1H, t, J 7.9 Hz), 7.48 (1H, t, J 1.7 Hz), 7.40 (2H, dt, J 2.4, 7.9 Hz), 6.68 (1H, d, J 9.7 Hz). LCMS (ES$^+$) RT 3.786 minutes, 444.0 (M+H)$^+$.

EXAMPLE 148

3-[(3-Bromo-4-methylphenyl)amino]-6-oxo-7-phenyl-6,7-dihydrothieno[2,3-b]pyridine-2-carbonitrile From Intermediate 9 and 3-bromo-4-methylaniline by the method of Example 1. δH (DMSO-d6) 9.31 (1H, s), 7.91 (1H, dd, J 2.1, 9.7 Hz), 7.61-7.52 (3H, m), 7.46 (2H, m), 7.29 (1H, d, J 2.1 Hz), 7.24 (1H, d, J 8.3 Hz), 7.03 (1H, dd, J 2.1, 8.2 Hz), 6.56 (1H, d, J 9.7 Hz), 2.25 (3H, s). LCMS (ES$^+$) RT 3.722 minutes, 438.0 (M+H)$^+$.

EXAMPLE 149

3-[(3-Bromo-2-methylphenyl)amino]-6-oxo-7-phenyl-6,7-dihydrothieno[2,3-b]pyridine-2-carbonitrile From Intermediate 9 and 3-bromo-2-methylaniline by the method of Example 1. δH (DMSO-d6) 9.15 (1H, s), 8.04 (1H, d, J 9.7 Hz), 7.68-7.50 (3H, m), 7.47-7.44 (3H, m), 7.20 (1H, dd, J 0.9, 7.9 Hz), 7.11 (1H, t, J 7.9 Hz), 6.56 (1H, d, J 9.7 Hz), 2.26 (3H, s). LCMS (ES$^+$) RT 3.63 minutes, 437.9 (M+H)$^+$.

EXAMPLE 150

6-oxo-7-phenyl-3-{[3-(trifluoromethoxy)phenyl]amino}-6,7-dihydrothieno[2,3-b]pyridine-2-carbonitrile From Intermediate 9 and 3-trifluoromethoxyaniline by the method of Example 1. δH (DMSO-d6) 9.60 (1H, s), 8.00 (1H, d, J 9.7 Hz), 7.81-8.65 (3H, m), 7.61-7.59 (2H, m), 7.50 (1H, t, J 8.2 Hz), 7.20 (1H, dd, J 1.5, 8.2 Hz), 7.12 (1H, s), 7.04 (1H, d, J 8.2 Hz), 6.68 (1H, d, J 9.7 Hz). LCMS (ES$^+$) RT 3.654 minutes, 428.0 (M+H)$^+$.

EXAMPLE 151

3-{[3-(Methylthio)phenyl]amino}-6-oxo-7-phenyl-6,7-dihydrothieno[2,3-b]pyridine-2-carbonitrile From Intermediate 9 and 3-(methylthio)aniline by the method of Example 1. δH (DMSO-d6) 9.24 (1H, s), 7.87 (1H, d, J 9.7 Hz), 7.62-7.46 (3H, m), 7.42-7.39 (2H, m), 7.14 (1H, t, J 7.9 Hz), 6.90 (1H, t, J 1.9 Hz), 6.82-6.79 (2H, m), 6.49 (1H, d, J 9.7 Hz), 2.37 (3H, s). LCMS (ES$^+$) RT 3.504 minutes, 389.9 (M+H)$^+$.

EXAMPLE 152

3-[(4-Fluoro-3-methylphenyl)amino]-6-oxo-7-phenyl-6,7-dihydrothieno[2,3-b]pyridine-2-carbonitrile From Intermediate 9 and 4-fluoro-3-methylaniline by the method of Example 1. δH (DMSO-d6) 9.33 (1H, s), 8.10 (1H, d, J 9.7 Hz), 7.77-7.64 (3H, m), 7.59-7.56 (2H, m), 7.20-7.09 (3H, m), 6.68 (1H, d, J 9.7 Hz), 2.28 (3H, s). LCMS (ES$^+$) RT 3.509 minutes, 376.0 (M+H)$^+$.

EXAMPLE 153

3-[(3-Ethylphenyl)amino]-6-oxo-7-phenyl-6,7-dihydrothieno[2,3-b]pyridine-2-carbonitrile From Intermediate 9 and 3-ethylaniline by the method of Example 1. δH (CDCl$_3$) 7.48-7.57 (3H, m), 7.30-7.37 (2H, m), 7.25 (1H, d, J 9.7 Hz), 7.18 (1H, t, J 6.6 Hz), 6.93 (1H, d, J 7.7 Hz), 6.80-6.88 (2H, m), 6.42 (1H, d, J 9.7 Hz), 6.38 (1H, s), 2.56 (2H, q, J 7.6 Hz), 1.16 (3H, t, J 7.6 Hz). LCMS (ES$^+$) RT 3.69 minutes, 372 (M+H)$^+$.

EXAMPLE 154

7-(4-Fluorophenyl)-3-[(3-methylphenyl)amino]-6-oxo-6,7-dihydrothieno[2,3-b]pyridine-2-carbonitrile From Intermediate 72 and m-toluidine by the method of Example 1. δH (CDCl$_3$) 7.42-7.18 (6H, m), 6.94 (1H, d, J 7.53 Hz), 6.86-6.83 (2H, m), 6.76 (1H, s), 6.46 (1H, d, J 9.2 Hz), 2.32 (3H, s). LCMS (ES$^+$) RT 3.547 minutes, 375.9 (M+H)$^+$.

EXAMPLE 155

3-[(2,4-difluorophenyl)amino]-7-(4-methoxyphenyl)-6-oxo-6,7-dihydrothieno[2,3-b]pyridine-2-carbonitrile From Intermediate 73 and 2,4-difluoroaniline by the method of Example 1. δH (DMSO-d6) 9.46 (1H, br s), 8.28 (1H, d, J 7.7 Hz), 7.60-7.51 (4H, m), 7.33-7.25 (3H, m), 6.77 (1H, d, J 9.7 Hz), 4.00 (3H, s). LCMS (ES$^+$) RT 3.430 minutes, 410 (M+H)$^+$.

EXAMPLE 156

3-[(2,4-Difluorophenyl)amino]-7-(4-{[(2S)-2,3-dihydroxypropyl]oxy}phenyl)-6-oxo-6,7-dihydrothieno[2,3-b]pyridine-2-carbonitrile Prepared by the same route as Example 94 with (S)-(2,2-dimethyl-1,3-dioxolan-4-yl)methyl 4-methylbenzenesulfonate instead of the (R) enantiomer. δH (CDCl$_3$) 7.30 (1H, d, J 9.7 Hz), 7.25-7.23 (2H, m), 7.11-7.03 (3H, m), 6.92-6.82 (2H, m), 6.49 (1H, d, J 9.7 Hz), 6.10 (1H, s), 4.12-4.05 (3H, m), 3.81 (1H, dd, J 11.3, 3.7 Hz), 3.71 (1H, dd, J 11.3, 5.0 Hz). LCMS (ES$^+$) RT 2.864 minutes, 470 (M+H)$^+$.

EXAMPLE 157

7-(4-Acetylphenyl)-3-[(3-chlorophenyl)amino]-6-oxo-6,7-dihydrothieno[2,3-b]pyridine-2-carbonitrile From Intermediate 74 and 3-chloroaniline by the method of Example 1. δH (CDCl$_3$) 8.22 (2H, d, J 8.7 Hz), 7.57 (2H, d, J 8.7 Hz), 7.39 (1H, d, J 9.7 Hz), 7.31 (1H, t, J 8.0 Hz), 7.13 (1H, ddd, J 8.0, 1.9, 0.8 Hz), 7.05 (1H, t, J 2.1 Hz), 6.95 (1H, dd, J 7.9, 1.8 Hz), 6.57 (1H, d, J 9.8 Hz), 6.49 (1H, s), 2.71 (3H, s). LCMS (ES$^+$) RT 3.51 minutes, 442 (M+Na)$^+$.

EXAMPLE 158

7-(2-Chlorophenyl)-3-[(4-fluoro-3-methylphenyl)amino]-6-oxo-6,7-dihydrothieno[2,3-b]pyridine-2-carbonitrile From Intermediate 14 and 4-fluoro-3-methylaniline by the method of Example 1. Light yellow solid. δH (CDCl$_3$) 7.73-7.64 (1H, m), 7.60-7.38 (3H, m), 7.32-7.26 (1H, m), 7.07-6.88 (3H, m), 6.5 (1H, d, J 9.8 Hz), 6.30 (1H, s), 2.29 (3H, s). LCMS (ES$^+$) RT 3.619 minutes, 409.9 (M+H)$^+$.

EXAMPLE 159

7-(2-Chlorophenyl)-3-[(3-methylphenyl)amino]-6-oxo-6,7-dihydrothieno[2,3-b]pyridine-2-carbonitrile From Intermediate 14 and 3-methylaniline by the method of Example 1. Off-white solid. δH (CDCl$_3$) 7.73-7.64 (1H, m), 7.60-7.40 (3H, m), 7.32 (1H, d, J 9.8 Hz), 7.29-7.20 (1H, m), 7.05-6.85 (3H, m), 6.49 (1H, d, J 9.8 Hz), 6.40 (1H, s), 2.36 (3H, s). LCMS (ES$^+$) RT 3.565 minutes, 391.9 (M+H)$^+$.

EXAMPLE 160

3-[(2-hydroxyphenyl)amino]-6-oxo-7-phenyl-6,7-dihydrothieno[2,3-b]pyridine-2-carbonitrile From Intermediate 5 and 2-aminophenol by the method of Example 1. δH (DMSO-d6) 10.02 (1H, s), 8.65 (1H, s), 7.80-7.69 (3H, m), 7.15 (1H, dd, J 8.1, 2.0 Hz), 7.29-7.07 (4H, m), 6.93 (1H, t, J 7.3 Hz), 6.47 (1H, dd, J 9.8, 1.5 Hz), 4.30 (2H, q, J 7.1 Hz), 1.32 (3H, t, J 7.1 Hz).

EXAMPLE 161

3-[(3-hydroxyphenyl)amino]-6-oxo-7-phenyl-6,7-dihydrothieno[2,3-b]pyridine-2-carbonitrile From Intermediate 5 and 3-aminophenol by the method of Example 1. δH (DMSO-d6) 9.62 (1H, s), 8.81 (1H, s), 7.82-7.69 (3H, m), 7.68-7.63 (2H, m), 7.45 (1H, dd, J 2.2, 9.8 Hz), 7.27 (1H, t, J 8.0 Hz), 6.73-6.65 (3H, m), 6.59 (1H, dd, J 1.0, 9.7 HZ), 4.32 (2H, q, J 7.1 Hz), 1.33 (3H, t, J 7.1 Hz). LCMS (ES$^+$) RT 3.69 minutes, 377 (M+H)$^+$.

EXAMPLE 162

7-(4-Fluorophenyl)-3-[(3-methylphenyl)amino]-6-oxo-6,7-dihydrothieno[2,3-b]pyridine-2-carboxamide From Example 154 by the method of Example 22. Yellow solid. δH (CDCl$_3$) 8.7 (1H, br s), 7.32-7.29 (2H, m), 7.19-7.08 (4H, m), 6.84 (1H, d, J 7.5 Hz), 6.8-6.76 (2H, m), 6.26 (1H, d, J 9.7 Hz), 5.64 (2H, br s), 2.24 (3H, s). LCMS (ES$^+$) RT 3.163 minutes, 394 (M+H)$^+$.

EXAMPLE 163

3-[(2,4-Difluorophenyl)amino]-6-oxo-7-phenyl-6,7-dihydrothieno[2,3-b]pyridine-2-carboxamide From Example 136 by the method of Example 22. White solid. δH (DMSO-d6) 9.1 (1H, s), 7.6-7.26 (8H, m), 7.24 (1H, d, J 9.7 Hz), 7.18-7.0 (2H, m), 6.4 (1H, d, J 9.7 Hz). LCMS (ES$^+$) RT 3.091 minutes, 397 (M+H)$^+$.

EXAMPLE 164

6-Oxo-7-phenyl-3-{[3-(trifluoromethyl)phenyl]amino}-6,7-dihydrothieno[2,3-b]pyridine-2-carboxamide From Intermediate 71 by the method of Example 22. δH (DMSO-d6) 9.05 (1H, s), 7.59-7.75 (5H, m), 7.40-7.53 (4H, m), 7.23-7.31 (2H, m), 7.13 (1H, dd, J 1.8, 8.0 Hz), 6.54 (1H, d, J 9.7 Hz). LCMS (ES$^+$) RT 3.30 minutes, 430 (M+H)$^+$.

EXAMPLE 165

3-[(3,5-Dichlorophenyl)amino]-6-oxo-7-phenyl-6,7-dihydrothieno[2,3-b]pyridine-2-carboxamide From Example 140 by the method of Example 22. δH (DMSO-d6) 7.73-7.40 (8H, m), 7.05 (1H, t, J 1.8 Hz), 6.87 (2H, d, J 1.8 Hz), 6.57 (1H, d, J 9.6 Hz). LCMS (ES$^+$) RT 3.35 minutes, 430 (M+H)$^+$.

EXAMPLE 166

3-[(3-Bromophenyl)amino]-6-oxo-7-phenyl-6,7-dihydrothieno[2,3-b]pyridine-2-carboxamide From Example 19 by the method of Example 22. δH (DMSO-d6) 8.88 (1H, s), 7.72-7.35 (8H, m), 7.21 (1H, d, J 8.0 Hz), 7.12-7.05 (2H, m), 6.87 (1H, dd, J 1.5, 7.9 Hz), 6.51 (1H, d, J 9.7 Hz). LCMS (ES$^+$) RT 3.20 minutes, 440 (M+H)$^+$.

EXAMPLE 167

6-Oxo-7-phenyl-3-{[2-(trifluoromethoxy)phenyl]amino}-6,7-dihydrothieno[2,3-b]pyridine-2-carboxamide From Example 142 by the method of Example 22. δH (DMSO-d6) 8.99 (1H, s), 7.5-6.7 (12H, m), 6.26 (1H, d, J 9.7 Hz). LCMS (ES$^+$) RT 3.370 minutes, 445.8 (M+H)$^+$.

EXAMPLE 168

3-{[2-(Difluoromethoxy)phenyl]amino}-6-oxo-7-phenyl-6,7-dihydrothieno[2,3-b]pyridine-2-carboxamide From Example 144 by the method of Example 22. δH (DMSO-d6) 9.10 (1H, s), 8.06-7.31 (10H, m), 7.20 (1H, d, J 1.3, 7.7 Hz), 7.08 (1H, dt, J 1.5, 7.7 Hz), 6.96 (1H, dd, J 1.3, 8.0 Hz), 6.50 (1H, d, J 9.6 Hz). LCMS (ES$^+$) RT 3.151 minutes, 427.9 (M+H)$^+$.

EXAMPLE 169

3-[(2,6-Dichlorophenyl)amino]-6-oxo-7-phenyl-6,7-dihydrothieno[2,3-b]pyridine-2-carboxamide From Example 143 by the method of Example 22. δH (DMSO-d6) 10.02 (1H, s), 7.71-7.43 (8H, m), 7.30 (2H, br s), 6.67 (1H, d, J 9.8 Hz), 6.36 (1H, d, J 9.8 Hz). LCMS (ES$^+$) RT 3.23 minutes, 428.8 (M+H)$^+$.

EXAMPLE 170

3-[(3-Methylphenyl)amino]-6-oxo-7-phenyl-6,7-dihydrothieno[2,3-b]pyridine-2-carboxamide From Example 139 by the method of Example 22. δH (DMSO-d6) 8.92 (1H, s), 7.67-7.60 (3H, m), 7.55-7.50 (2H, m), 7.35-7.32 (3H, m), 7.15 (1H, t, J 7.7 Hz), 6.79-6.77 (2H, m), 6.73-6.71 (1H, m), 6.42 (1H, d, J 9.7 Hz), 2.26 (3H, s). LCMS (ES$^+$) RT 3.191 minutes, 375.9 (M+H)$^+$.

EXAMPLE 171

3-[(3-Bromo-4-methylphenyl)amino]-6-oxo-7-phenyl-6,7-dihydrothieno[2,3-b]pyridine-2-carboxamide From Example 148 by the method of Example 22. δH (DMSO-d6) 8.93 (1H, s), 7.72-7.54 (6H, m), 7.47-7.42 (2H, m), 7.35-7.08 (1H, m), 7.26-7.21 (1H, m), 6.89-6.86 (1H, m), 6.51 (1H, d, J 9.6 Hz), 2.55 (3H, s). LCMS (ES$^+$) RT 3.314 minutes, 456 (M+H)$^+$.

EXAMPLE 172

3-{[3-(Methylthio)phenyl]amino}-6-oxo-7-phenyl-6,7-dihydrothieno[2,3-b]pyridine-2-carboxamide From Example 151 by the method of Example 22. δH (DMSO-d6) 8.95 (1H, s), 7.76-7.59 (5H, m), 7.47-7.36 (3H, m), 7.24 (1H, t, J 7.9 Hz), 6.86 (2H, m), 6.70 (1H, dd, J 1.6, 7.8 Hz), 6.51 (1H, d, J 9.6 Hz), 2.55 (3H, s). LCMS (ES$^+$) RT 3.140 minutes, 408.0 (M+H)$^+$.

EXAMPLE 173

6-Oxo-7-phenyl-3-{[3-(trifluoromethoxy)phenyl]amino}-6,7-dihydrothleno[2,3-b]pyridine-2-carboxamide From Example 150 by the method of Example 22. δH (DMSO-d6) 8.88 (1H, s), 7.61-7.47 (5H, m), 7.38-7.25 (4H, m), 6.80-6.76 (3H, m), 6.40 (1H, d, J 9.6 Hz). LCMS (ES$^+$) RT 3.251 minutes, 445.9 (M+H)$^+$.

EXAMPLE 174

3-[(4-Fluoro-3-methylphenyl)amino]-6-oxo-7-phenyl-6,7-dihydrothieno[2,3-b]pyridine-2-carboxamide From Example 152 by the method of Example 22. δH (DMSO-d6) 9.05 (1H, s), 7.72-7.57 (5H, m), 7.38-7.31 (3H, m), 7.13-7.08 (1H, m), 6.99-6.96 (1H, m), 6.86-6.82 (1H, m), 6.46 (1H, d, J 9.6 Hz), 2.92 (3H, s). LCMS (ES$^+$) RT 3.317 minutes, 394.0 (M+H)$^+$.

EXAMPLE 175

6-Oxo-7-phenyl-3-({3-[(trifluoromethyl)thio]phenyl}amino)-6,7-dihydrothieno[2,3-b]pyridine-2-carboxamide From Example 147 by the method of Example 22. δH (DMSO-d6) 8.94 (1H, s), 7.61-7.53 (3H, m), 7.49-7.47 (2H, m), 7.35-7.25 (4H, m), 7.14-7.12 (2H, m), 7.01-6.99 (1H, m), 6.38 (1H, d, J 9.6 Hz). LCMS (ES$^+$) RT 3.368 minutes, 461.9 (M+H)$^+$.

EXAMPLE 176

3-[(3-Ethylphenyl)amino]-6-oxo-7-phenyl-6,7-dihydrothieno[2,3-b]pyridine-2-carboxamide From Example 153 by the method of Example 22. δH (DMSO-d6) 9.07 (1H, s), 7.56-7.76 (5H, m), 7.36-7.43 (3H, m), 7.23 (1H, t, J 7.7 Hz), 6.85-6.92 (2H, m), 6.80 (1H, d, J 1.7 Hz), 6.48 (1H, d, J 9.7 Hz), 2.61 (2H, q, J 7.6 Hz), 1.21 (3H, t, J 7.6 Hz). LCMS (ES$^+$) RT 3.27 minutes, 390 (M+H)$^+$.

EXAMPLE 177

7-(2-Chlorophenyl)-3-[(3-methylphenyl)amino]-6-oxo-6,7-dihydrothieno[2,3-b]pyridine-2-carboxamide From Example 159 by the method of Example 22. Yellow solid. δH (DMSO-d6) δH (CDCl$_3$) 8.95 (1H, s), 7.67-7.65 (1H, m), 7.56-7.50 (2H, m), 7.48-7.44 (1H, m), 7.24-7.20 (2H, m), 7.0-6.91 (3H, m), 6.38 (1H, d, J 9.8 Hz), 5.27 (2H, s), 2.34 (3H, s). LCMS (ES$^+$) RT 3.196 minutes, 410 (M+H)$^+$.

EXAMPLE 178

3-[(2-Cyano-3-methylphenyl)amino]-7-(4-fluorophenyl)-6-oxo-6,7-dihydrothieno[2,3-b]pyridine-2-carboxamide From Example 131 by the method of Example 38. White solid. δH (CDCl$_3$) 8.65 (1H, br s), 7.43-7.40 (2H, m), 7.39-7.25 (4H, m), 6.97 (1H, d, J 7.6 Hz), 6.70 (1H, d, J 8.2 Hz), 6.48 (1H, d, J 9.7 Hz), 5.55 (1H, br s), 2.57 (3H, s). LCMS (ES$^+$) RT 3.079 minutes, 418.9 (M+H)$^+$.

EXAMPLE 179

3-[(4-Fluoro-3-methylphenyl)amino]-7-(4-fluorophenyl)-6-oxo-6,7-dihydrothieno[2,3-b]pyridine-2-carboxamide From Example 132 by the method of Example 38. White solid. δH (CDCl$_3$) 9.1 (1H, br s), 7.4-7.34 (2H, m), 7.31-7.23 (2H, m), 7.09 (1H, d, J 8.6 Hz), 6.98-6.88 (3H, m), 6.33 (1H, d, J 9.8 Hz), 5.34 (2H, br s), 2.25 (3H, s). LCMS (ES$^+$) RT 3.208 minutes, 411.9 (M+H)$^+$.

EXAMPLE 180

3-[(2-Cyanophenyl)amino]-7-(4-fluorophenyl)-6-oxo-6,7-dihydrothieno[2,3-b]pyridine-2-carboxamide From Example 130 by the method of Example 38. Pale yellow solid. δH (CDCl$_3$) 8.8 (1H, s), 7.66 (1H, d, J 7.8 Hz), 7.52-7.41 (3H, m), 7.33-7.24 (3H, m), 7.12 (1H, t, J 7.6 Hz), 7.01 (1H, d, J 8.3 Hz), 6.49 (1H, d, J 9.7 Hz), 5.51 (2H, br s). LCMS (ES$^+$) RT 2.955 minutes, 405.0 (M+H)$^+$.

EXAMPLE 181

3-[(2-Hydroxyphenyl)amino]-6-oxo-7-phenyl-6,7-dihydrothieno[2,3-b]pyridine-2-carboxamide From Example 160 by the method of Example 38. White solid. δH (DMSO-d6) 9.67 (1H, brs), 8.95 (1H, brs), 7.60-7.40 (5H, m), 7.18-7.14 (2H, m), 6.83-6.74 (3H, m), 6.57-6.50 (1H, m), 6.29 (1H, d, J 9.7 Hz). LCMS (ES$^+$) RT 2.787 minutes, 377 (M+H)$^+$.

EXAMPLE 182

3-[(3-Hydroxyphenyl)amino]-6-oxo-7-phenyl-6,7-dihydrothieno[2,3-b]pyridine-2-carboxamide From Example 161 by the method of Example 38. White solid. δH (DMSO-d6) 9.31 (1H, d), 8.76 (1H, s), 7.67-7.53 (3H, m), 7.50-7.47 (2H, m), 7.37-7.33 (2H, m), 6.70 (1H, t, J 7.9 Hz), 6.40 (1H, d, J 9.6 Hz), 6.34-6.28 (3H, m). LCMS (ES$^+$) RT 2.634 minutes, 377 (M+H)$^+$.

EXAMPLE 183

3-[(2-Cyanophenyl)amino]-6-oxo-7-phenyl-6,7-dihydrothieno[2,3-b]pyridine-2-carboxamide From Example 10 by the method of Example 38. White solid. δH (DMSO-d6) 9.49 (1H, s), 7.73 (1H, dd, J 1.2, 7.7 Hz), 7.45-7.68 (8H, m), 7.34 (1H, d, J 9.6 Hz), 7.08 (1H, t, J 6.5 Hz), 6.95 (1H, d, J 8.3 Hz), 6.44 (1H, d, J 9.6 Hz). LCMS (ES$^+$) RT 2.93 minutes, 387 (M+H)$^+$.

EXAMPLE 184

3-[(2-Chlorophenyl)amino]-6-oxo-7-phenyl-6,7-dihydrothieno[2,3-b]pyridine-2-carboxamide From Example 2 by the method of Example 38. δH (CDCl$_3$) 7.62-7.49 (2H, m), 7.36-7.32 (3H, m), 7.19 (1H, d, J 9.7 Hz), 7.14-7.11 (1H, m), 6.98-6.88 (2H, m), 6.41 (1H, d, J 9.7 Hz), 5.55 (2H, br s). LCMS (ES$^+$) RT 3.164 minutes, 397.9 (M+H)$^+$.

EXAMPLE 185

3-[(3-Cyanophenyl)amino]-6-oxo-7-phenyl-6,7-dihydrothieno[2,3-b]pyridine-2-carboxamide From Example 9 by the method of Example 38. Off-white solid. δH (DMSO-d6) 8.89 (1H, s), 7.20-7.74 (12H, m), 6.53 (1H, d, J 9.6 Hz). LCMS (ES$^+$) RT 2.92 minutes, 387 (M+H)$^+$.

EXAMPLE 186

3-[(2-Cyano-3-methylphenyl)amino]-6-oxo-7-phenyl-6,7-dihydrothieno[2,3-b]pyridine-2-carboxamide From Example 125 by the method of Example 38. δH (DMSO-d6) 9.57 (1H, s), 7.73-7.38 (9H, m), 7.06 (1H, d, J 7.5 Hz), 6.82 (1H, d, J 8.8 Hz), 6.50 (1H, d, J 9.6 Hz), 3.34 (3H, s). LCMS (ES$^+$) RT 3.052 minutes, 401 (M+H)$^+$.

EXAMPLE 187

3-[(2-Cyano-5-methylphenyl)amino]-6-oxo-7-phenyl-6,7-dihydrothieno[2,3-b]pyridine-2-carboxamide From Example 126 by the method of Example 38. δH (DMSO-d6) 9.56 (1H, s), 7.74-7.54 (8H, m), 7.39 (1H, dd, J 2.0, 9.6 Hz), 6.98 (1H, d, J 7.9 Hz), 6.86 (1H, s), 6.51 (1H, d, J 9.7 Hz), 2.33 (3H, s). LCMS (ES$^+$) RT 2.994 minutes, 400.9 (M+H)$^+$.

EXAMPLE 188

3-[(3-Chloro-4-fluorophenyl)amino]-6-oxo-7-phenyl-6,7-dihydrothieno[2,3-b]pyridine-2-carboxamide From Intermediate 75 by the method of Example 45. δH (CDCl$_3$) 9.60 (1H, br s), 7.57-7.50 (3H, m), 7.36-7.34 (2H, m), 7.13-7.02 (3H, m), 6.94-6.90 (1H, m), 6.37 (1H, d, J 9.8 Hz), 5.17 (2H, br s). LCMS (ES$^+$) RT 3.158 minutes, 414 (M+H)$^+$.

EXAMPLE 189

3-[(4-Fluorophenyl)amino]-6-oxo-7-phenyl-6,7-dihydrothieno[2,3-b]pyridine-2-carboxamide From Intermediate 76 by the method of Example 45. δH (DMSO-d6) 9.00 (1H, s), 7.70-7.49 (5H, m), 7.37 (2H, s), 7.29 (1H, d, J 9.6 Hz), 7.18-7.10 (2H, m), 6.95-7.03 (2H, m), 6.42 (1H, d, J 9.6 Hz). LCMS (ES$^+$) RT 3.05 minutes, 380 (M+H)$^+$.

EXAMPLE 190

3-[(3-Chlorophenyl)amino]-6-oxo-7-phenyl-6,7-dihydrothieno[2,3-b]pyridine-2-carboxamide From Intermediate 77 by the method of Example 45. δH (DMSO-d6) 8.98 (1H, s), 7.80-7.70 (3H, m), 7.68-7.66 (1H, m), 7.55 (1H, d, J 9.6 Hz), 7.39-7.35 (1H, m), 7.05-7.03 (2H, m), 6.95-6.92 (1H, m), 6.60 (1H, d, J 9.2 Hz). LCMS (ES$^+$) RT 3.174 minutes, 395.8 (M+H)$^+$.

EXAMPLE 191

3-[(3-Methylphenyl)amino]-6-oxo-7-phenyl-6,7-dihydrothieno[2,3-b]pyridine-2-carbothioamide Hydrogen sulfide gas was bubbled through a solution of Example 139 (680 mg) in pyridine (10 mL) and triethylamine (0.27 mL) at 0° C. The mixture was stirred at r.t. overnight. Volatiles were removed in vacuo and purification by column chromatography (silica, 50% EtOAc in DCM) gave the title compound as a yellow solid (750 mg, 100%). δH (DMSO-d6) 9.40 (1H, br s), 7.85-7.70 (5H, m), 7.60 (1H, d, J 9.7 Hz), 7.32 (1H, t, J 7.4 Hz), 6.94-6.91 (2H, m), 6.83 (1H, d, J 8.1 Hz), 6.61 (1H, d, J 9.7 Hz), 2.42 (3H, s). LCMS (ES$^+$) RT 3.445 minutes, 391 (M+H)$^+$.

EXAMPLE 192

N,N-Diethyl-3-[(3-methylphenyl)amino]-6-oxo-7-phenyl-6,7-dihydrothieno[2,3-b]pyridine-2-carboximidamide A solution of ethyl magnesium bromide (1M, 4.6 mL, 4.6 mmol) was added to diethylamine (0.43 mL, 4.62 mmol) in ether (25 mL) at 0° C. The mixture was heated at reflux for 5 min then Example 139 (300 mg, 0.84 mmol) was added and the mixture heated at reflux for 4 h. Water was added and the mixture was extracted with DCM. The organic phase was dried (Na$_2$SO$_4$) and concentrated in vacuo. Purification by column chromatography (reverse phase silica, 60% EtOH in water) gave the title compound. δH (DMSO-d6) 8.18 (1H, br s), 7.75-7.57 (6H, m), 7.08 (1H, t, J 7.8 Hz), 6.87 (1H, br s), 6.71 (1H, s), 6.65 (2H, t, J 7.0 Hz), 6.56 (1H, d, J 9.6 Hz), 3.17 (4H, br m), 2.25 (3H, s), 0.87 (6H, br t, J 6.9 Hz). LCMS (ES$^+$) RT 2.338 minutes, 430 (M+H)$^+$.

EXAMPLE 193

3-[(3-Methylphenyl)amino]-6-oxo-7-phenyl-6,7-dihydrothieno[2,3-b]pyridine-2-carboximidamide Trifluoroacetic acid (3 mL) was added to a solution of Intermediate 78 (140 mg) in DCM (10 mL). After 2 h at r.t., the volatiles were removed in vacuo and the residue was azeotroped with hexane. The residue was dissolved in DCM and the solution washed with NaHCO$_3$ aq, dried (Na$_2$SO$_4$) and concentrated in vacuo. Purification by prep. HPLC gave the title compound (25 mg). δH (DMSO-d6) 8.11 (1H, s), 7.48-7.33 (6H, m), 6.93 (1H, t, J 10.1 Hz), 6.84-6.47 (3H, m), 6.27 (1H, d, J 12.8 Hz), 3.75-3.72 (3H, v br), 2.04 (3H, s). LCMS (ES$^+$) RT 2.244 minutes, 374 (M+H)$^+$.

EXAMPLE 194

3-[(2,4-Difluorophenyl)amino]-N-(2-hydroxy-2-methylprop-yl)-6-oxo-7-phenyl-6,7-dihydrothieno[2,3-b]pyridine-2-carboxamide 2-Hydroxy-2-methylpropylamine (0.14 g, 1.06 mmol) was added to a solution of Intermediate 79 (0.200 g, 0.35 mmol) and diisopropylethylamine (0.220 mL, 1.26 mmol) in DCM (5 mL) and the mixture stirred at r.t. overnight. The mixture was diluted with DCM and washed with 1M HCl aq. The organic phase was dried (Na$_2$SO$_4$) and concentrated in vacuo. Purification by column chromatography (silica, 70% EtOAc in hexane) gave the title compound as a yellow solid (145 mg, 88%). δH (CDCl$_3$) 8.67 (1H, s), 7.51 (3H, m), 7.19 (2H, m), 7.12 (1H, d, J 9.7 Hz), 7.00 (1H, m), 6.88 (1H, m), 6.75 (1H, m), 6.37 (1H, d, J 9.8 Hz), 5.93 (1H, t), 3.26 (2H, s), 1.13 (6H, s). LCMS (ES$^+$) RT 3.184 minutes, 470 (M+H)$^+$.

EXAMPLE 195

Methyl 2-({3-[(2,4-difluorophenyl)amino]-6-oxo-7-phenyl-6,7-dihydrothieno[2,3-b]pyridin-2-yl}carbonyl)hydrazinecarboxylate A mixture of Intermediate 79 (200 mg, 0.354 mmol) and methyl hydrazinocarboxylate (96 mg, 1.06 mmol) in acetonitrile (5 mL) was heated at 80° C. for 3 days. The mixture was concentrated in vacuo and the residue purified by column chromatography (silica, 30% to 70% EtOAc in hexane). The title compound was obtained as a white solid (55 mg, 32%). δH (DMSO-d6) 9.71 (1H, br s), 9.13 (1H, br s), 7.67-7.60 (3H, m), 7.52 (2H, d), 7.36-7.42 (1H, m), 7.17-7.21 (2H, m), 7.04 (1H, t), 6.40 (1H, d), 3.56 (3H, br s). LCMS (ES$^+$) RT 3.09 minutes, 472 (M+H)$^+$.

EXAMPLE 196

3-[(3-Chlorophenyl)amino]-7-phenylthieno[2,3-b]pyridin-6(7H)-one

From Example 3 by the method of Example 15. δH (DMSO-d6) 8.48 (1H, s), 7.95 (1H, d, J 9.5 Hz), 7.64-7.55 (3H, m), 7.50-7.48 (2H, m), 7.24 (1H, t, J 8.0 Hz), 7.09-7.03 (2H, m), 6.84-6.82 (1H, m), 6.65 (1H, s), 6.53 (1H, d, J 9.5 Hz). LCMS (ES$^+$) RT 3.724 minutes, 352.8 (M+H)$^+$.

EXAMPLE 197

Ethyl 3-anilino-7-[4-(1-hydroxy-1-methylethyl)phenyl]-6-oxo-6,7-dihydrothieno[2,3-b]pyridine-2-carboxylate From Intermediate 81 and aniline by the method of Example 1. White solid. δH (CDCl$_3$) 8.79 (1H, br s), 7.74 (2H, d, J 8.5 Hz), 7.40-7.36 (4H, m), 7.21-7.18 (4H, m), 6.36 (1H, d, J 9.8 Hz), 4.29 (2H, q, J 7.1 Hz), 1.68 (6H, s), 1.33 (3H, t, J 7.1 Hz). LCMS (ES$^+$) RT 3.72 minutes, 449 (M+H)$^+$.

EXAMPLE 198

Ethyl 3-[(2,4-difluorophenyl)amino]-7-{4-[(methylsulfonyl)amino]phenyl}-6-oxo-6,7-dihydrothieno[2,3-b]pyridine-2-carboxylate A solution of sodium ethoxide in EtOH (1 eq.) was added to a suspension of Intermediate 85 (50 mg, 0.08 mmol) in EtOH/Water (8:1, 2 mL). The mixture was stirred at r.t. for 2 h. EtOAc (20 mL) was added and the solution washed with 2M HCl (20 mL), water (2×20 mL) and brine, dried (MgSO$_4$) and concentrated in vacuo. Purification by column chromatography (silica, 20% EtOAc in hexane) gave the title compound (20 mg). δH (CDCl$_3$) 8.53 (1H, br s), 7.30-7.27 (3H, m), 7.16-6.80 (5H, m), 6.32 (1H, d, J 9.8 Hz), 4.21 (2H, q, J 7.1 Hz), 3.05 (3H, s), 1.19 (3H, t, J 7.1 Hz). LCMS (ES$^+$) RT 3.552 minutes, 520 (M+H)$^+$.

EXAMPLE 199

3-[(4-Fluoro-3-methylphenyl)amino]-N-hydroxy-N-methyl-6-oxo-7-phenyl-6,7-dihydrothieno[2,3-b]pyridine-2-carboxamide From Intermediate 88 and N-methylhydroxylamine hydrochloride by the method of Example 194. δH (DMSO-d6) 9.83 (1H, br s), 7.54 (3H, m), 7.45 (2H, m), 7.08 (1H, d, J 9.7 Hz), 7.04-6.96 (2H, m), 6.84 (1H, m), 6.27 (1H, d, J 9.7 Hz), 3.22 (3H, s), 2.15 (3H, s). LCMS (ES$^+$) RT 3.37 minutes, 423.9 (M+H)$^+$.

EXAMPLE 200

2-Acetyl-3-anilino-7-phenylthieno[2,3-b]pyridin-6(7H)-one

From Intermediate 90 and aniline by the method of Example 1. Yellow solid. δH (CDCl$_3$) 10.33 (1H, brs), 7.57-7.47 (3H, m), 7.37-7.29 (4H, m), 7.19-7.14 (3H, m), 7.00 (1H, d, J 9.8 Hz), 6.23 (1H, d, J 9.8 Hz), 2.20 (3H, s). LCMS (ES$^+$) RT 3.611 minutes, 361 (M+H)$^+$.

EXAMPLE 192

N,N-Diethyl-3-[(3-methylphenyl)amino]-6-oxo-7-phenyl-6,7-dihydrothieno[2,3-b]pyridine-2-carboximidamide From Example 139 by the method of Example 192 using diethylamine instead of ethylamine. δH (DMSO-d6) 8.18 (1H, br s), 7.75-7.57 (6H, m), 7.08 (1H, t, J 7.8 Hz), 6.87 (1H, br s), 6.71 (1H, s), 6.65 (2H, t, J 7.0 Hz), 6.56 (1H, d, J 9.6 Hz), 3.17 (4H, br m), 2.25 (3H, s), 0.87 (6H, br t, J 6.9 Hz). LCMS (ES$^+$) RT 2.338 minutes, 430 (M+H)$^+$.

EXAMPLE 201

3-Anilino-6-oxo-7-pyridin-3-yl-6,7-dihydrothieno[2,3-b]pyridine-2-carbonitrile

From Intermediate 92 by the method of Example 1. Yellow solid. δH (CDCl$_3$) 8.77-8.75 (1H, m), 8.65 (1H, d, J 1.3 Hz), 7.74-7.70 (1H, m), 7.54-7.46 (1H, m), 7.40-7.23 (3H, m), 7.10 (1H, t, J 7.4 Hz), 7.03 (2H, d, J 7.6 Hz), 6.43 (1H, d, J 9.8 Hz), 6.35 (1H, br s). LCMS (ES$^+$) RT 3.019 minutes, 345 (M+H)$^+$.

EXAMPLE 202

3-Anilino-6-oxo-7-pyridin-3-yl-6,7-dihydrothieno[2,3-b]pyridine-2-carboxamide

From Example 201 by the method of Example 22. Off-white solid. δH (DMSO-d6) 9.07 (2H, br s), 8.90-8.89 (2H, m), 8.22-8.19 (1H, m), 7.83-7.80 (1H, m), 7.49-7.35 (4H, m), 7.07-7.04 (3H, m), 6.54 (1H, d, J 9.7 Hz). LCMS (ES$^+$) RT 2.719 minutes, 363 (M+H)$^+$.

EXAMPLE 203

3-Anilino-7-phenyl-2-(pyrrolidin-1-ylcarbonyl)thieno[2,3-b]pyridin-6(7H)-one

From Example 14 and pyrrolidine by the method of Example 17. Pale yellow solid. δH (CDCl$_3$) 7.56-7.46 (3H, m), 7.36-7.33 (2H, m), 7.29 (1H, d, J 9.7 Hz), 7.22-7.17 (2H, m), 7.00-6.92 (3H, m), 6.34 (1H, d, J 9.7 Hz), 3.53-3.50 (4H, m), 1.84-1.80 (4H, m). LCMS (ES$^+$) RT 3.46 minutes, 416 (M+H)$^+$.

EXAMPLE 204

3-Anilino-7-phenyl-2-(piperidin-1-ylcarbonyl)thieno[2,3-b]pyridin-6(7H)-one

From Example 14 and piperidine by the method of Example 17. Pale yellow solid. δH (CDCl$_3$) 7.55-7.45 (3H, m), 7.36-7.30 (3H, m), 7.22-7.16 (2H, m), 6.94-6.90 (3H, m), 6.37 (1H, d, J 9.7 Hz), 3.48-3.45 (4H, m), 1.53-1.46 (2H, m), 1.45-1.40 (4H, m). LCMS (ES$^+$) RT 3.53 minutes, 430 (M+H)$^+$.

EXAMPLE 205

3-Anilino-2-[(4-ethylpiperazin-1-yl)carbonyl]-7-phenylthieno[2,3-b]pyridin-6(7H)-one From Example 14 and N-ethylpiperazine by the method of Example 17. δH (CDCl$_3$) 8.25 (1H, br s), 7.75-7.63 (3H, m), 7.44-7.39 (3H, m), 7.31-7.27 (2H, m), 7.04-6.98 (3H, m), 6.45 (1H, d, J 9.7 Hz), 3.64-3.61 (4H, m), 2.43-2.35 (6H, m), 1.06 (3H, t, J 7.2 Hz). LCMS (ES$^+$) RT 2.18 minutes, 459 (M+H)$^+$.

EXAMPLE 206

3-Anilino-7-[4-(dimethylamino)phenyl]-2-(pyrrolidin-1-ylcarbonyl)thieno[2,3-b]pyridin-6(7H)-one From Intermediate 66 and pyrrolidine by the method of Example 17. SH (CDCl$_3$) 9.54 (1H, br s), 7.27-7.14 (6H, m), 6.98-6.93 (2H, m), 6.75 (2H, d, J 9.0 Hz), 6.32 (1H, d, J 9.6 Hz), 3.53 (4H, m), 2.96 (6H, s), 1.82 (4H, m). LCMS (ES$^+$) RT 3.61 minutes, 459 (M+H)$^+$.

EXAMPLE 207

3-[(2,4-Difluorophenyl)amino]-2-(morpholin-4-ylcarbonyl)-7-phenylthieno[2,3-b]pyridin-6(7H)-one From Intermediate 67 and morpholine by the method of Example 17. δH (CDCl$_3$) 8.12 (1H, br s), 7.58-7.49 (3H, m), 7.34-7.31 (2H, m), 7.24 (1H, d, J 9.7 Hz), 6.96-6.82 (2H, m), 6.77-6.70 (1H, m), 6.41 (1H, d, J 9.7 Hz), 3.55 (8H, br s). LCMS (ES$^+$) RT 3.20 minutes, 468 (M+H)$^+$.

EXAMPLE 208

3-{[6-Oxo-7-phenyl-2-(pyrrolidin-1-ylcarbonyl)-6,7-dihydrothieno[2,3-b]pyridin-3-yl]amino}benzonitrile A mixture of Example 9 (250 mg) and pyrrolidine (7 mL) was heated at 110° C. in a sealed tube for 18 h. The mixture was diluted with DCM and washed with dil. HCl aq. The organic phase was dried (MgSO$_4$) and concentrated in vacuo. Purification by column chromatography (silica, 10% EtOAc in DCM) gave the title compound as an off-white solid (112 mg). δH (DMSO-d6) 9.22 (1H, s), 7.28-7.86 (10H, m), 6.68 (1H, d, J 9.6 Hz), 3.33 (4H, m), 1.75 (4H, m). LCMS (ES$^+$) RT 3.29 minutes, 441 (M+H)$^+$.

EXAMPLE 209

3-[(3-Chlorophenyl)amino]-7-phenyl-2-(pyrrolidin-1-ylcarbonyl)thieno[2,3-b]pyridin-6(7H)-one From Example 3 and pyrrolidine by the method of Example 208. Pale yellow solid. δH (DMSO-d6) 8.96 (1H, s), 7.72-7.69 (1H, m), 7.66-7.57 (2H, m), 7.53-7.51 (2H, m), 7.21 (1H, t, J 8.1 Hz), 6.90-6.81 (3H, m), 6.52 (1H, d, J 9.6 Hz), 3.23 (4H, br s), 1.63 (4H, br s). LCMS (ES$^+$) RT 3.635 minutes, 449.9 (M+H)$^+$.

EXAMPLE 210

3-[(2,4-Difluorophenyl)amino]-7-phenyl-2-(pyrrolidin-1-ylcarbonyl)thieno[2,3-b]pyridin-6(7H)-one From Example 12 and pyrrolidine by the method of Example 208. Off-white solid. δH (CDCl$_3$) 9.52 (1H, s), 7.46-7.56 (3H, m), 7.37-7.31 (2H, m), 7.20-7.12 (3H, m), 6.97 (1H, d, J 5.7, 9.0 Hz), 6.83 (1H, ddd, J 2.8, 8.4, 10.8 Hz), 6.72 (1H, tq, J 1.5, 9.0 Hz), 6.36 (1H, d, J 9.7 Hz), 3.52 (4H, m), 1.82 (4H, m). LCMS (ES$^+$) RT 3.57 minutes, 452 (M+H)$^+$.

EXAMPLE 211

3-[(4-Fluorophenyl)amino]-7-phenyl-2-(pyrrolidin-1-ylcarbonyl)thieno[2,3-b]pyridin-6(7H)-one From Intermediate 76 and pyrrolidine by the method of Example 17. Off-white solid. δH (DMSO-d6) 8.7 (1H, s), 7.3 (4H, m), 7.2 (2H, m), 6.8 (2H, m), 6.7 (2H, m), 6.28 (1H, d, J 9.6 Hz), 3.0 (4H, m), 1.42 (4H, m). LCMS (ES$^+$) RT 3.487 minutes, 434 (M+H)$^+$.

EXAMPLE 212

3-[(2,4-Difluorophenyl)amino]-6-oxo-7-phenyl-N-pyrrolidin-3-yl-6,7-dihydrothieno[2,3-b]pyridine-2-carboxamide To a solution of Intermediate 93 in methanol (20 mL) was added Pd(OH)$_2$ (20% on carbon, 10 mg) and the reaction stirred at r.t. under an atmosphere of hydrogen (balloon) for 4 h. The reaction was filtered through a pad of celite and the filtrate concentrated in vacuo to give the product as a gum. The gum was re-dissolved in acetonitrile and water and freeze dried to give the title compound as an off-white solid (44 mg). δH (DMSO-d6) 9.23 (1H, bs), 8.50 (1H, s), 8.20 (1H, m), 7.72 (2H, m), 7.68 (2H, m), 7.46 (2H, m), 7.17 (2H, m), 6.57 (1H, d, J 9.7 Hz), 4.47 (1H, m), 3.25-2.75 (4H, m), 2.11 (1H, m), 1.80 (1H, m). LCMS (ES$^+$) RT 2.31 minutes, 467 (M+H)$^+$.

The following assays and animal models can be used to demonstrate the potency and selectivity of the compounds according to the invention. In each assay an IC50 value was determined for each test compound and represents the concentration of compound necessary to achieve 50% inhibition.

Preparation of Activated Human P38α for Inhibitor Assays.

Purification of Human p38α

Human p38α, incorporating an N-terminal (His)6 tag, was expressed in baculovirus-infected High-Five™ cells (Invitrogen) according to the manufacturers instructions. The cells were harvested 72 h post-infection and lysed in phosphate buffered saline (PBS) containing 1% (w/v) 13-octylglucoside and Complete, EDTA-free protease inhibitors (Roche Molecular Biochemicals). The lysate was centrifuged at 35000×g for 30 min at 4° C. and the supernatant applied to a NiNTA™ column (Qiagen). Bound protein was eluted by 150 mM imidazole in PBS (after a wash with 15 mM imidazole in PBS) and directly applied to a HiTrap Q™ column (AP Biotech). Bound protein was eluted using a 20 column volume, 0 to 1M NaCl gradient. Fractions containing (His)6-p38 were aliquotted and stored at −70° prior to their activation.

Preparation of GST-MKK6EE-Containing Lysates

E. coli (BL21 pLysS) expressing the constituitively activated form of human MKK6 fused with an N-terminal glutathione-S-transferase tag (GST-MKK6EE) were harvested by centrifugation and frozen at −70°. Cells were lysed by resuspension in ¹/₁₀th the culture volume of PBS containing Complete, EDTA-free™ protease inhibitors followed by sonication on ice for 4×15 sec. Cell debris was removed by centrifugation at 35,000×g and the resultant supernatant stored in aliquots at −70°.

Activation of (His)6-p38

0.45 mL of purified (His)6-p38 was incubated with 50 µL of the GST-MKK6EE-containing lysate for 30 min at 23° in the presence of 1 mM β-glycerophosphate, 10 mM MgCl$_2$ and 9 mM ATP. The extent of activation was monitored by mass spectrometric detection of the doubly-phosphorylated form of (His)6-p38, which routinely comprised greater than 90% of the final (His)6-p38 preparation. The activated (His) 6-p38 was then diluted ×10 in PBS and repurified using the method described above. The concentration of purified, activated (His)6-p38 was measured by UV absorbance at 280 nm using A280, 0.1%=1.2 and the preparation stored in aliquots at −70° prior to its use in inhibitor assays.

p38 Inhibition Assays

Inhibition of Phosphorylation of Biotinylated Myelin Basic Protein (MBP)

The inhibition of p38 catalysed phosphorylation of biotinylated MBP is measured using a DELFIA based format. The assay was performed in a buffer comprising, 20 mM HEPES (pH 7.4), 5 mM MgCl$_2$ and 3 mM DTT. For a typical IC50 determination, biotinylated MBP (2.5 µM) was incubated at room temperature in a streptavidin-coated microtitre plate together with activated gst-p38 (10 nM) and ATP (1 µM) in the presence of a range of inhibitor concentrations (final concentration of DMSO is 2 percent). After fifteen minutes the reaction was terminated by the addition of EDTA (75 mM). The microtitre plate was then washed with Tris buffered saline (TBS), prior to the addition of 100 µl of anti-phospho MBP antibody (mouse) together with europium-labeled anti-mouse IgG antibody. After one hour at room temperature the plate was again washed in TBS followed by the addition of Enhancement solution (PerkinElmer Wallac). Fluorescence measurements were performed after a further fifteen minutes at room temperature. IC50 values are determined from the plot of Log$_{10}$ inhibitor concentration (x-axis) versus percentage inhibition of the fluorescence generated by a control sample in the absence of inhibitor (y-axis).

Purification of Human Peripheral Blood Mononuclear Cells

Peripheral blood mononuclear cells (PBMC) were isolated from normal healthy volunteers. Whole blood was taken by venous puncture using heparinised vacutainers (Becton Dickinson), diluted 1 in 4 in RPMI 1640 (Gibco, UK) and centrifuged at 400 g for 35 min over a Ficoll-paque gradient (Amersham-Pharmacia Biotech, UK). Cells at the interface were removed and washed once followed by a low speed spin (250 g) to remove platelets. Cells were then resuspended in DMEM containing 10% FCS, penicillin 100 units ml$^{-1}$, streptomycin 50 µg ml$^{-1}$ and glutamine 2 mM (Gibco, UK).

Inhibitor Dilutions

Inhibitor stocks (20 mM) were kept as a frozen solution (−20° C.) in DMSO. Serial dilutions of inhibitors were performed in DMSO as 250-times concentrated stocks. Inhibitors were diluted 1 in 250 into tissue culture media, pre-warmed to 37° C. and transferred to plates containing PBMC. PBMC and inhibitors were incubated together for 30 mins prior to addition of LPS. Inhibitors used in whole blood assays were prepared according to a different regime. Using the same stock solution serial dilutions of inhibitors were performed in DMSO. Inhibitors were then diluted 1 in 500 straight into whole blood in a volume of 1 µL. Inhibitor was incubated with whole blood for 30 mins prior to the addition of LPS.

LPS Stimulation of PBMC

PBMC were resuspended at a density of $2 \times 10^5$ cells/well in flat bottomed 96 well tissue culture treated plates. After the addition of inhibitor cells were stimulated with an optimal dose of LPS (E coli strain B5:055, Sigma, at a final concentration of 1 g ml$^{-1}$) and incubated at 37° C. in 5% $CO_2$/95% air for 18 hours. TNF-α levels were measured from cell free supernatants by sandwich ELISA (BioSource #CHC1751).

LPS Stimulation of Whole Blood

Whole blood was taken by venous puncture using heparinised vacutainers (Becton Dickinson), and 500 µl of blood aliquoted into each well of a 24 well tissue culture treated plate. After the addition of inhibitor cells were stimulated with an optimal dose of LPS (E coli strain B5:055, Sigma, at a final concentration of 1 µg ml$^{-1}$) and incubated at 37° C. without $CO_2$ for 18 hours. TNF-α levels were measured from cell free supernatants by sandwich ELISA (BioSource #CHC1751).

Rat LPS Induced TNF Release

Male Lewis rats (180-200 g) are anaesthetised with Isofluor and injected i.v. with LPS* in a volume of 0.5 ml sterile saline. After 90 minutes blood is collected into EDTA tubes for preparation of plasma samples. Plasma is stored at −70° C. prior to assay for TNFα by commercial ELISA.

Rat CIA

Female Lewis rats (180-200 g) are anaesthetised with Isofluor and immunised i.d. at the base of the tail with 2×100 µl of emulsion containing 4 mg/ml bovine collagen II in 0.01M acetic acid and Freund's Incomplete Adjuvant at a ratio of 1:1. A polyarthritis develops with onset from about 13 days post sensitisation. The disease is mainly confined to the ankles and is quantified by plethysmometry. Results are expressed as change in paw volume over time.

In the p38 inhibitor assays described above compounds of the invention have IC$_{50}$ values of around 1 µM and below. The compounds of the invention are clearly potent inhibitors of p38 kinase, especially p38α kinase.

The invention claimed is:

1. A compound of formula (1):

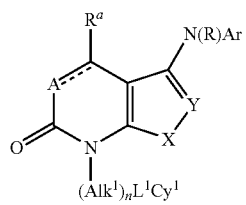

(1)

wherein:
  the dashed line joining A and $C(R^a)$ is present and represents a bond and A is a —$C(R^b)$= group;
  $R^a$ is a hydrogen atom or a $C_{1-4}$alkyl group;
  $R^b$ is a hydrogen atom;
  R is a hydrogen atom or a straight or branched $C_{1-6}$ alkyl group;
  X is an —S— atom;
  Y is a —CH= or —C(R$^{10}$)= group wherein R$^{10}$ is —CN, —CONH$_2$, —CONHet$^1$, —CON(R$^{12}$)Het, —CON(R$^{12}$)Alk$^5$Het or —CO$_2$Alk$^6$;
  —NHet$^1$ represents pyrrolidinyl, piperazinyl, morpholinyl or piperidinyl;
  Het represents cyclopentyl, cyclohexyl, pyrrolidinyl, piperazinyl, morpholinyl or piperidinyl;
  R$^{12}$ represents hydrogen or $C_{1-6}$alkyl;
  Alk$^5$ is a straight or branched $C_{1-6}$alkylene chain;
  Alk$^6$ is a straight or branched $C_{1-8}$alkyl group;
  n is zero or the integer 1;
  Alk$^1$ is —CH$_2$— or —CH$_2$CH$_2$—;
  L$_1$ is a covalent bond;
  Cy$^1$ is an optionally substituted $C_{3-7}$cycloalkyl, phenyl, thienyl, pyridyl or indolyl group, wherein the optional substituents on Cy$^1$ are selected from halogen, $C_{1-6}$alkyl, halo$C_{1-6}$alkyl, $C_{1-6}$alkoxy, halo$C_{1-6}$alkoxy, cyano, —CO$_2$CH$_3$, —CO$_2$C(CH$_3$)$_3$, nitro, amino, —NHCH$_3$, —N(CH$_3$)$_2$, —C(O)CH$_3$ and —NHCOCH$_3$;
  Ar is an optionally substituted pyridine, wherein the optional substituents on Ar are selected from halogen, $C_{1-6}$alkyl, halo$C_{1-6}$alkyl, $C_{1-6}$alkoxy, halo$C_{1-6}$alkoxy, cyano, —CO$_2$CH$_3$, —CO$_2$C(CH$_3$)$_3$, nitro, amino, —NHCH$_3$, —N(CH$_3$)$_2$, —C(O)CH$_3$ and —NHCOCH$_3$; or a pharmaceutically acceptable salt thereof.

2. The compound according to claim 1 wherein R is a hydrogen atom.

3. The compound according to claim 1 wherein $R^a$ is a hydrogen atom.

4. A compound according claim 1 wherein n is the integer 1.

5. The compound according to claim 1 wherein n is zero.

6. A compound according to claim 1 wherein Cy$^1$ is an optionally substituted $C_{3-7}$cycloalkyl group, wherein the optional substituents on Cy$^1$ are selected from halogen, $C_{1-6}$alkyl, halo$C_{1-6}$alkyl, $C_{1-6}$alkoxy, halo$C_{1-6}$alkoxy, cyano, —CO$_2$CH$_3$, —CO$_2$C(CH$_3$)$_3$, nitro, amino, —NHCH$_3$, —N(CH$_3$)$_2$, —C(O)CH$_3$ and —NHCOCH.

7. The compound according to claim 6 wherein Cy$^1$ is a cyclopropyl group.

8. A compound according to claim 1 wherein Cy$^1$ is an optionally substituted phenyl group, wherein the optional substituents on Cy$^1$ are selected from halogen, $C_{1-6}$alkyl, halo$C_{1-6}$alkyl, $C_{1-6}$alkoxy, halo$C_{1-6}$alkoxy, cyano, —CO$_2$CH$_3$, —CO$_2$C(CH$_3$)$_3$, nitro, amino, —NHCH$_3$, —N(CH$_3$)$_2$, —C(O)CH$_3$ and —NHCOCH$_3$.

9. The compound according to claim 8 wherein Cy$^1$ is a phenyl group.

10. A compound according to claim 1 wherein Y is —C(R$^{10}$)=.

11. The compound according to claim 10 wherein R$^{10}$ is —CONH$_2$.

12. A compound which is
  ethyl 6-oxo-7-phenyl-3-(pyridin-3-ylamino)-6,7-dihydrothieno[2,3-b]pyridine-2-carboxylate;
  ethyl 3-[(2-chloropyridin-3-yl)amino]-6-oxo-7-phenyl-6,7-dihydrothieno[2,3-b]pyridine-2-carboxylate;
  3-[(6-methylpyridin-2-yl)amino]-6-oxo-7-phenyl-6,7-dihydrothieno[2,3-b]pyridine-2-carbonitrile;
  3-[(6-methylpyridin-2-yl)amino]-6-oxo-7-phenyl-6,7-dihydrothieno [2,3-b]pyridine-2-carboxamide;

3-[(6-chloropyridin-2-yl)amino]-6-oxo-7-phenyl-6,7-dihydrothieno[2,3-b]pyridine-2-carbonitrile;

3-[(6-chloropyridin-2-yl)amino]-6-oxo-7-phenyl-6,7-dihydrothieno[2,3-b]pyridine-2-carboxamide;

or a pharmaceutically acceptable salt, solvate, hydrate, or N-oxide thereof.

13. A pharmaceutical composition comprising a compound of claim 1 together with one or more pharmaceutically acceptable carriers, excipients or diluents.

14. A compound according to claim 12 which is ethyl 6-oxo-7-phenyl-3-(pyridin-3-ylamino)-6,7-dihydrothieno[2,3-b]pyridine-2-carboxylate.

15. A compound according to claim 12 which is ethyl 3-[(2-chloropyridin-3-yl)amino]-6-oxo-7-phenyl-6,7-dihydrothieno[2,3-b]pyridine-2-carboxylate.

16. A compound according to claim 12 which is 3-[(6-methylpyridin-2-yl)amino]-6-oxo-7-phenyl-6,7-dihydrothieno[2,3-b]pyridine-2-carbonitrile.

17. A compound according to claim 12 which is 3-[(6-methylpyridin-2-yl)amino]-6-oxo-7-phenyl-6,7-dihydrothieno[2,3-b]pyridine-2-carboxamide.

18. A compound according to claim 12 which is 3-[(6-chloropyridin-2-yl)amino]-6-oxo-7-phenyl-6,7-dihydrothieno[2,3-b]pyridine-2-carbonitrile.

19. A compound according to claim 12 which is 3-[(6-chloropyridin-2-yl)amino]-6-oxo-7-phenyl-6,7-dihydrothieno[2,3-b]pyridine-2-carboxamide.

* * * * *